United States Patent [19] [11] Patent Number: 6,047,602
Lynnworth [45] Date of Patent: Apr. 11, 2000

[54] ULTRASONIC BUFFER/WAVEGUIDE

[75] Inventor: Lawrence C. Lynnworth, Waltham, Mass.

[73] Assignee: Panametrics, Inc., Waltham, Mass.

[21] Appl. No.: 08/879,690

[22] Filed: Jun. 20, 1997

Related U.S. Application Data

[60] Provisional application No. 60/029,282, Oct. 29, 1996.

[51] Int. Cl.[7] ................................................. G01N 29/00
[52] U.S. Cl. ............................................................. 73/632
[58] Field of Search ........................ 73/632, 644, 861.18, 73/861.25, 861.26, 861.27, 861.28, 861.29, 861.31

[56] References Cited

U.S. PATENT DOCUMENTS

| | | | |
|---|---|---|---|
| 3,575,050 | 4/1971 | Lynnworth | 73/194 |
| 3,973,152 | 8/1976 | Karplus | 310/8.3 |
| 4,286,470 | 9/1981 | Lynnworth | 73/861.18 |
| 4,320,659 | 3/1982 | Lynnworth | 73/589 |
| 4,336,719 | 6/1982 | Lynnworth | 73/861.27 |
| 4,373,401 | 2/1983 | Baumoel | 73/861.18 |
| 4,783,997 | 11/1988 | Lynnworth | 73/644 |
| 4,787,252 | 11/1988 | Jacobson et al. | 73/861.28 |
| 5,159,838 | 11/1992 | Lynnworth | 73/644 |
| 5,251,490 | 10/1993 | Kronberg | 73/861.25 |
| 5,515,733 | 5/1996 | Lynnworth | 73/861.27 |
| 5,600,073 | 2/1997 | Hill | 73/861.04 |

FOREIGN PATENT DOCUMENTS

| 2092802 | 6/1970 | France . |
|---|---|---|
| WO 96/41157 | 12/1996 | WIPO . |

OTHER PUBLICATIONS

Lynnworth, L.C. et al: "300 degrees C clamp–on ultrasonic transducers for measuring water flow and level" 1996 IEEE Ultrasonics Symposium Proceedings (Cat. No. 96CH35993), 1996 IEEE Ultrasonics Symposium. Proceedings, San Antonio, TX, USA Nov. 3–6, 1996, ISBN 0–7803–3615–1, 1996, New York, NY, USA, IEEE, USA, pp. 407–412 vol. 1 XP002056989.

*Primary Examiner*—Hezron Williams
*Assistant Examiner*—Richard A. Moller
*Attorney, Agent, or Firm*—Michael I. Falkoff; Nutter, McClennon & Fish, LLP

[57] ABSTRACT

A waveguide couples ultrasonic energy from a source on one side of a fluid-bounding wall, such as a conduit, into fluid on the other side of the wall. The waveguide has a buffer that couples to the source, and a seat with an exit face, while an intermediate portion contains a redirecting surface for internally redirecting energy propagated along the buffer toward the exit face to exit as a narrow directed beam. The waveguide core has a rectangular cross section which is narrow, i.e., has an aspect ratio above two and preferably above three or four, while the buffer has a length effective to thermally isolate or protect the source from the conduit. The waveguide attaches easily, either as a clamp-on or welded unit, to a pipe or spoolpiece, allowing local fabrication of massive or custom flow cells, such as large spoolpieces with Gauss-Chebyshev interrogation paths. Several guides may be positioned in an array to cover interrogation paths for an extended range of sound speeds or flow rates. In one embodiment the redirecting face may be curved, or stepped at different angles, to provide output beams at several or a continuum of exit angles. A low sound speed material may be added to control the refraction angle of the exit beam in the wall or fluid. The construction readily adapts to wetted systems. The waveguide may have the overall shape of a hockey stick, with the buffer and the seat lying in a common plane, or one may curve into, or join at an angle, the other. Features such as holes, notches or the like may provide reference echoes for a flow meter to automatically calculate temperature-dependent transit time corrections for the buffer, and additional reflective surfaces or topological features such as holes may redirect echoes or noise out of the measurement path. In one embodiment, the buffer is a thin tube which couples shear waves into the seat portion, which has a rectangular cross section.

36 Claims, 34 Drawing Sheets

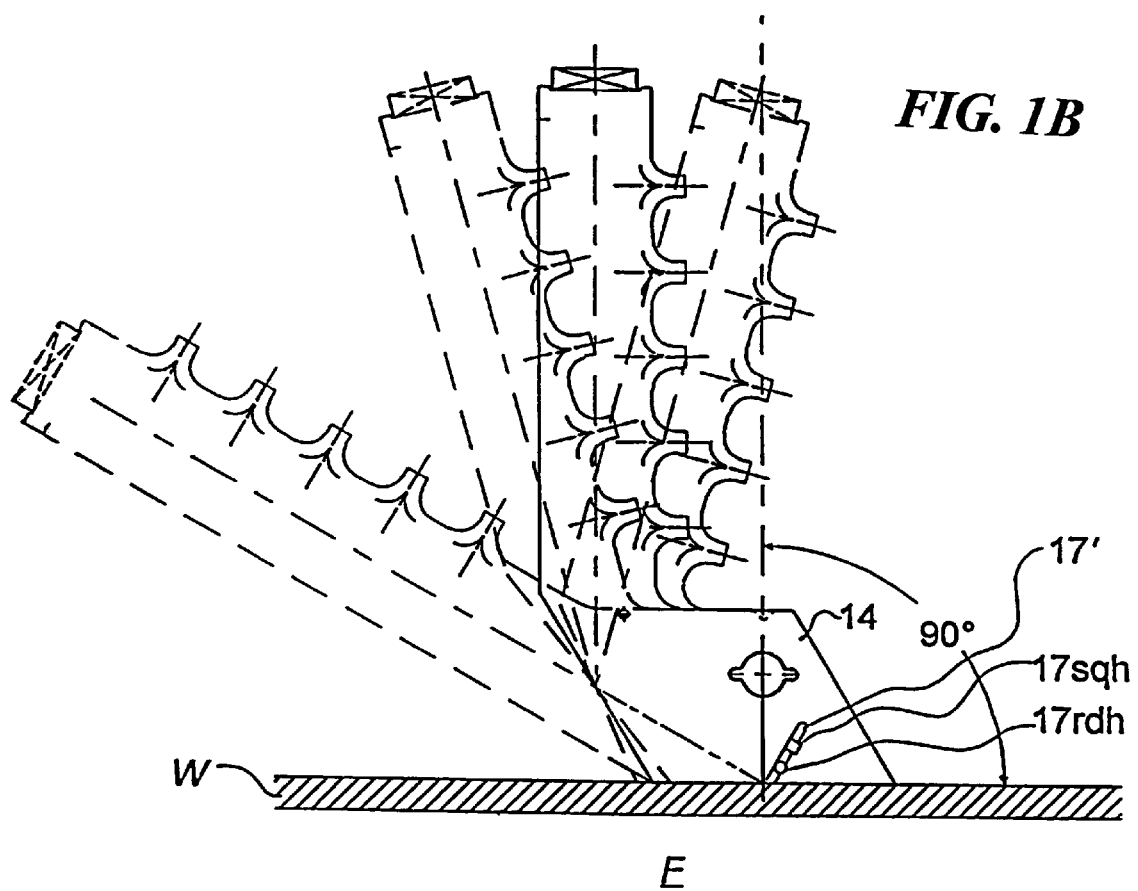

ULTRASONIC BUFFER/WAVEGUIDE

REFERENCE TO RELATED APPLICATION

This application is related to and claims the benefit of provisional application no. 60/029,282 filed on Oct. 29, 1996.

BACKGROUND OF THE INVENTION

The present invention relates to ultrasonic flow measurement systems and particularly to wedges or buffer rods used to couple a transducer to a pipe or conduit wall for effecting a fluid measurement.

In general it may be said that accurate ultrasonic flow measurements require that the paths of interrogation, whether along diameter paths of a conduit or chordal paths such as those used in quadrature systems, be well defined in order to accurately apply equations to compute flow. In clamp-on systems in the prior art this has often entailed mounting wedges axially centered on a conduit or effecting precision machined bores in the conduit to receive special waveguides. Well defined paths are especially important for off-diameter paths lying outside the mid-radius circle, where the flow profile is sharply curved. Such paths have generally been achieved with precision bores holding straight waveguides. Indeed, it would appear a contradiction of objectives if one sought to obtain well defined paths using refracted beams of ultrasound.

Applicant has previously proposed a measurement system wherein vertically polarized shear waves were used to measure flow. The system involved a buffer rod having a half inch square cross section in which vertically polarized shear waves were transmitted to the pipe. Another buffer rod construction is shown in U.S. Pat. No. 3,973,152 issued to Karplus. That construction utilizes a large number of sheets which are pressed together to make a wedge. This design does not specifically deal with the notion of interposing a long buffer or long heat dissipating member between a hot pipe and a piezo transducer which must remain cool. Rather, in proposing a laminated construction, the '152 patent aims to reduce ringing that occurs in solid wedge designs. Another buffer rod construction appears in applicant's earlier U.S. Pat. No. 3,575,050, issued Apr. 13, 1971. Various other designs are known either for wedges which allow a transducer to be clamped onto a pipe without special machining, or for buffer rods which allow a transducer to connect to a hot pipe without heating excessively. However, the very traits which make a buffer rod a good waveguide may also result in ringing, or restrict the buffer to a limited number of frequencies or wavetypes, or result in a poorly directed output beam. Similarly, mounting wedges generally require specific set-up, or are configured for one size or range of pipe, and generally launch refracted waves through the wall along a diametral path.

Thus there remains a need for more versatile and effective coupling for ultrasonic transducers, and especially for a buffered coupling or waveguide which is adaptable to various pipe orientations to launch signals with a high degree of accuracy and control.

SUMMARY OF THE INVENTION

The present invention provides a buffer waveguide for interposition between a source of shear waves and a fluid or the wall of a conduit containing the fluid. The buffer waveguide is solid but relatively thin, shaped in a side view somewhat like a hockey stick and characterized by an elongated lead-in or buffer portion, corresponding to the hockey stick handle, and a generally shorter seat/radiator portion corresponding to the blade of the stick. Energy traveling down the buffer is guided by or redirected off an internal surface and propagates without dispersion as shear waves in the blade to an exit face which seats against the pipe or fluid. The waveguide is characterized by a length $X3$, thickness $X1$ and a core width $X2$ such that it has a core rectangular cross section of relatively high aspect ratio with preferably $X1 << X2 << X3$. The thickness $X1$ is comparable to the wavelength of a shear wave of the ultrasonic energy to be propagated therein, and is preferably large enough so that the exit face of the radiator portion, which is preferably both flat and rectangular, provides an orienting support surface allowing the blade to be clamped directly onto or welded to a pipe. Small topological features such as thermocouple mounting tabs may be added outside the core rectangle. The core width $X2$ is much greater than the shear wavelength therein, and preferably also greater than half the length of the shear wave packet.

The buffer may include small flanges, weld beads, one or more reflective notches, or holes located outside the principal ray path along the buffer; it may also include a step in thickness to control depth of insertion of the seat portion though a pipe wall into which the device is to be welded. In general, the principal bounding surfaces or major faces of the waveguide are planar and parallel, while narrow edge faces may be oriented obliquely and serve to reflect energy traveling down the handle to the exit face of the blade, or to deflect spurious path energy. In one embodiment several oblique faces in parallel planes reflect the incoming energy at a plurality of angles to result in an extended emission of energy along the blade portion. In another embodiment a continuously variable angle of incidence is provided along the exit face by an internal curved reflective surface. To enhance coupling, or to control the angle of refraction into a pipe or fluid, the exit face may further incorporate, or may rest in a slot containing, a low sound speed material; the active (piezoelectric or transducer) end of the buffer may include a tungsten-loaded plastic or silicone rubber attenuative material to allow high pulse repetition frequencies to be used.

The waveguide is advantageously mounted in a spoolpiece either by welding into a slot in the spoolpiece, or by welding into a custom jig or onto a standard pipe riser clamp which is then clamped against the spoolpiece. Custom spoolpieces may be locally fabricated by the simple expedient of attaching appropriately oriented buffer/waveguide assemblies to a pipe segment. This arrangement is especially useful for measurements on standard pipes in a plane perpendicular to the pipe axis, such as swirl measurements. In other embodiments, the buffer is formed of a sheet metal stamping folded about a central axis and having reflective faces formed by internal or recessed edges of the stamping. In a representative example, the buffer has a thickness of 6 millimeters with a width of 3–6 centimeters, a length of about 15 to 20 centimeters and a blade length of about 4 to 8 centimeters. The 6 millimeter wide exit face sits substantially flat against pipes having diameters in the range of 8–10 inches or more. Little preparation of the pipe surface is required to employ the buffer in a clamp-on mounting. For weld-on or weld-in installations, a flat or slot is milled and the waveguide is welded to the pipe. The high-aspect-ratio rectangular cross section of the buffer results in a well propagated shear wave signal with little ringing or mode conversion. Energy leaving the exit face of the blade propagates to one or more well-defined receiving locations within the pipe interior along precise paths, thus enhancing measurement accuracy and allowing, for example, off-diameter paths to be interrogated for profile compensation or tomographic imaging. Slots or recesses may be milled and counter-milled to prepare sites in the conduit or spoolpiece wall for accurately seating the buffer and directing its output along a defined plane in the fluid.

In a preferred embodiment made of sheet or plate stock, the buffer is a thin solid sheet which may be conceptualized as a body comprised of a triangle plus one or more polygonal extensions forming the standoff and the blade. The triangle is an integral wedge which receives shear energy from the buffer portion, and radiates the energy along its hypotenuse. Regions of the hockey stick blade outside the triangle may include holes positioned out of the signal path to accommodate clamps or hooks without impairing the wave function, and portions of the lead-in or buffer section outside the principal ray path may include isolated scattering features to provide reference echoes for calibration and dynamic temperature compensation. In the blade portion, echoes from a first reference reflector that is normal to the path centerline and from a second reflector at the toe of the blade contain time and amplitude information from which the sound speed in the blade, as well as the efficacy of coupling to the pipe or fluid, are calculated.

BRIEF DESCRIPTION OF THE DRAWINGS

FIG. 1B is a conceptual drawing showing a range of angles contemplated between the buffer portion relative to the wedge or foot portion;

DETAILED DESCRIPTION

Figure 1:
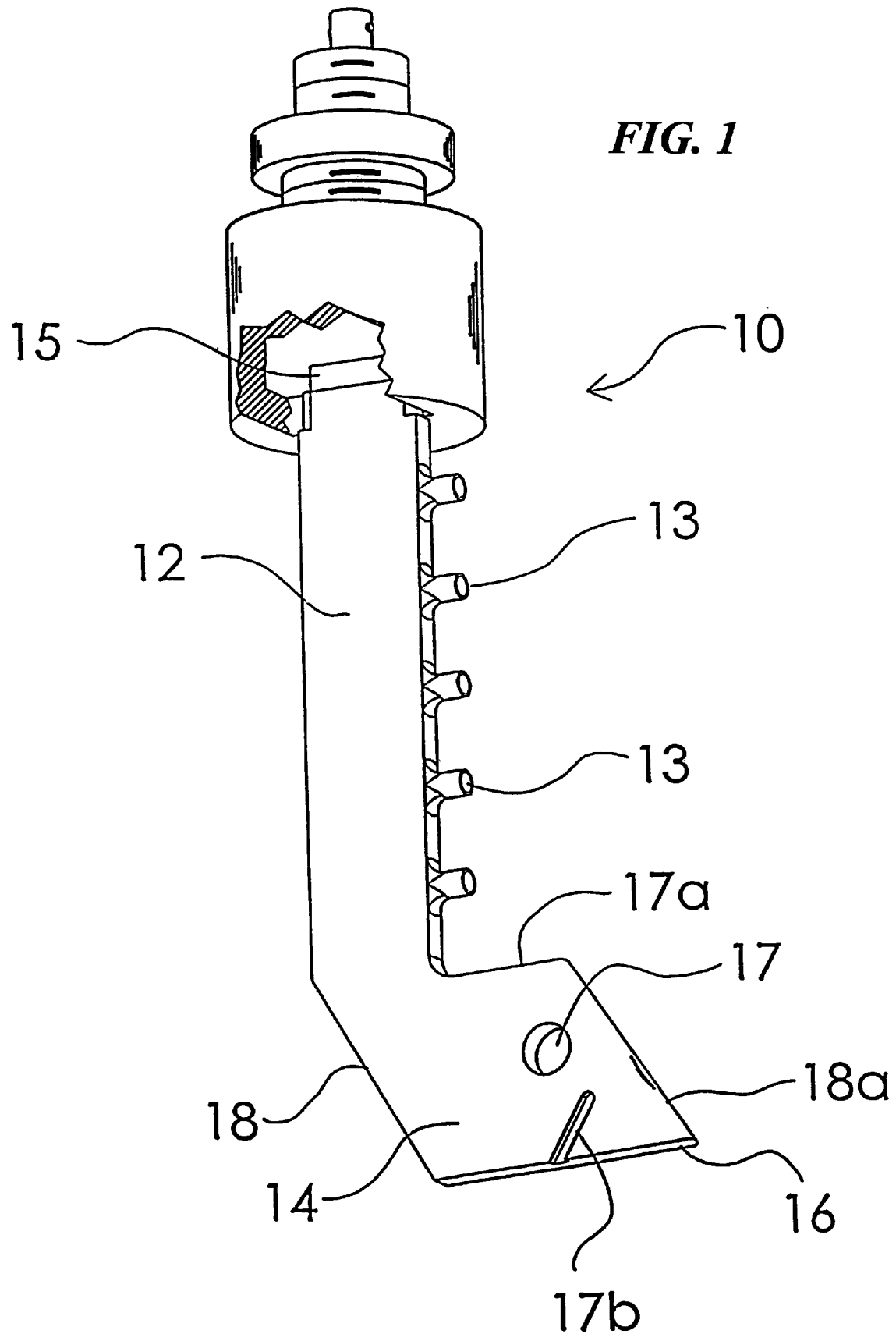
FIG. 1 shows an elongated nondispersive directive waveguide of the present invention for installation on a pipe, conduit or other solid body, to measure flow, liquid presence or level, or other fluid characteristic.

The present invention is a waveguide which acts as a buffer to provide a remote coupling face for signals from an ultrasonic source or transducer, a body for non-dispersive propagation of the signals, and an exit face for coupling signals out of the body, either into a pipe wall, or directly into a fluid, generally at a defined refraction angle along a controlled path, where the refraction angle depends in part on the soundspeed in the fluid medium. The waveguide is thin, and has major opposed faces, so that it is plate-like. It has roughly the shape of a hockey stick. Various embodiments exploit this geometry for structural features, for flow-compatible intrusions into the pipe and for signal enhancement in particular situations.

Unless stated otherwise it shall be assumed that when we say pulses we are referring to shear wave pulses having particle motion parallel to the major faces of the waveguide. In the fluid the wave is longitudinal. When the buffer or transducer assembly is wetted, the buffer thickness is preferably not less than about half the pipe wall thickness, for welded high-pressure installations. For a welded-in buffer, if the buffer were too thin compared to the pipe wall, the relatively thick weld required by codes or normal welding practice would degrade signal and increase short circuit. It has been found in tests on SS ten-inch schedule 40 pipe having a pipe wall about ⅜-inch or 10-mm thick, that standard fillet welds yield satisfactory signals when the thickness of the waveguide is about 6 mm. As the pressure-bearing area exposed to a fluid (in the wetted case) is less than one square inch, and can be about ⅔ square inch, the force on the weld is less in pounds than the numerical value of the fluid pressure, e.g., 1500 psig or kg/sq inch, force ~1000 pounds or kg. In the clamp-on mode, the same small area means a modest coupling force of 1000 pounds or kg yields a high coupling pressure, 1500 psi or kg/sq inch, respectively. Thus the new design is appropriate for both clamp-on and wetted applications.

These features, and the resultant well-defined transmitted beam make the waveguide useful not only for measuring liquids in conduits, but generally also for single-phase or two-phase fluids, and for interrogations by transmission, reflection, range-gated reflection and other modes, in active or passive signal modes.

Table 1 provides a summary overview of structural features which may be incorporated in different embodiments of the invention, and systems or processing protocols implemented with these waveguides, and different methods of making the waveguides.

TABLE 1

| OVERVIEW OF EMBODIMENTS | |
|---|---|
| | RELEVANT FIGS. |
| Clamp-On, Wetted, Hybrid (hinged, removable extension, low-c insert in slot) | 1, 1A, 2F |
| General Plate Geometry: Usually flat; can be curved or bent. If bent sharply, included angle should exceed 135° C.: | 1F |
| Material of Waveguide: Usually steel or stainless steel; the standoff can be all or partly plastic, ceramic. | 1, 1M, 2A |
| Temperature Range for Typical Application: Normally −40 to +125° C.; extremes from −196 to +300° C., depending on the length of extension. | 1 |
| Temperature Compensation: Derived from T measurement or from reference echo at time $t_w$; other echoes can be generated for additional information on T distribution. Temperature sensor tabs can be placed outside the main beam without degrading the SNR. | 1, 1G, 1H |
| Axial Flow ($V_z$) is main objective. Secondary Flow is secondary objective, but can be essential to achieving high accuracy in $V_z$. Secondary flow includes swirl, swirl angle $\Psi$, circulation $\Gamma$, and the crossflow vector $V_x$ which is the resultant of orthogonal components $V_{x1}$ and $V_{x2}$. Present invention can be combined with prior art or co-pending new measurement techniques for measuring sound speed c and/or secondary flow components in a plane perpendicular to the pipe axis. For example, c can be measured at high temperature using a tube waveguide, a bundle of small-diameter wires in a tube, or a marginally-dispersive waveguide at each end of the diameter. | 2E |

TABLE 1-continued

OVERVIEW OF EMBODIMENTS

| | RELEVANT FIGS. |
|---|---|
| Applications: Mainly flow, but also liquid level, liquid presence. | 1J |
| Flow Measurement Principles: Mainly contrapropagation, but also reflection, tag cross-correlation, differential modes for fast response, low-cost flow switch, circulation fluctuation frequency obtained from transit times upstream and downstream of a vortex shedding strut. Special interrogation methods may be needed in highly turbulent flows, especially if the fluid is compressible. To obtain a reliable reading as fast as possible, the number of interrogations in a particular direction depends on the probability that a particular reading, or an average of SNR-discriminated readings, is likely to be correct. Readings may be SNR-weighted. One good reading (high SNR) can outweigh many poor-SNR readings. Noise in a particular structure is a function of flow velocity or Reynolds Number Re. | 6 |
| Fluids: Liquids, primarily. High temperature liquids, cryogenic liquids. Gases, especially at high pressure in steel pipe, for example, steam; gas at low to moderate pressure in plastic pipe; multiphase fluids. | 3, 8A |
| Acoustic Propagation Parameters Measured: Time and amplitude; amplitude vs frequency; amplitude vs path length (differential path multireceiver sites); noise spectrum; chirped excitation for multifrequency measurement; use of chirp to sort out paths when transducers of different frequencies are at the ends of different paths, e.g., inboard vs outboard GC paths. | 1A 3B, 6 |
| Form Factor for Waveguide: Generally like a thin hockey stick ~6 mm thick, ~30 mm extension width, ~100 to 300 mm extension (standoff) length, wedge usually chamfered, radiating length usually two to three times greater than longest dimension of shear wave crystal. Dimensions of crystal preferably closely match the corresponding core dimensions of the standoff. Radiating end may be contoured to match pipe curvature when making measurements in a plane perpendicular to the pipe axis. The shear wave is horizontally polarized with respect to waveguide major faces but is reflectively redirectable to vertical polarization with respect to pipe. The wave mode converts to longitudinal when it enters the fluid at oblique incidence within the pipe. | 1 |
| Monolithic: formed in one piece by casting; by welding a cap onto the buffer extension; folding a sheet metal preform into a cylinder and wedge; (injection) molding. Folded sheet metal can be welded together at or near the edge bounding two adjacent sheet sections of like shape and dimensions, as a step to simplify subsequent seal-welding into a slot, or to add rigidity. Rigidity can also be enhanced by adding ribs, or "flanges" at the edges, mainly outside the main beam, said flanges creating a local cross section resembling a small I-beam. We may use "monolithic" to include structures equivalent to say sheet metal cut and then re-welded, brazed or soldered back together; plastic cut and then re-joined by epoxy; machineable ceramic parts bonded together by a ceramic cement. The joint in these examples is thermomechanically similar to the adjacent materials. | 1, 1H 2A, 2B |
| Pipe material: usually steel or SS; can be plastic or other material. Plastic pipe allows use of off-diameter GC paths without the transducers penetrating the pipe, in which case flat- ended narrow reflectors, intrusive or recessed in axially-elongated slots in are preferably used to reliably reflect and thereby utilize that portion of a spreading beam that lies in the preferred GC planes. Regions of the pipe corresponding to slots may be milled part way through the wall from the outside and inside, leaving a pressure-bearing window that locates and mates with its respective transducer on the outside, and radiates into the fluid inside the pipe. In other cases the pipe can be made of sheet metal, preferably reinforced by flanges or other cutouts to maintain the sought cross section, usually round. | 2, 2F, 3, 3A, 3B, 3C |
| Piezoelements: reciprocity; multiplicity of piezoelements or standoffs. | 1A, 1E, 5, 6, 7, 7A |
| Measurement modes, electronics: various active or passive electronic interrogation or listening modes, including various differential modes. The passive modes include adding a special bluff body to a valve body or valve flange to create a characteristic noise signal whose spectrum can be analyzed to reveal flow velocity, Reynolds Number or other flow-related information. | 2C, 2D, 3B, 5, 6, 7, 8 |
| Special differential arrangements: for low cost, for fast-response electronics | 6 |
| Preferred duty cycle for highly turbulent media: interrogation recommendation when fluid is very attenuating, especially when it is more attenuating for waves transmitted against the direction of flow, vs with the flow. | 8 |
| Removability features: removability of electroacoustic transducer or excitation coil for piezoelectric or magnetostrictive transducers. | 2F, 4A, 4D |

FIG. 1 shows an elongated nondispersive directive waveguide 10 suitable for installation on a pipe, conduit or other solid body, for measuring flow, liquid presence or level, or other fluid characteristic. Installation as described below, is nonpenetrating and noninvasive, such as clamp-on, braze-on or weld-on, or a wetted mounting (penetrating the pressure boundary) but not necessarily protruding beyond the inner surface of that boundary, and where even the wetted mounting may include clamp-on or clamp-in, braze-in and weld-in. The waveguide may be removably clamped or permanently bonded to a window formed in a pipe at specific regions according to the desired paths of integration. (An illustration of this detail appears in FIG. 2F, where removable hockey stick 10 rmv is about to be clamped against window 10w.)

As shown in FIG. 1, the waveguide 10 includes an elongated buffer 12 having an ultrasonic source, namely transducer 15 coupled to one end, leading to a shoe or wedge 14 at the other end, which has an exit face 16 for launching the ultrasonic energy received from the source. The buffer propagates the energy non-dispersively as a horizontally-polarized shear wave along a straight and non-mode-converting path, while a face 18 internally redirects the energy traveling along the buffer 12 so that it strikes exit face 16 at a defined angle of incidence. A plurality of features 13 located away from the principal ray path along the buffer provide reference temperature signals of known spatial origin, allowing direct calibration of transit time in the buffer. These are illustrated in the composite schematic FIG. 1A described below. The buffer 12 and lower portion 14 will be generally referred to herein as the "handle" and "blade", by analogy to their hockey-stick shape. Both have a rectangular or plate-like cross-section of high aspect ratio. This results in a relatively large surface area of the buffer portion, making it particularly effective as a passively cooled thermal-stand-off, and results in a relatively small surface area of the edge face 16, making it an easily coupled and highly efficient emitter with a wide footprint relative to the signal wavelength in the fluid. The small area of the edge face 16 has a numerical value preferably less than about one-tenth of the square of its length. This small area minimizes heat transfer from the fluid or pipe into the stand-off. The high aspect ratio yields a wide yet directive beam in the fluid in one plane, and an initially narrow beam that exhibits greater divergence laterally.

Notably, the blade portion receives energy along oblique relatively shallow paths near the exit face 16 from the redirecting face 18. This region, bounded by face 16 which contacts the conduit may be substantially isothermal so that the ray paths from transducer to face 18 and from face 18 to face 16 are each substantially linear. The buffer 12 may be oriented generally perpendicular to the source of heat at the conduit surface so that propagation in the buffer also proceeds without refraction.

Referring still to FIG. 1, the drawing shows one commonly used form of this device. A number of early models were machined out of ¼-inch-thick carbon steel or SS (stainless steel) type 316 plate, to form a generally-hockey-stick shaped waveguide 10 having a narrow thickness x, an overall width z+w and a height y. The waveguide, which shall occasionally be referred to as a hockey stick, may be said to be comprised of a blade or foot portion 14 and an extension portion 12 joined in such a way that a reflecting surface 18 reflects without mode conversion substantially all the incoming shear waves incident upon it. The dimension w is also the approximate width at the top of the waveguide where the piezoelement 15 is mounted. That end is referred to as the piezo end. Preferred shapes for high temperature applications are those for which y>>z>>x. The height of the foot portion may be about twice w. As a numerical example in mm, x=6.4 mm, z=70 mm, y=200 mm, and w=35 mm. Early steel hockey stick waveguide models built approximately according to these dimensions utilized shear wave piezoelements 6.4-mm wide ×25.4-mm long by 0.5, 1.0 and 2.0 MHz thick. The piezo element thickness is the resonant thickness at the fundamental frequency. Preferred values for y depend primarily on the anticipated temperature range, and the thermal and acoustical properties of the material chosen for the waveguide. Waveguide materials include metals such as Ni-plated CS (carbon steel), SS (stainless steel), Ti, brass, aluminum; ceramics; plastics including polyamide-imide or phenolic plastics for high temperature, CPVC or PEEK (poly ether ether ketone) for more ordinary temperatures, and graphite or composites, for example.

The foot or blade end of the hockey stick shape provides the function of an acoustic wedge, to introduce vertically polarized shear waves at an appropriate angle of oblique incidence, generally between 35 and 70 deg, and most often 45 or 60 deg. Piezoelement 15 is a shear mode piezoelectric material such as PZT, with particle motion parallel to major surfaces of waveguide 10 and perpendicular to the shear wave path in extension 12, and dimensioned as mentioned above.

If the hockey stick were placed on top of a pipe, with its midplane parallel to the pipe axis, the angle of reflecting surface 18 makes an angle of 30 deg to the normal to the pipe, said normal being erected perpendicular to the pipe and passing through the midpoint of the bottom surface 16 of the hockey stick. That surface will sometimes be referred to herein as the radiating hypotenuse, a terminology discussed further below in connection with FIG. 1A. A shear wave coming from the piezoelement at the piezo end and striking surface 18 reflects or is guided and subsequently strikes surface 16 at an angle of incidence of 60 deg. This is known to be a desirable angle of incidence, for obtaining ultrasonic flow measurements by clamp-on contrapropagation applied to liquids in many standard carbon steel or SS pipes.

For electrical shielding and optionally for providing a connection means for conduit, where conduit is used to protect coaxial or other cabling means that runs from the transducer to the electronics, the top end of the hockey stick is terminated in a SS316 eternally-pipe-threaded adapter cap. A standard BNC or other electrical connector is installed at the end of that adapter cap. A short electrical lead wire, not shown, connects from a terminal on the electrical connector to the ungrounded electroded side of the piezoelement 15. The cap is typically fillet-welded to seal around the top of the hockey stick's extension 12, before the piezoelement is installed. Applicant has found that welding around that joint does not degrade the ultrasonic shear waves guided within and through that welded region. If a conduit connection is not necessary, the external pipe thread can be deleted, and the adapter cap is simplified to a standard one-inch 3000# SS316 cap, for example. The cap is oblong-slotted at one end to match the waveguide cross-section to which it is subsequently welded. A standard one-inch SS316 hex head plug is then threaded into the cap. The plug is tapped at its hex head end to accept the BNC or other electrical connector.

The cap region in preferred designs remains relatively cool, under 125° C., even though the opposite end is coupled to a hot pipe at temperature, T≧260° C. The cool end ensures that the electrical properties of the piezoelement and adjacent bonds or electrical tuning elements, e.g., an inductor, remain substantially constant. In one embodiment a thermoelectric cooler is installed within the cap (202TE in FIG. 1I), to further limit the temperature excursions of the piezo or electrical elements. By means of simple and known feedback control, the thermoelectric cooler turns on only if the cap region thermocouple senses that the cap temperature reached a T setpoint, for example, 99° C. The cooler then runs until the cap T drops, e.g. to 95° C. By this means the electrical properties of both transducers (in a typical two-transducer contrapropagation path) can be maintained nearly identical, and thereby minimize any flow measurement errors that might otherwise occur due to thermally induced nonreciprocity.

At a point vertically in line with the center of the radiating hypotenuse 16 and above the beam reflected off surface 18, a hole 17 of about 12.7-mm diameter is drilled through the foot 14. This serves several purposes. During manufacture it holds the stock in place, for machining. In application it provides a place to apply high coupling pressure, ~1000 psi or more. It also locates the clamp-on version within a yoke having a corresponding hole, as illustrated in FIGS. 3A and 3B, below.

Above the hole, on the surface opposite the radiating hypotenuse, there is a small drill point or indent 17a, which is another point for application of coupling pressure, or for alignment.

Another topological feature, introduced as a timing reference reflector, is the small shallow groove 17b which is oriented parallel to the shear wavefronts incident upon it. Its reflecting edge begins where the hole centerline intersects the bottom surface 16. This groove, about ¼- to ½-mm deep, and 3-mm wide, is positioned so the time for the shear wave to travel along the path centerline from the piezoelement 15 to the groove 17b and back to the piezoelement 15, and denoted $t_w$, is indeed the time it would take for ultrasound to travel along the centerline path between two piezoelements, if their identical hockey sticks were butted at the radiating hypotenuse ends and with point symmetry about the centerlines of aligned hole(s) 17. Another hole (of which two examples are shown in FIG. 1B) can be drilled or otherwise machined parallel to hole 17, through approximately the midpoint of the shallow groove, to increase the amplitude of the $t_w$ reference echo.

This "$t_w$ hole" may be round or square and would typically be approximately the same size as the width of the shallow groove 17b, namely, about 3 mm in the present example. Only a small percentage of the shear energy reflected off the surface 18 is reflected by the shallow groove. Most of the energy reflecting internally off the bottom 16 bounces off the end surface which may be rounded to scatter this energy. However, a relatively strong end echo may nevertheless be detectable by the piezoelement 15, and its arrival time after the $t_w$ echo can be interpreted in terms of sound speed and temperature in the foot 14. The ratio of amplitudes of the two echo signals, from the groove or hole and from the rounded end, is a normalized measure of the coupling efficiency into the adjacent medium to which the radiation is directed. The amplitude of the groove echo also is a measure of the electroacoustic strength of the piezoelement (k31) and the attenuation along the path in the waveguide. Ringdown in the waveguide, however, may also be used as a measure of waveguide attenuation. At all events, these echo signals provide reference points for correcting time or amplitude values of measurements and protocols in the system.

A weld bead may optionally be provided as a shallow bead whose end nearest the bottom ends rather precisely, achieved by machining, at a height appropriate to the depth that the bottom portion 14 is to be inserted into a slot. This simplifies weld-in installation. This same function is achievable by thinning one or both sides of the foot by 0.005 inches per side to the appropriate height, or by center punching at that height.

Several rounded tabs 13 are shown projecting outward from the right-side bounding surface of extension 12. That surface preferably is rounded to scatter ultrasound incident thereon, just like the end surface 18a drawn parallel to reflecting surface 18 (FIG. 1). The rounded tabs are alongside yet out of the main beam, so each can be tapped e.g. #8–32 for installation of a short (³⁄₁₆-inch length) standard panhead SS screw to hold thermocouples or other temperature sensing devices. In high temperature applications this is useful to keep track of the temperature distribution along the extension. A similar blind threaded hole can be tapped in the cap, to attach a thermocouple there to monitor that the cap region does not exceed say 100 deg C. Referring again to the rounded surface, note that while it runs generally parallel to the flat edge surface between reflecting surface 18 and the piezo end, its contour creates asymmetrical boundary conditions with respect to the beam centerline path. This helps discourage interfering multipath propagation.

Parts made essentially according to this description have been pressure-coupled to 10-inch schedule 40 SS pipe using a yoke and clamp arrangement similar in part to the clamps sold by Panametrics, Inc. under their registered SONOC-LAMP trademark, as described in U.S. Pat. No. 4,286,470 (September 1981), and with Cu, Sn or other couplants, or no couplant at all, between the radiating hypotenuse and the pipe. Other parts, similarly made, were welded onto the outside of another 10-inch schedule 40 SS pipe. Fillet welds on each side of the radiating face melted enough of the radiating hypotenuse (bottom face 16) region to provide nearly 100% bonding. This demonstrates one of the advantages of the thin blade (only ~6-mm thick) . . . it is easy to obtain a full penetration weld, only ~3 mm penetration needed on each side, in the weld-on version of clamp-on. This small a weld means virtually no distortion of the pipe, whose wall thickness was 9 mm. The long extension kept the transducer (piezo) end cool despite welding at the radiating end. Still other hockey sticks have been welded into oblong slots in a spoolpiece, as will be explained in connection with FIGS. 2 and 3.

Figure 1A:
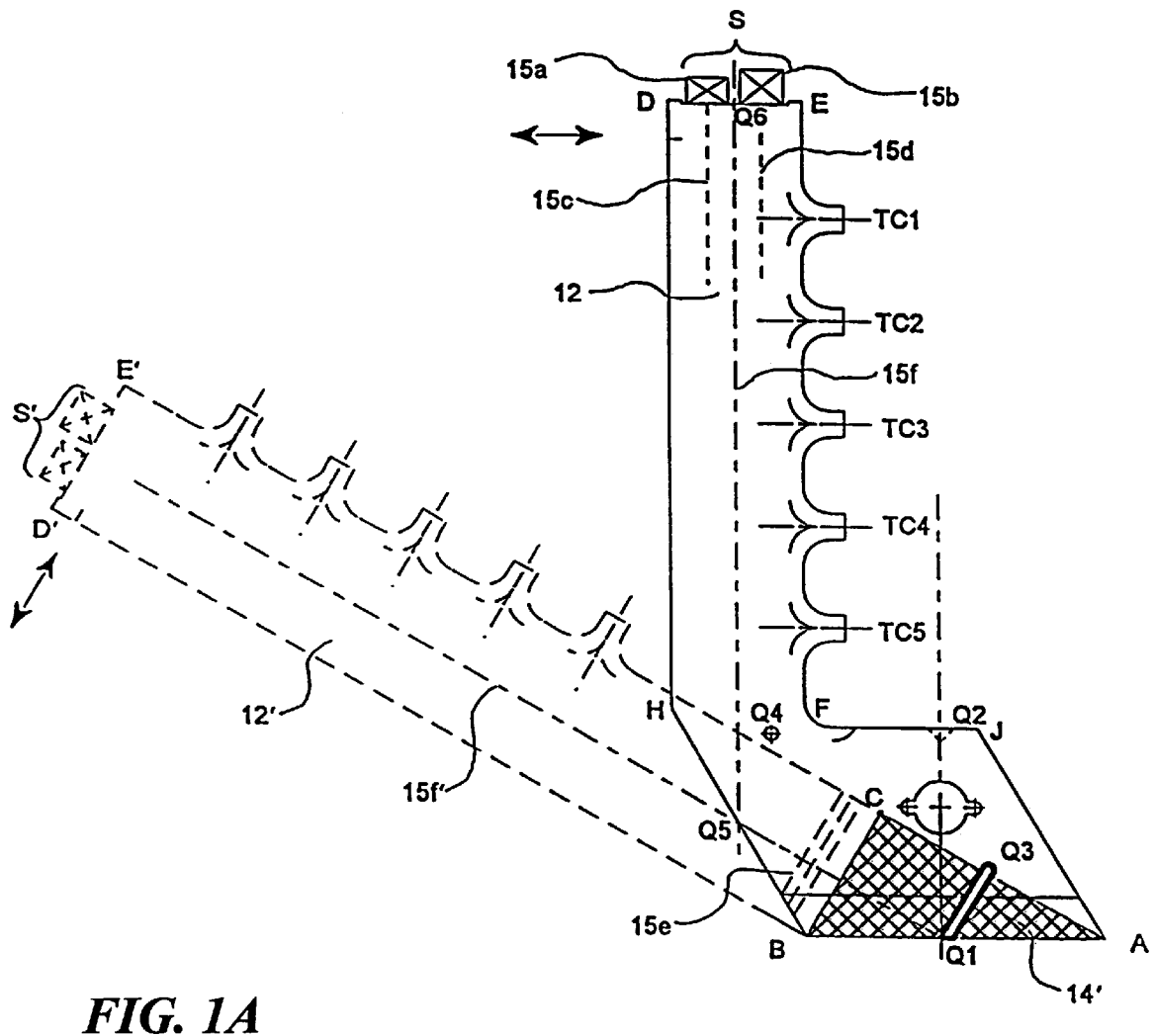
FIG. 1A shows another embodiment similar to that of FIG. 1, having a piezoelectric element of multi-element construction schematically divided into a combination of a waveguiding triangular wedge foot portion, and a polygon-bounded waveguiding extension to the piezomaterial.

FIG. 1A shows a composite schematic view of a waveguide similar to that of FIG. 1, except that the piezoelectric element is shown in the form of a multi-element construction 15a, 15b. This is done to achieve ease of fabrication, or for multi-frequency operation, or for creating a wide beam within one sensor, leading to a large aperture at the radiating surface 16. Lettered points indicate important vertices and other important points along the ultrasonic path. The device can be understood to be a combination of a waveguiding triangular wedge portion 14' in the foot of the device indicated by letters A, B, C, and a polygon-bounded waveguiding extension 12 delineated by letters BHDEFC which extends outward to where the piezomaterial is located. The phantom buffer BCE'D' illustrates the "virtual" position of the buffer with respect to the reflective face 18 centered at principal reflection point Q5. In another embodiment the extension portion may actually occupy the position indicated by 12', so that the entire waveguide provides a straight path to the exit face. In this case the edge along side D'B guides but does not deflect the energy. In general, the invention contemplates that the extension portion may occupy a number of different angular orientations when used in an embodiment that guides wave energy to a redirecting face, and the angle may be selected based on the desired angle of incidence at the exit face for the conduit or the fluid/velocity involved.

FIG. 1A also illustrates the right triangle wedge ABC (shaded) and a waveguiding polygonal extension generally defined by or including points CBDE, together with certain topological features for sensing or controlling shear-wave transducer position, shear-wave propagation, and positioning or coupling the assembly on an adjacent pipe. Leg BC of the wedge is parallel the incoming shear wavefronts 15e. The transducer S is a source (or receiver) of horizontally polarized shear waves having particle motion (indicated by a double-ended arrow) perpendicular to the path and parallel to the first and second major faces ABHDEFJA and AA . . . JJ,AA. (Double letters refer to the corresponding vertces on the hidden parallel second major face.) Topological features are formed in the waveguide. These preferably include a small blind hole reflector at Q4. The hole at Q4 is drawn under and approximately tangent to the plane that is perpendicular to Q1Q2 that passes through Q2. Another topological feature is the small $t_w$ reference reflecting groove which is drawn as a shallow slot between Q1 and Q3. The term $t_w$ is the round-trip transit time along the centerline path between S and Q1. This groove is oriented parallel to the incoming shear wavefronts 15e. In the standoff 12, shear ray paths are drawn as dashed line segments 15c,d parallel to standoff centerline 15f. Optional projections TC1, . . . TC5 may be formed in the body 12 as small tapped tabs alongside the signal propagation path but more or less out of the way of the main beam. Their purpose is for attaching thermocouple, resistance temperature detector or other temperature-sensing means, from which the temperature distribution and the corresponding sound speed distribution along the path may be determined. In one embodiment, by intentionally drilling the tap drill holes extra deep and thus slightly into the path of the main beam, reference echoes are generated along the standoff.

In another embodiment, the triangular wedge region ABC may be filled with a material having special waveguide properties needed adjacent the radiating hypotenuse edge AB. For example, in one embodiment an assembly mostly made of SS316, and having a shear-wave velocity of about 3100 m/s, has a cavity of width about 90% of the thickness X1, milled, cast or otherwise formed in the ABC region. This cavity is then filled with silver (Ag) or other material to provide a much lower vertically polarized shear-wave sound velocity (1610 m/s) at the angle of incidence appropriate to radiating at a large refracted angle $\theta_3$ into an adjacent fluid, when the assembly is used as a "wetted" transducer. Energy enters the filled region at normal incidence at face BC, and its sound speed is reduced. By making only the ABC cavity region of silver, the overall cost of the assembly is kept within reasonable bounds.

As noted above in connection with FIG. 1A, the hockey stick construction of the present invention may operate at several frequencies. It is a broadband waveguide. Two (or more) piezoelements could be installed at one end, and launch, for example, pulses having quite different center frequencies such as 0.5 and 1 or 1 and 2 MHz. These pulses may be launched simultaneously or sequentially, and will propagate toward the radiating hypotenuse along the thin blade at the shear wave phase velocity, about 3100 m/s for the commonly used 300-series alloys of stainless steel. In a smaller-dimensioned hockey stick waveguide one may launch pulses having center frequencies of 2 and 4 MHz in some sequence, e.g., alternately frequency hopping from one frequency to the other and then back again.

Another modulation scheme contemplated with these waveguides is to simultaneously amplitude-modulate each of two frequencies according to the square of a sine or cosine function, respectively. This can produce a composite wave which, at the start, could be 100 percent formed of the lower frequency component (say 2 MHz). The amplitude of this component then diminishes from an initial value down to zero according to a cosine squared envelope over signal interval, e.g., five microseconds corresponding, by way of example to $\pi/4$. During this same five microsecond interval, the higher frequency component (say 4 MHz) builds up according to the square of the sin of the same argument. Note that the sum of the envelopes is a constant, since $\sin^2\theta + \cos^2\theta = 1$. This method of frequency modulation yields a chirped signal whose periods vary unambiguously from cycle to cycle. Since these waves of different frequencies are of small amplitude they can propagate simultaneously over the same path or side by side in the hockey stick, at the nondispersive phase velocity mentioned above, e.g., 3100 m/s.

FIG. 1B is a conceptual drawing showing the range of angles that the extension or leg portion 12 can make relative to the wedge or foot portion 14. The foot is coupled through or to the outside of the pipe wall W to project a signal through fluid F. The shallow reflecting groove 17' is shown across the incoming wave path to reflect a reference signal back up the standoff portion, and an alternative or additional round through hole 17rdh or square hole 17sqh are shown. These may augment the amplitude of reflected energy, or may be used separately instead of a groove. The leading edge of these holes is positioned tangent to the leading edge of the shallow groove.

Figure 1C:
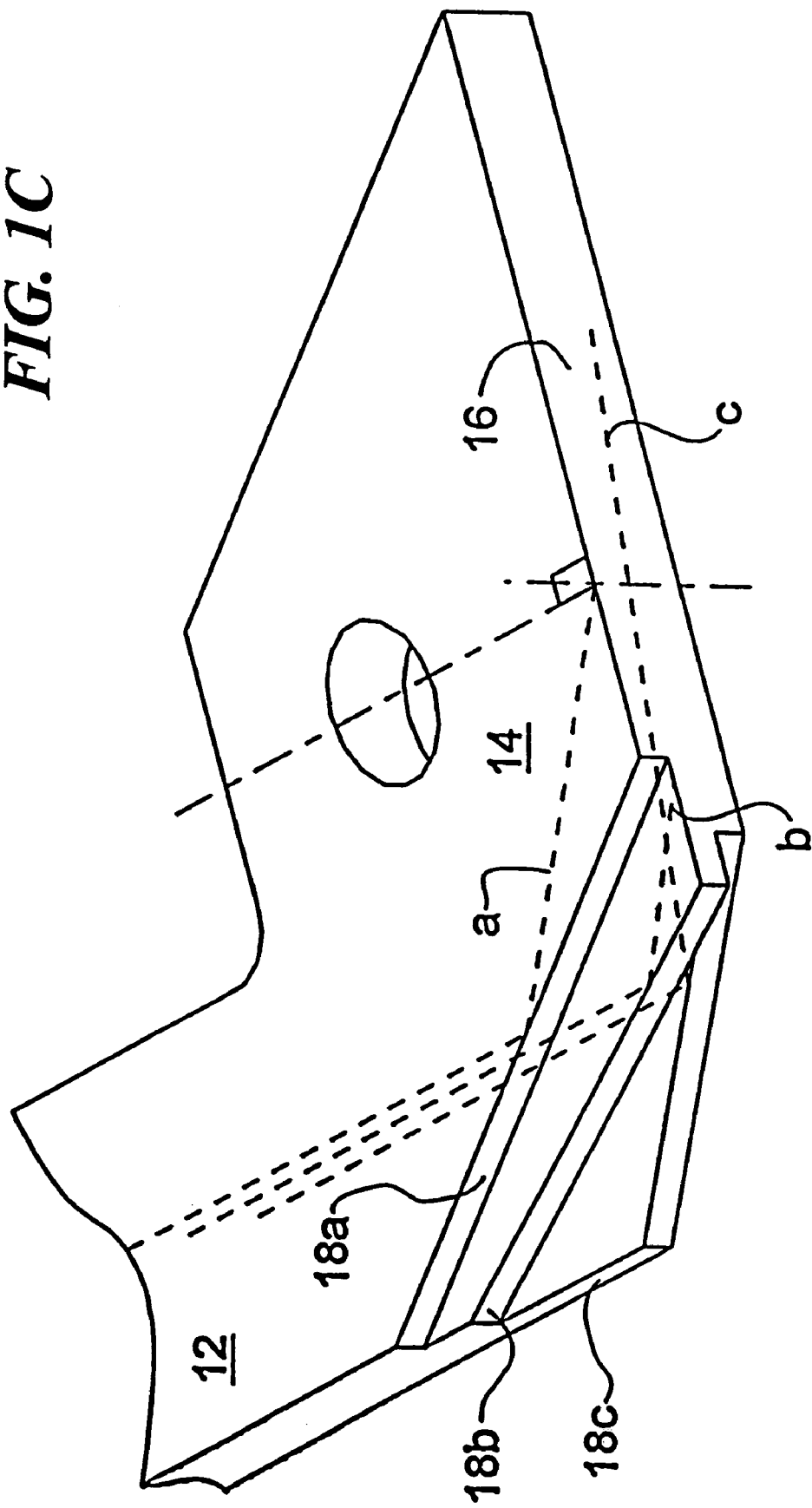
FIG. 1C shows a multi-angle embodiment in which three angles of incidence are provided in a single waveguide sensor.

FIG. 1C shows details of a multi-angle construction in which the redirecting face 18 is stepped to provide three different faces 18a, 18b, 18c reflecting rays a,b,c at three angles of incidence in a single waveguide sensor. This introduces the shear wave at different angles of incidence, in anticipation of different fluid sound speeds, which may for example compensate for such differences and yield particular angles of refraction. Another use of this feature is to create a plurality of precisely-defined beams a,b,c which intersect in the fluid, to make reflection-mode measurements, for example, when the fluid is of a scattering nature.

Figure 1D:
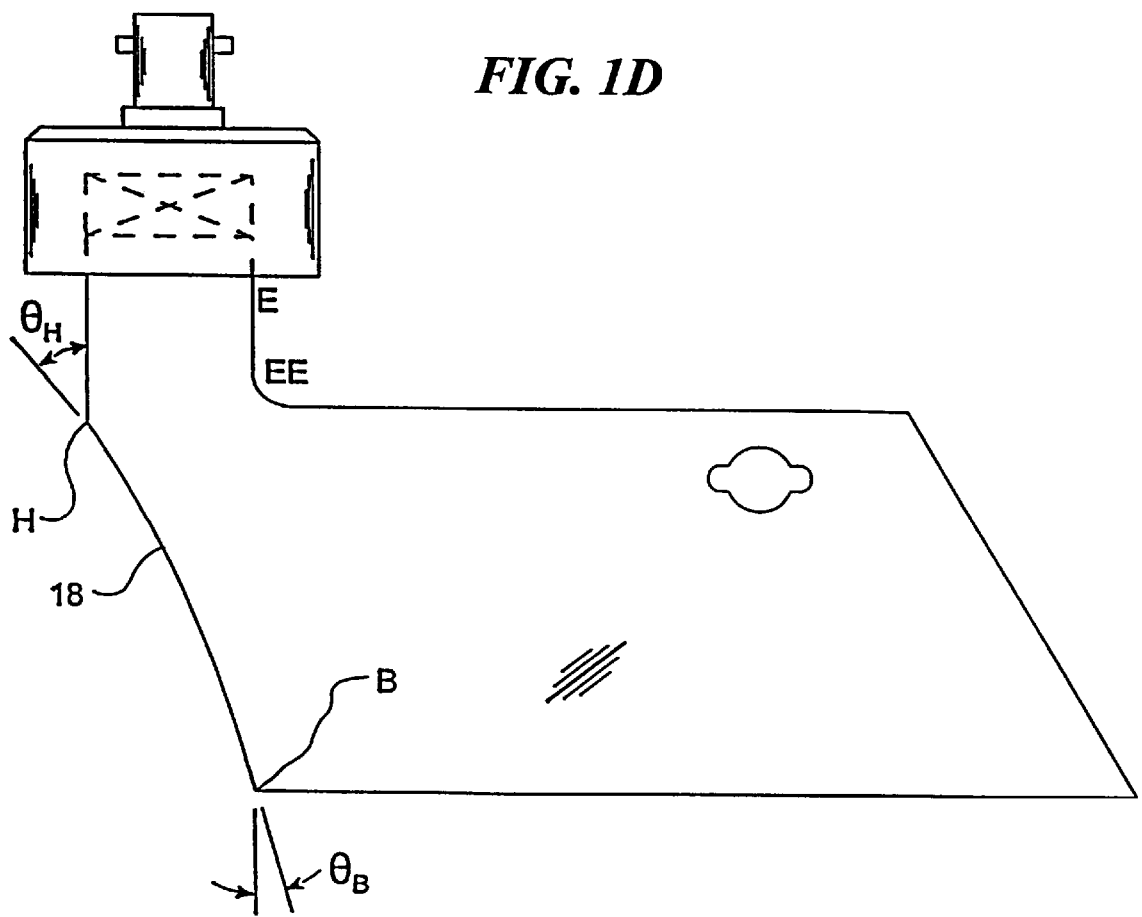
FIG. 1D shows another multi-angle construction in which a curved reflecting surface generates a continuum multiplicity of angles of shear-wave incidence.

FIG. 1D shows another multi-angle construction in which the reflecting surface 18 is a curved reflecting surface that generates a continuum multiplicity of angles of shear-wave incidence $\theta_1$ from 30° to 80°. The angles between the vertical and the tangents to the curved reflecting surface range, respectively, between $\theta_B=15°$ and $\theta_H=40°$, i.e., half the sought angle of incidence. Point B, corresponding to point B in FIG. 1A, is at the bottom, on the extension of line E-EE. This means E-EE-B is a straight line.

Figure 1E:
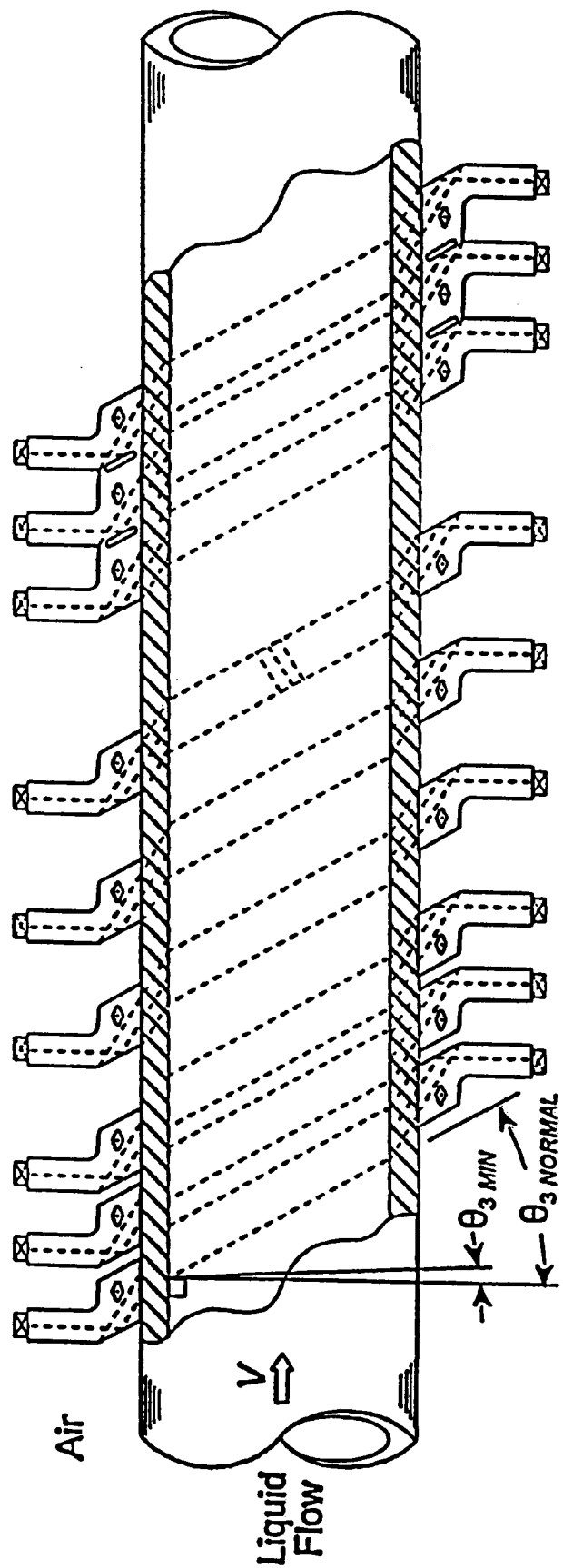
FIG. 1E shows a system wherein a plurality of identical waveguides are placed in a row to increase the system tolerance to a wide and unpredictable range in sound speeds in the fluid, and to increase the aperture.

FIG. 1E shows a plurality of n identical waveguides placed in a row to increase the system tolerance to a wide and unpredictable range in sound speeds in the fluid. This also increases the aperture by at least n times, according to the gap between them being zero to the order of the radiator length X4, i.e. the length of the exit face 16. The illustrated mounting of identical waveguides at top and bottom positions as transmitters and receivers exploits the reciprocity capability of piezo transducers. That is, each piezoelectric element can be used as a transmitter, or a receiver, or serve both functions in alternation, effectively transducing (i.e., transforming) vibrational to electrical signal energy in either direction. The magnetostrictive transducers discussed below with respect to FIG. 4D are also reciprocal (send/receive) devices. At the right is shown a monolithic assembly in which a single body has three standoffs each holding one or more transducers.

Figure 1F:
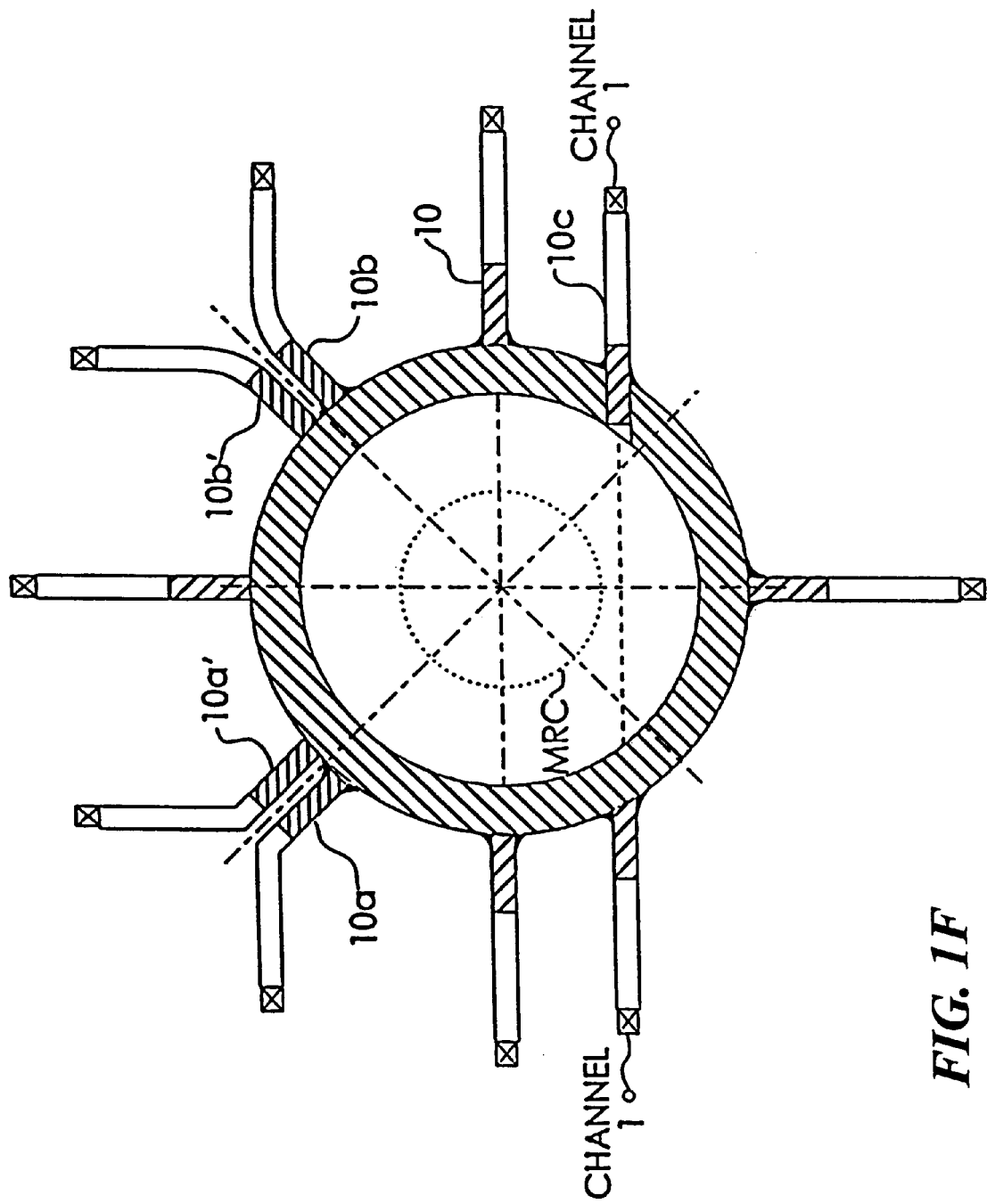
FIG. 1F shows an embodiment where the buffer joins the blade to form nonplanar curved and sharply bent waveguides.

FIG. 1F shows a spoolpiece in which a plurality of waveguides in accordance with the invention are attached to interrogate various chordal or diametral paths. These include waveguides which are sharply bent and welded 10a or clamped 10a' to the pipe, waveguides which are gently curved and either welded or clamped 10b, 10b', straight, i.e. planar, waveguides 10, and penetrating waveguides 10c for directly launching a signal along a direction into the fluid. The midradius circle MRC is shown at a radius equal to half the inside radius of the pipe.

Figure 1G:
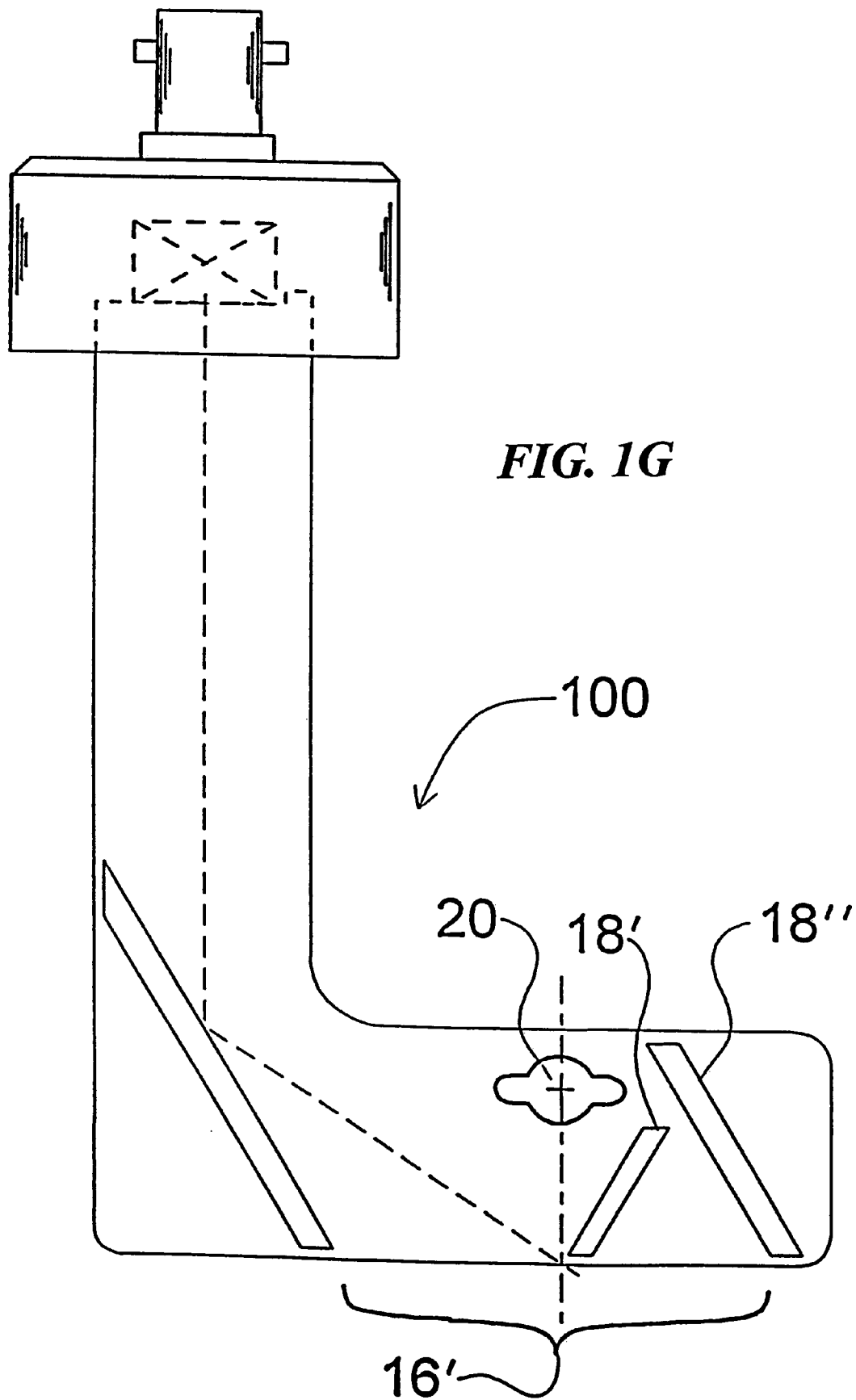
FIG. 1G shows a waveguide embodiment in which primary and secondary reflecting surfaces are protected against fouling to reduce exposure to debris.

FIG. 1G shows a waveguide 100 in which secondary reflectors 18', 18" limit the active length 16' of the exit face 16, and the primary and secondary reflecting surfaces are protected against fouling by covering, concealing or otherwise reducing their exposure to possible sources of debris. Elongated angled quadrilateral slots may form reflective cavities only part way into the sheet to form these faces. The hole 20 goes through. The "toe" and "heel" of the foot portion can be parallel. This makes it easy to fit to and install into a slot similar to those in the wetted versions (e.g., FIG. 1F, transducer assembly 10c, or the devices of FIGS. 3, 3A or 3B.

Figure 1H:
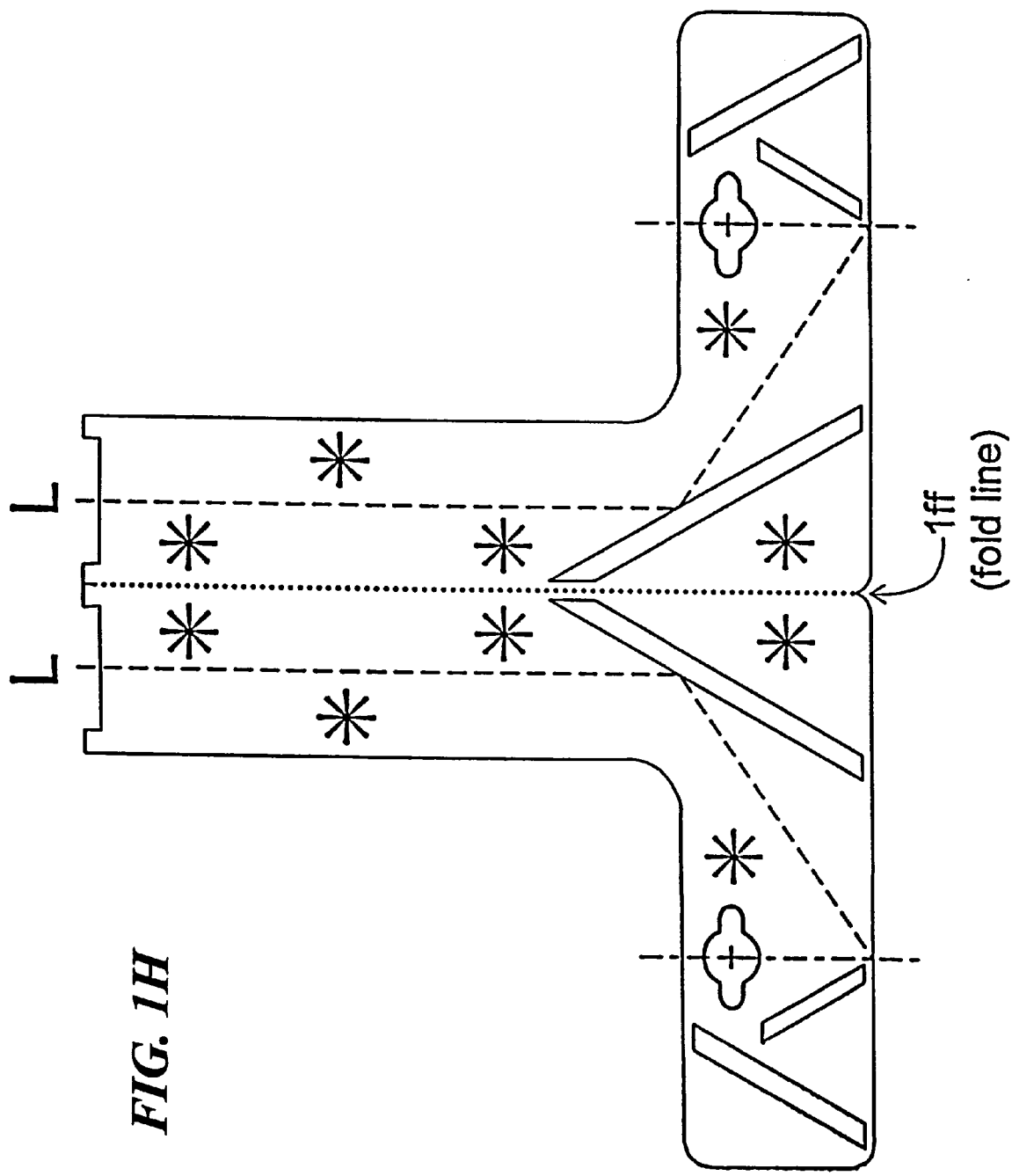
FIG. 1H shows a sheet metal stamping having first and second faces, in which half-cavities are formed on the first face in a pattern symmetrical about a fold centerline, such that after folding sharply about that centerline through an angle of 180°, the half-cavities become adjacent as the two halves of the first face touch one another, and thereby provide shielded reflecting surfaces functionally similar to those in FIG. 1G, invisible from the second face, which now bounds the folded configuration.

FIG. 1H shows a sheet-metal stamping to implement the embodiment of FIG. 1G. The stamping has first and second faces parallel to the plane of the drawing, in which half-cavities can be formed illustratively on a first face in a pattern symmetrical about a fold centerline, such that after folding sharply about that centerline through an angle of 180°, the half-cavities become adjacent as the two halves of the first face touch one another, and thereby provide shielded reflecting surfaces functionally similar to those in FIG. 1G, invisible from the second face, which now forms the outer surface and bounds the folded configuration. The resulting external seam can be welded shut. The two adjacent halves can be spot welded together at various points (denoted by asterisks) outside the ray paths indicated by lines L, L'.

Figure 1I:
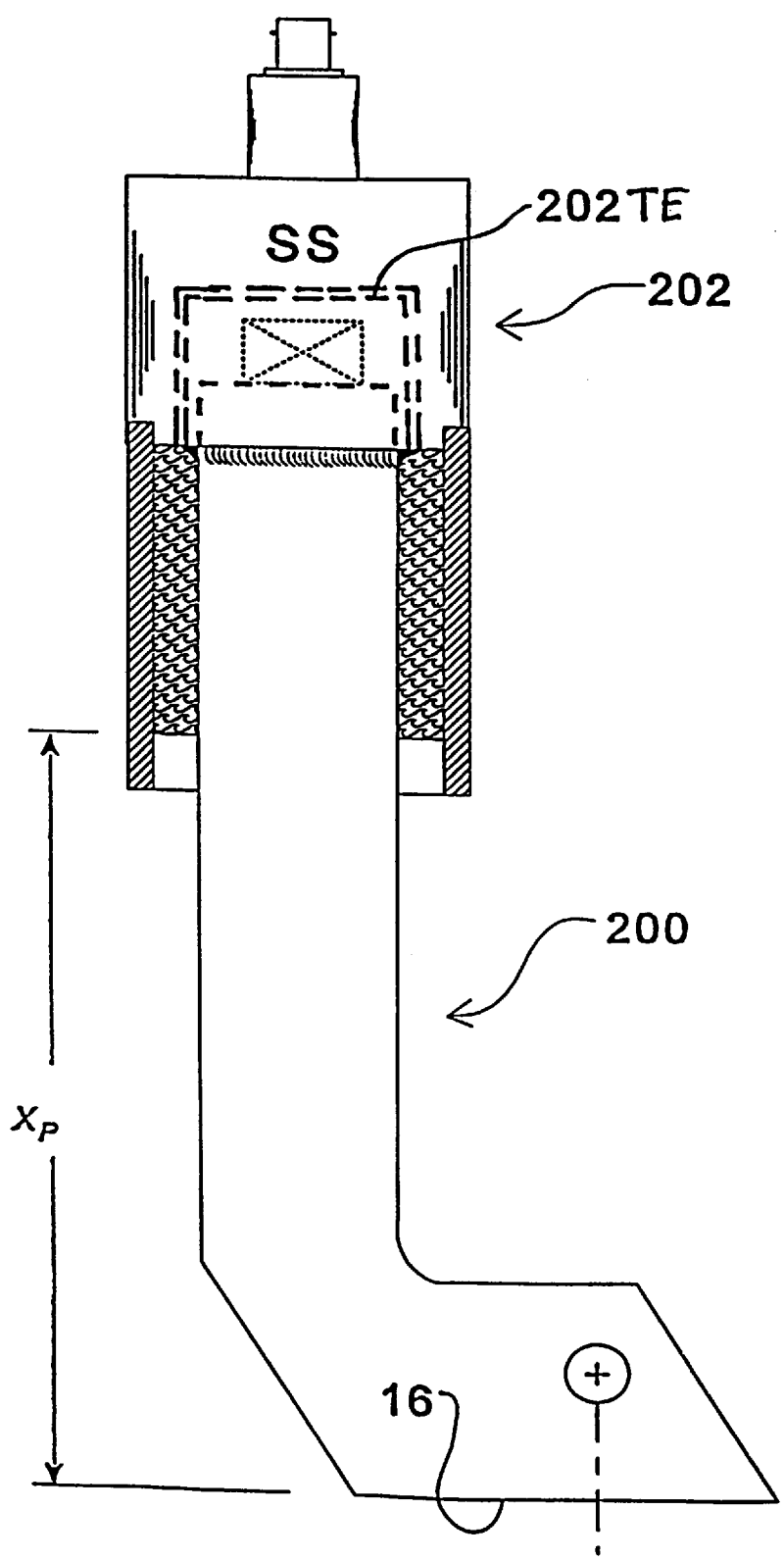
FIG. 1I illustrates an embodiment with attenuative potting near a capped end to damp reverberations therein.

FIG. 1I illustrates a sectional view through a waveguide 200 of the present invention, in which a cap assembly 202 at the transducer end covers attenuative potting such as tungsten-loaded epoxy to damp reverberations near the capped end of a buffer. The distance from the radiating hypotenuse 16 to the potting, $X_p$, is about equal to buffer length X3 minus buffer width X2. Thus, both the transducer (shown in phantom) and the potting material are buffered from the hot conduit.

Figure 1J:
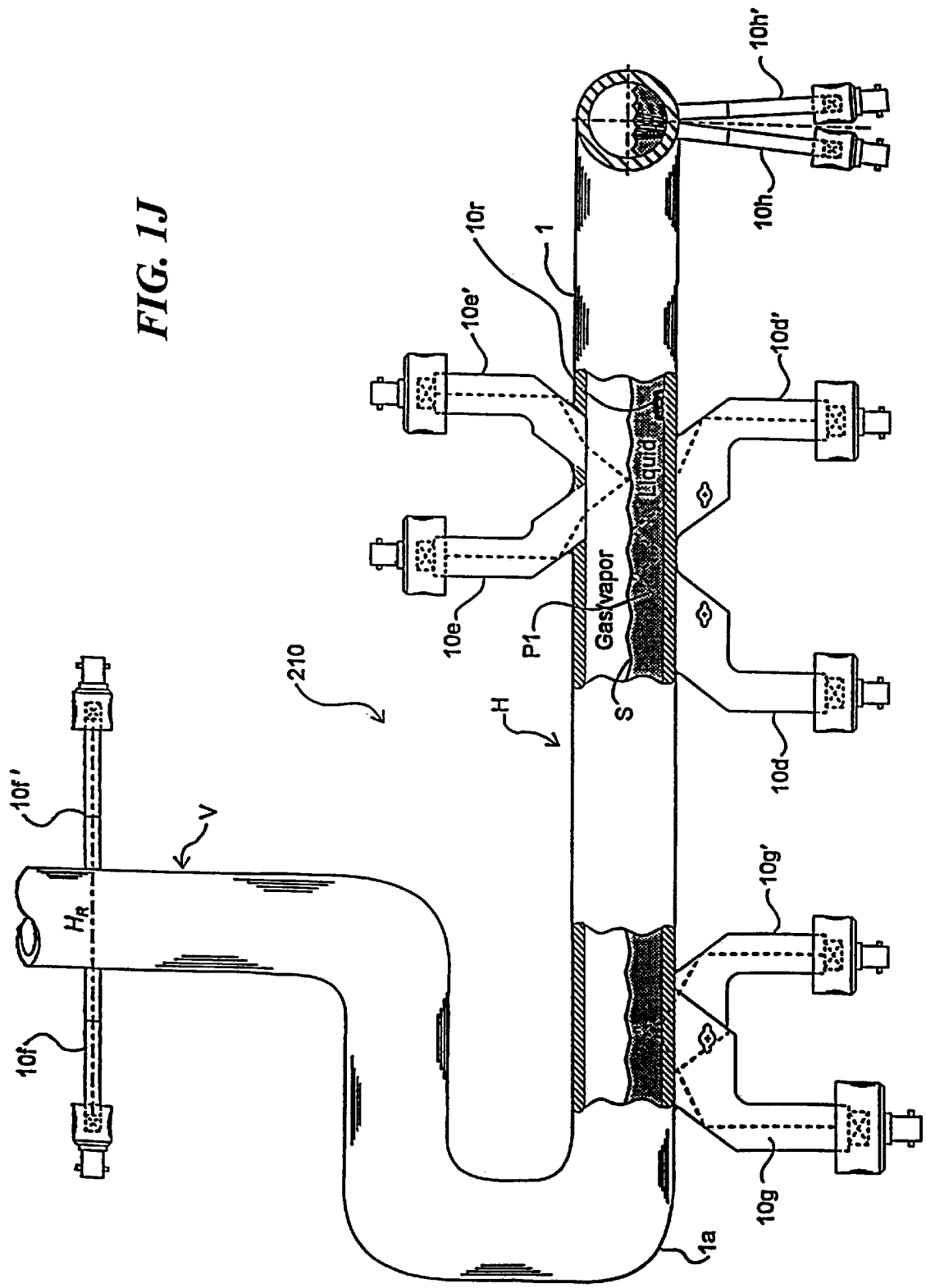
FIG. 1J shows system having a combination of waveguides of the invention at five locations on a pipe.

FIG. 1J shows a representative system 210 employing a combination of waveguides at five locations on a pipe 1. The pipe 1 has a horizontal section and a vertical riser section V connected thereto by a swept elbow 1a. The horizontal section of pipe is shown in partial section showing a conduit only partly full of liquid. A pair of weld-on waveguides 10d and 10d' are welded at a first location underneath the pipe. A residue 10r may be present on the bottom of the pipe. When the residue 10r is absent and the liquid is relatively clean, one may expect to be able to measure the liquid level by timing the echo from the liquid surface S, provided one has a reasonable estimate of the sound speed in the liquid. If there is much residue, it may be more accurate and more reliable to measure the position of the surface S by interrogating from above by means of a pair of waveguides 10e and 10e'.

At other times, the horizontal section H may be full and the liquid may rise into the vertical riser section V. To measure the level at a point denoted $H_R$ a third pair of waveguides are clamped in a horizontal plane, i.e., the waveguides 10f, 10f' are clamped on the side of the riser in a plane perpendicular to the axis of the pipe in that region. These waveguides may be variously oriented according to whether they are to sense propagation of a zigzag shear wave in the wall according to a method explained in Lynnworth, Seger and Bradshaw, U.S. Pat. No. 4,320,659 (Mar. 23, 1982), or are to sense along a chordal path.

A valid measurement of liquid level in FIG. 1J is straightforward if one has a reasonable estimate of sound speed c in the liquid. More generally to cover the case where c is not known, applicant utilizes multipaths having liquid endpoints either at the pipe ID or at the radiating hypotenuse of a wetted hockey stick, or both.

The basic idea is to interrogate the liquid surface using acoustic paths which differ in length in the liquid, where the difference in path lengths is known or calculable from the geometry of the pipe and the transducer properties and locations. Then one solves for the two unknowns, sound speed c and liquid level H, based on transit times $t_{P1}$ and $t_{P2}$ measured over two independent paths P1 and P2. The difference in path lengths ΔP, divided by the difference in transit times $\Delta t = t_{P1} - t_{P2}$, yields c. Then c times each transit time yields the liquid distance along the corresponding vee path to the liquid surface and then to the receiving transducer. The path is refracted where the ultrasonic wave enters and leaves the liquid, but this minor complication is dealt with using Snell's Law. The speed of sound in the hockey stick is determined from the material, e.g. 3200 m/s for 316SS near room temperature, or if desired, by timing echoes from the reference notch to the free end parallel to that notch and spaced a known distance away, e.g., 25 mm.

Liquid presence at particular levels can be determined from the presence of a signal when the waveguides are placed at appropriate axial or circumferential positions.

Figure 3:
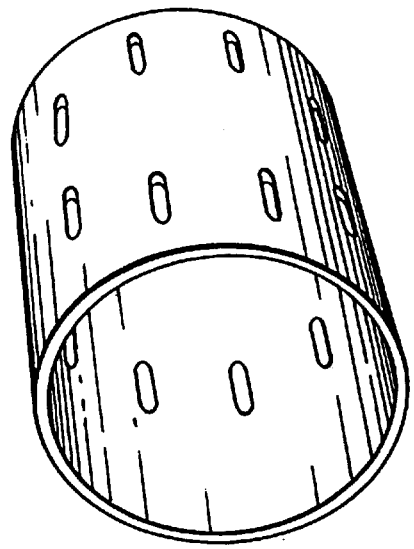
FIG. 3 is a perspective view showing outside of the front, and inside of part of the back, of a Gauss-Chebyshev (GC) multipath flowcell in which off-diameter chordal measurements are made in well-defined symmetrically-located inboard and outboard planes using eight waveguides as shown in FIG. 1 welded in a minimally-intrusive manner into narrow oblong slots all on one (front) side of the spoolpiece.
Figure 3A:
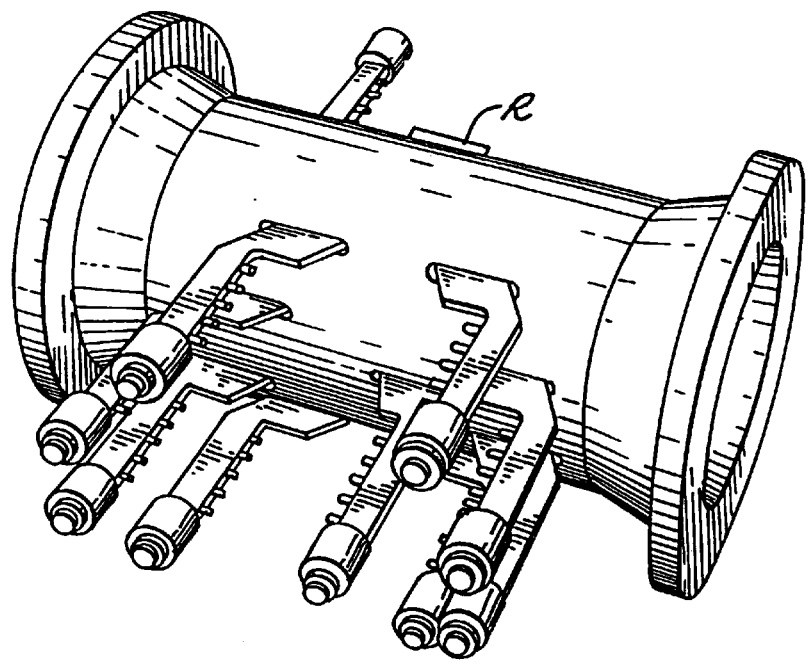
FIG. 3A is a corner view of the spoolpiece of FIG. 3, more clearly showing four reflectors mounted in the wall opposite the transducers and in their planes.
Figure 3B:
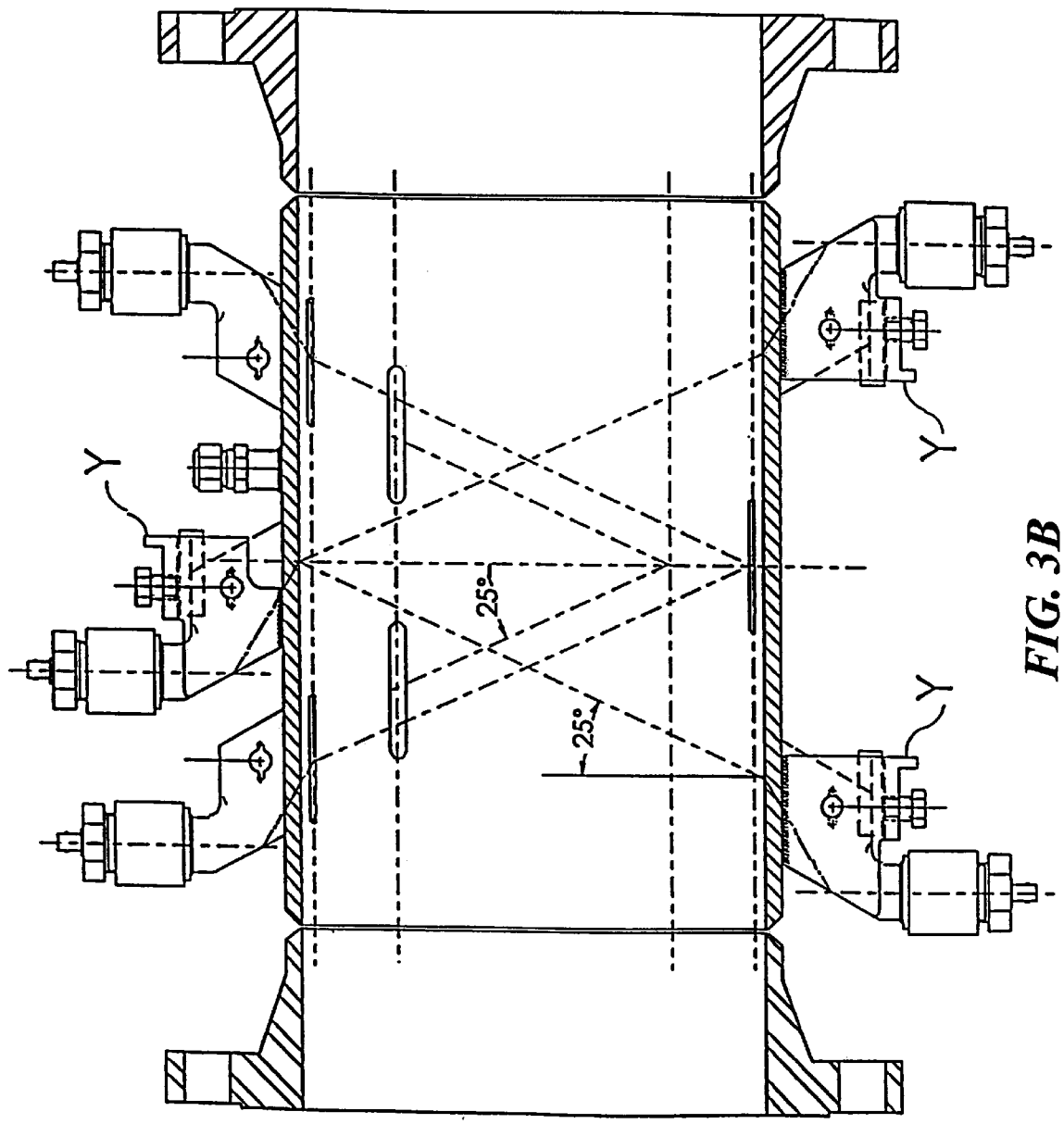
FIG. 3B shows a partly sectioned side view of a GC spoolpiece showing several clamped-on transducers at the top and bottom.

The GC spoolpiece of FIGS. 3, 3A or 3B may be seen as a specific example of how to use different paths whose path difference is very well defined, to measure H when c is unknown. As long as the liquid level H is within the common beams, then one can execute a first measurement of the transit time over a vee path between inboard upstream and downstream transducers; then between outboard upstream and downstream transducers. One can additionally execute further measurements between upstream and downstream clamp-on transducers at or near the pipe bottom, said clamp-on transducers having appropriate spacings achieved via side-by-side arrangements or via different axial spacing as indicated in FIG. 1E. It will be understood that once c has been determined, at a given temperature T, its value at other temperatures is often calculable from subsequent measurements of T, as long as composition is substantially the same at the two different temperatures. This means once c is known, the liquid surface needs to reflect only one beam from one transducer to another; the differential path is no longer required. This reduces the complexity back to the initial discussion of liquid level measured by a single pair of hockey sticks, in FIG. 1J.

According to this aspect of the invention, one solves for c, H and then, from the difference in transit times upstream minus downstream, the flow velocity V Still referring to FIG. 1J, to accommodate such measurements there are provided at the left and right ends of the horizontal run of pipe, an additional set of side-by side waveguides 10h, 10h', and an overlapped arrangement of waveguides 10g, 10g' of the present invention. These views are related to the ones in FIG. 1F. The axial spacing and exit angles of the two different waveguide pieces 10d, 10d' and 10g, 10g' provide two fluid paths P1 and P2 of differing length for determining c as described above, illustrated with reflection or double-reflection paths off the fluid surface. The waveguides may be circumferentially adjacent, or axially adjacent with a slight circumferential offset, and still effectively utilize the illustrated sending/receiving paths due to the directional but spreading beam that emanates into the fluid on either side of the central plane of each wedge portion. It will be understood that the long radiating hypotenuse yields a directive beam in the fluid or adjacent solid in the end-fire sense. This means the beam spread is relatively small about the refracted angle $\theta_3$ calculated by Snell's Law, for the obliquely incident shear wave. However, a consequence of the thin hockey stick, is that there will be much larger beam spread side to side. This is used to advantage in the side to side arrangements. Even though the two side by side hockey sticks do not appear to be pointing at the same fluid element, their beams overlap sufficiently so that a common region can be interrogated. In the present figure, the variable liquid level provides a reflecting surface within the common beams. In two-phase fluids, the scatterers can be detected by two side-by-side hockey stick assemblies, both of which point in the same general direction, e.g., into the flow.

A further consequence of the spreading beam about the hockey stick midplane, is that even members of a pair that are not side-by-side but are somewhat separated circumferentially, can nevertheless communicate with one another. For example, skipping ahead briefly to the circumferentially spaced assemblies shown in FIG. 3A, below, and implied in FIG. 3C, there is detectable and usable signal between what we will call out-of-plane transducers. This communication can be via scatterers or via reflection from the opposite wall, or via direct transmission if transducer assemblies are positioned on opposite sides of the pipe. What this amounts to is a new way of providing with only a few transducers, a large number of interrogation paths. For a numerical example, and referring to the illustration of a GC vee-path flowcell (FIG. 3C), the principal axially-oriented slots may be denoted A and AA, utilizing reflector $R_A$ slots B and BB using their reflector $R_B$, etc. But now a transducer installed at A can communicate with not only AA but also BB, CC and DD. This provides a way to cat scan the flow profile and image the flow by tomographic reconstruction. Similar remarks apply to reflection mode measurements. A pulse transmitted into the fluid by A can be received at a number of receiving sites B, C, or D, as well as back at A. Thus the invention provides new and useful opportunities for additional interrogation paths in a multi-plane spool-piece.

Figure 1K:
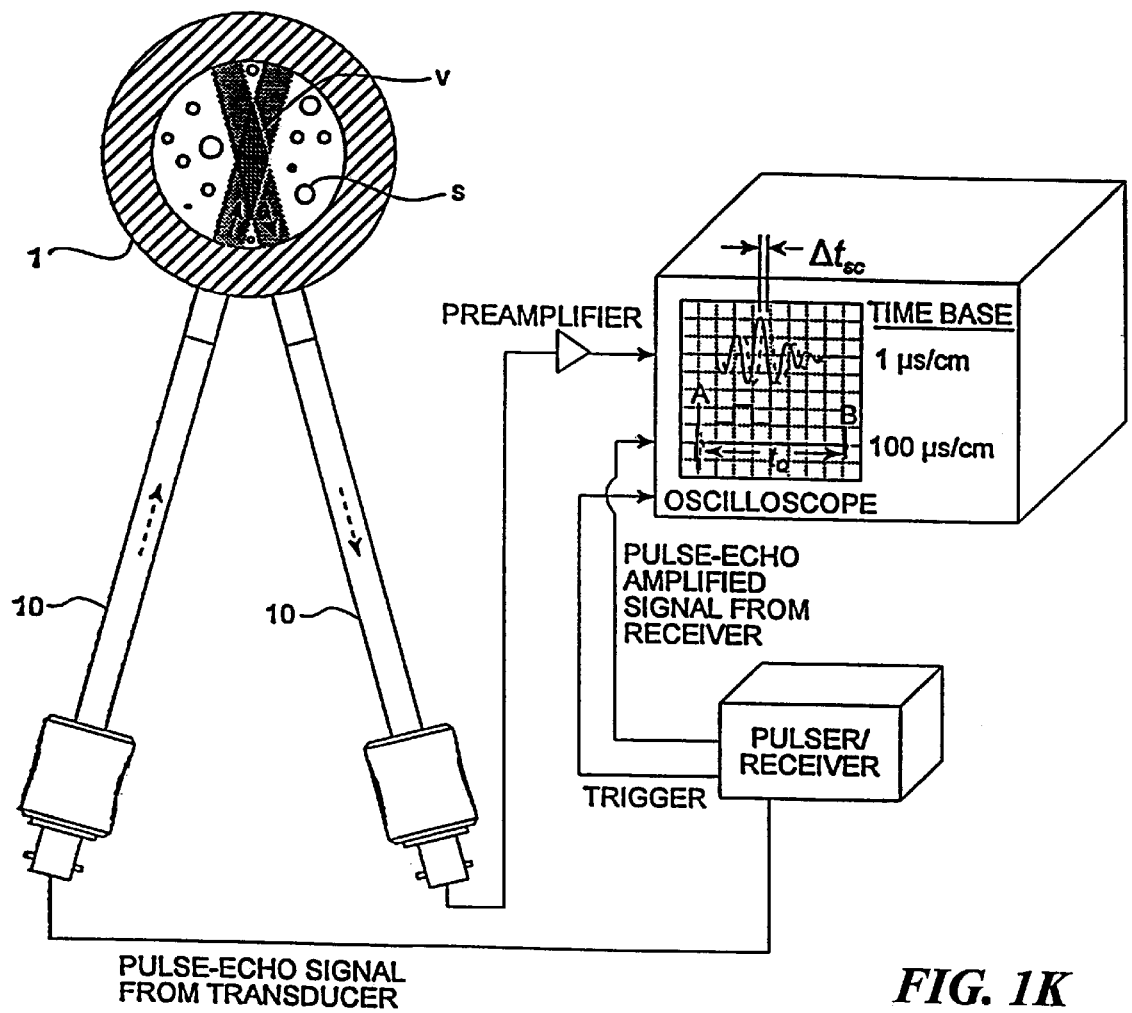
FIG. 1K shows the end view of a pipe that contains a fluid with scatterers, illustrating a reflection measurement with two buffer waveguides of the invention.

FIG. 1K shows the end view of a pipe 1 that contains a fluid with scatterers s, e.g., water plus air bubbles, and depicts a reflection measurement of scatterer velocity during the quiet time $t_Q$ between the waveguide end-to-end echoes A & B (bottom trace on the oscilloscope). The change in transit time $\Delta t_{SC}$ is obtained by stroboscopically timing echoes (top trace) from the ensemble of scatterers within the scattering cell v, using two (or more) transmissions, according to the method of Jacobson et al., U.S. Pat. No. 4,787,252 (Nov. 29, 1988). The other principal components in the system are the commercially-available pulser/receiver and a preamplifier which may be tuned. The scattering cell or interrogation volume v is defined by the beam intersections and the range gate timing windows.

Figure 1L:
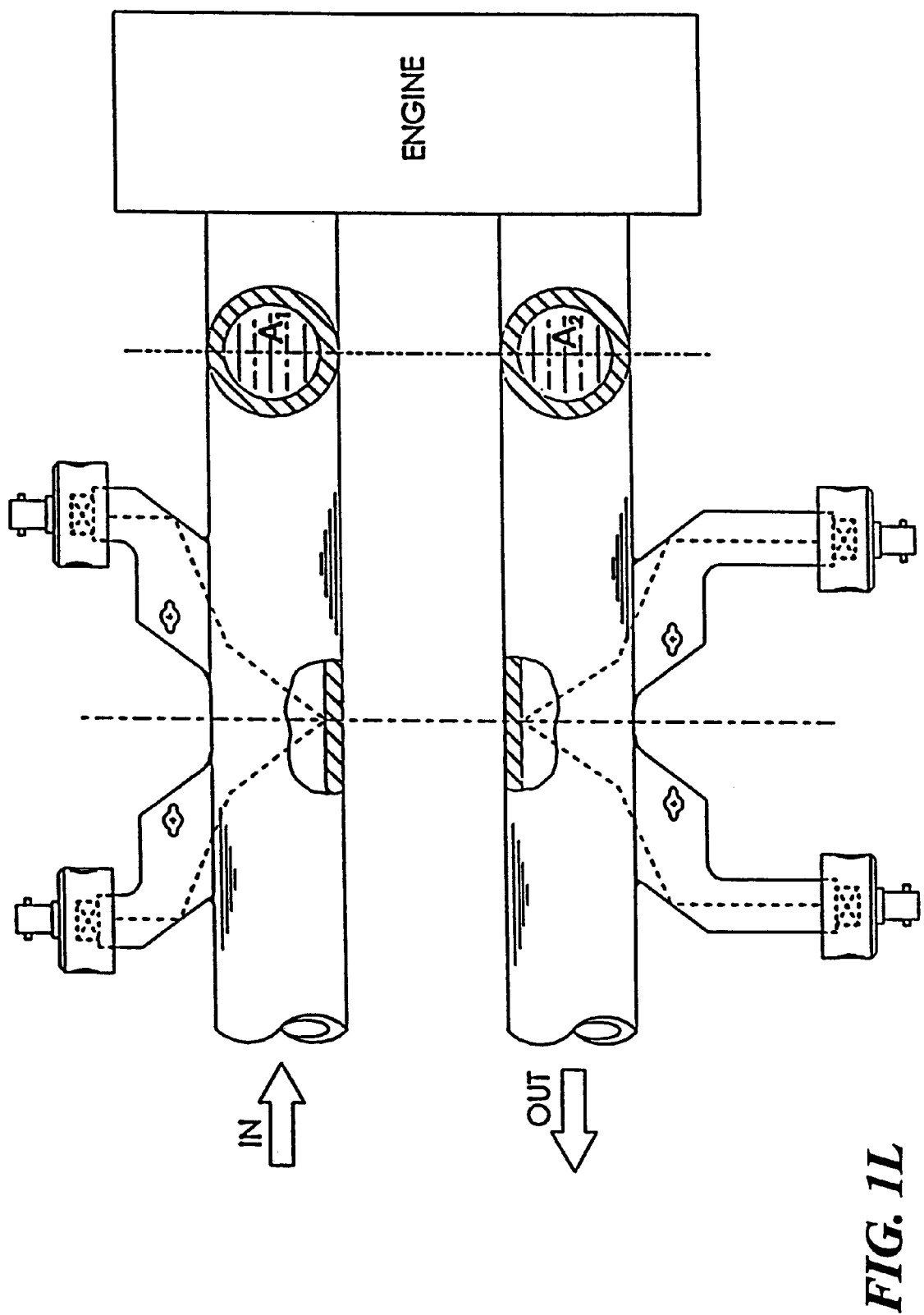
FIG. 1L shows a differential mass flowmeter for organic liquid that combines Rao's Rule for organic liquids and two flow velocity measurements, on hot and cold pipes with waveguides of the invention.

FIG. 1L shows a differential mass flowmeter for organic hydrocarbon (HC) liquid that combines Rao's Rule for organic liquids and two flow velocity measurements, on the hot and cold pipes for a diesel engine. The cold incoming and hot outgoing flows are of the same composition but differ in temperature (T), density ($\rho$), sound speed (c) and volumetric flow rate (Q). Temperature does not need to be measured per se, as the fractional density difference $\Delta\rho/\rho$ can be accurately estimated as ($\frac{1}{3}$) $\Delta c/c$, one-third the fractional sound speed difference, based on relationship due to M. R. Rao, *Indian J. Physics*, Vol. 14, p. 109 (1940), cited in A. B. Bhatia, *Ultrasonic Absorption*, p. 24, Dover Publ. (1967).

Denoting parameters in the first and second pipe by subscripts 1 and 2, respectively, the difference in mass flow rate (and normally attributed to diesel fuel consumed by combustion in the diesel engine) is $\Delta M_F = M_{F1} - M_{F2}$. Each mass flow rate is given by an equation of the form $M_F = \rho V_{AVG} A = \rho Q$, where $V_{AVG}$=area-averaged flow velocity and A=area. The uncombusted fuel cools the engine and gets heated up in the process. Due to thermal expansion, density in the hotter organic liquid is less than in the colder liquid, by the amount $\Delta\rho$, where $\Delta\rho$ is obtainable from sound speeds according to Rao's rule: $\Delta\rho/\rho = (\frac{1}{3}) \Delta c/c$. If the areas $A_1$ and $A_2$ are equal, the ratio of mass flow rates simplifies to a simple function of $V_1$, $V_2$, $c_1$ and $c_2$ provided the meter factors $K_1$, $K_2$ can be estimated accurately enough from the interrogation geometry, $c_1$ and $c_2$, or perhaps from other information. For example, the c's may indicate temperature accurately enough to determine the kinematic viscosity $\nu$, from which K and Re are ordinarily determined. Sometimes the attenuation coefficient $\alpha$ is used to estimate Re, again leading to K. Similar arguments apply to organic hydraulic fluid, where a $\Delta M_F$ would be attributed to a leak.

Figure 1M:
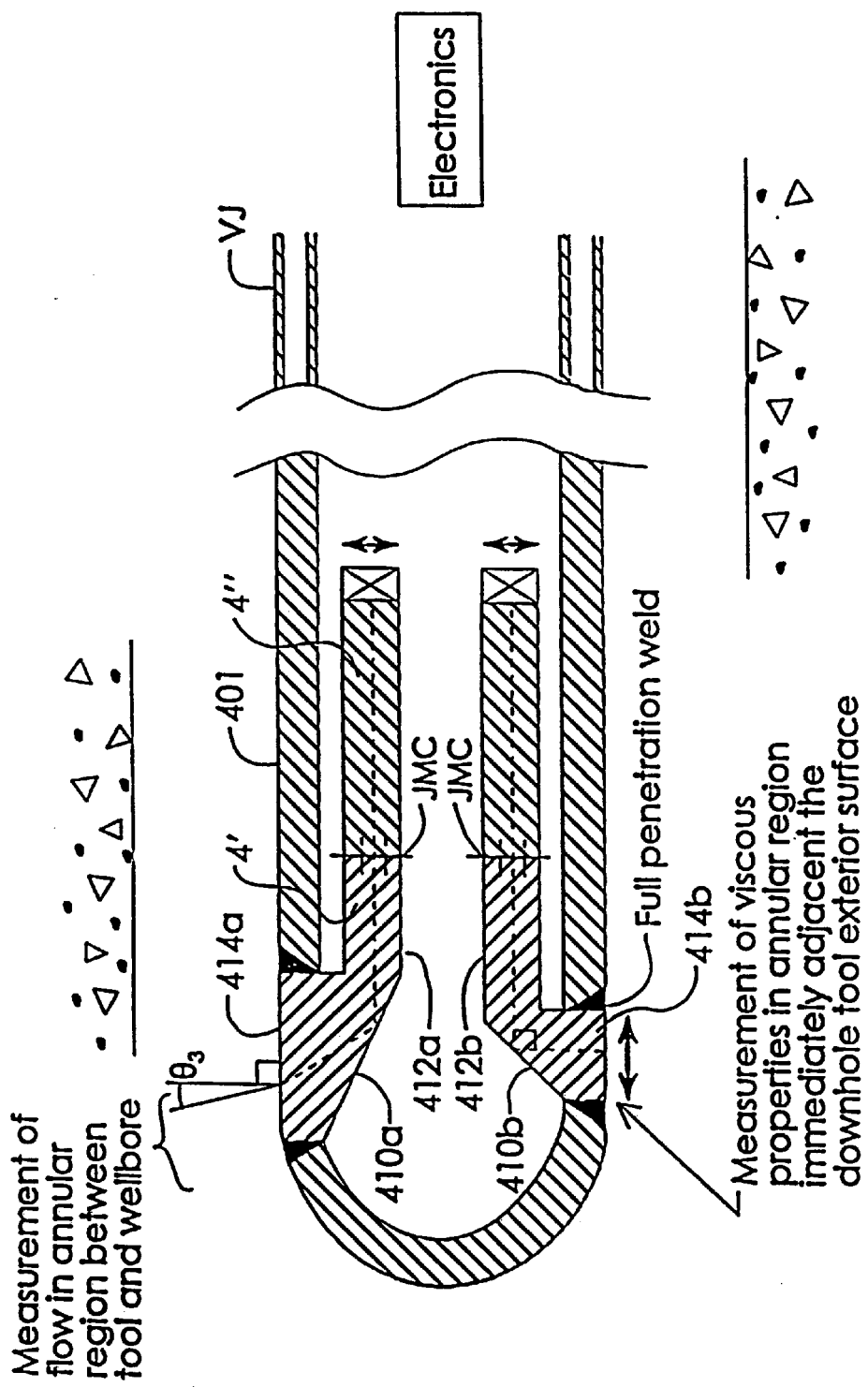
FIG. 1M shows an embodiment for performing downhole measurements.

FIG. 1M shows the hockey stick construction adapted to a downhole tool 400. In this embodiment, hockey stick waveguides 410*a*, 410*b* are mounted to extend through the wall 401 of the tool and their blades 414*a*, 414*b* are welded with through-welds thereto, while their shafts 412*a*, 412*b* extend within the tool interior. The downhole environment is one in which thermal control is difficult or not feasible, and this problem is addressed by a further aspect of the invention by forming the shafts of a first, metal portion 4', and a second portion 4" formed of ceramic and having a low thermal conductivity (as well as a low coefficient of thermal expansion), which extends from the metal trunk and mounts to the transducer. The ceramic part 4" is clamped to part 4' at a flanged metal to ceramic joint JMC. The blades 414 are thus positioned to radiate energy radially outward normal to the tool surface and detect signals indicative of conditions in the annular drilling mud region surrounding the tool, to determine one or more of viscosity and density, or a function thereof, of the surrounding material. A vacuum-jacket VJ insulates the electronics module EM.

Figure 2:
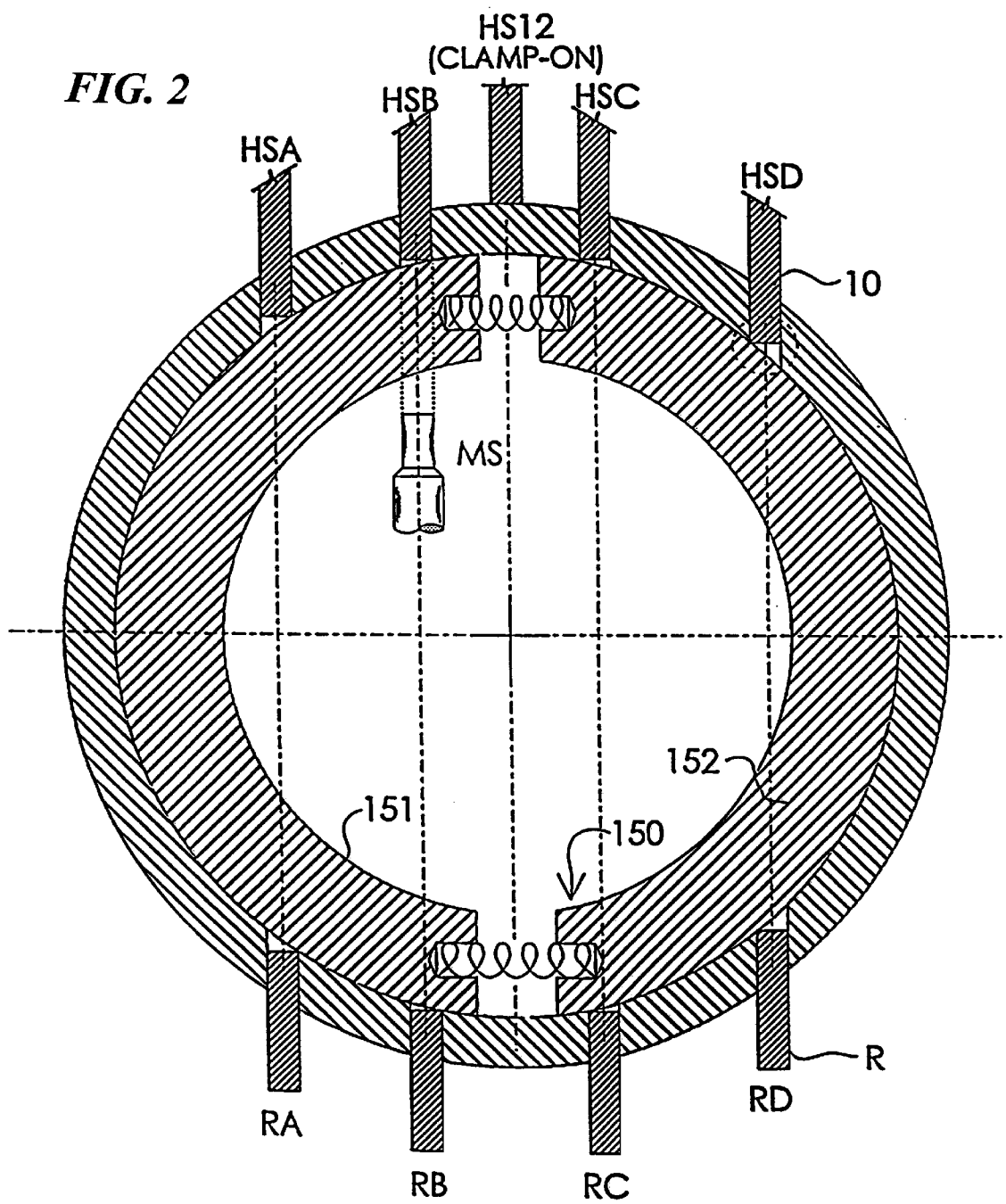
FIG. 2 shows several waveguides of the invention welded to a pipe section, for permanent installation at accurately controlled depths and locations.

FIG. 2 shows a spring loaded internal clamp jig 150 to hold or set the insertion depth for several waveguides to be welded onto or into a pipe section, for permanent installation at controlled locations, particularly at accurately controlled depths of insertion in slots. Briefly, a pair of spring biased cylindrical bodies 151, 152 rest tangent to the inner wall of the pipe, and waveguides 10 or reflectors R are inserted to abut the jig before they are welded.

Figure 2B:
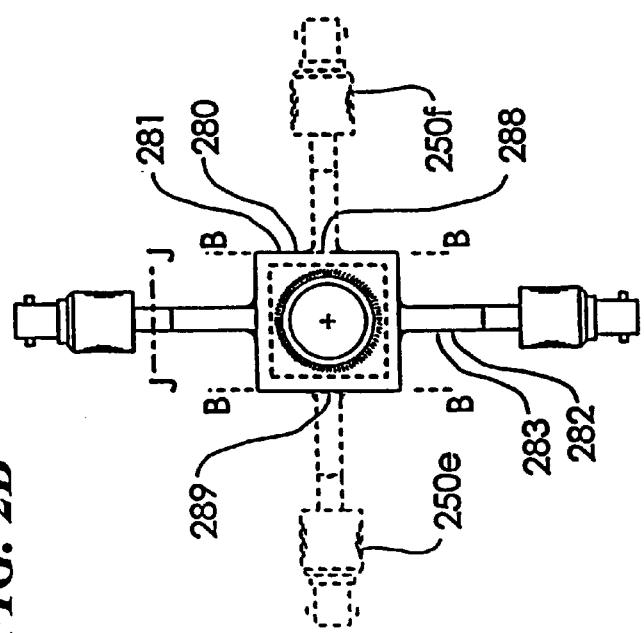
FIGS. 2A, B show views of a spirometer system using waveguides of the present invention.
FIG. 2C illustrates processing for fast response with the structure shown in FIGS. 2A, B.
FIG. 2D shows a buried conduit measurement system.
FIG. 2E shows waveguides of the invention temporarily coupled to a pipe in planes parallel and perpendicular to the pipe axis by pipe riser clamps.
FIG. 2F shows several hybrid constructions that provide (a) removability; (b) explosion proof design for low sound speed pipes, achieved by utilizing a composite waveguide; and (c) refraction angles in the contained fluid beyond limits imposed by the pipe material's sound speed relative to that in the fluid.
Figure 2A:
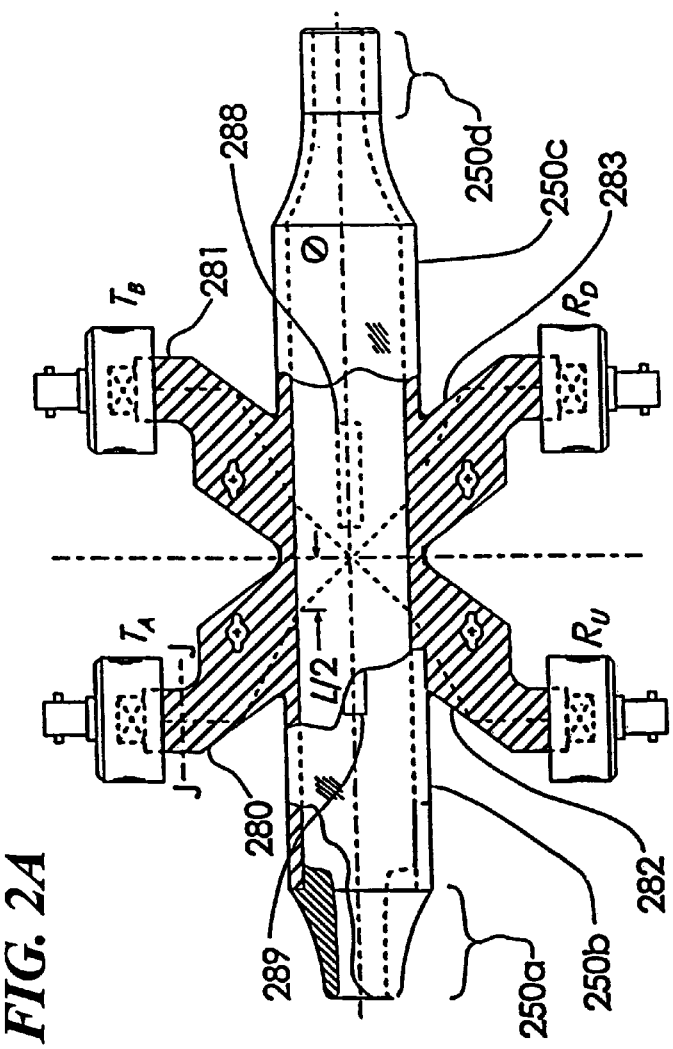

FIGS. 2A, B show two views of the waveguides cast permanently into the spoolpiece 250, which in this case is a spirometer compactly configured to measure breathing dynamics. The device may be fabricated as a monolithic plastic flowcell, shown in side view, end view and electrical schematic view in FIGS. 2A, B&C, respectively.

Figure 2C:
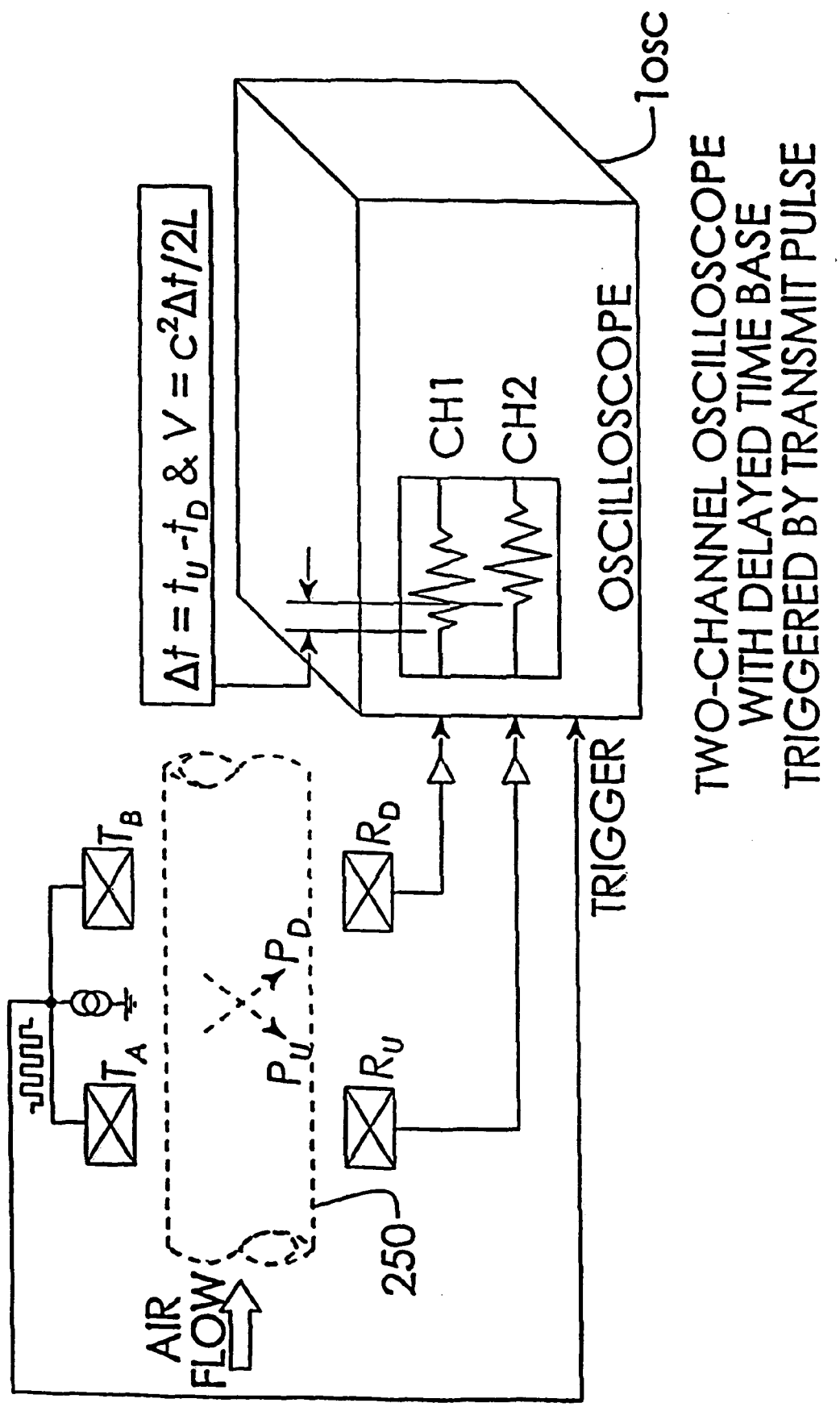

The spirometer consists of a square duct and four or six transducers for simultaneous measurements in orthogonal planes and/or in one plane. Extension portions of this multipath spirometer may be separable at J—J to accommodate sterilization procedures. The spirometer flowcell body, or at least the snorkel mouthpiece, may be a low-cost expendable item. It connects to the mouthpiece end 250*b*. The opposite end is the hose end 250*c*, which terminates in a standard hose connection 250*d*. Transducers preferably are reusable items for use with another spirometer body, unless the transducers themselves can be made so cheap that they can be treated as expendable too. For reasons of compactness, one preferred fast-response construction uses only four transducers and places all four in one plane. The four transducers, including their oblong caps, fit between planes formed by the extensions of the outer walls of the square section. These boundary planes are indicated by the dashed ( - - - ) extensions BB in the end view, FIG. 2B. The wedge plus extension transducer assembly functions like a clamp-on airflow transducer, constructed in monolithic fashion, with one or more portions optionally removable and re-couplable. Axial interaction length L is kept short so that c is essentially constant along that length, despite patient's exhaled breath not necessarily remaining at a constant temperature, humidity or composition, over time. Use of high frequency (e.g., f=500 kHz) reduces short circuit noise while at the same time it allows adequate accuracy to be obtained despite short L. While a single traverse is shown in FIGS. 2A or 2C, the number of traverses, shown by the dotted-line signal path, can be two or three, while still keeping L less than or on the order of the inner diameter (ID). The upstream-directed and downstream-directed paths in FIG. 2C are label $P_U$ and $P_D$, respectively. In FIGS. 2A and 2B the "footprints" 288, 289 of the optional side transducers 250e,250f are shown as rectangles in the side view.

Preferably in this monolithic or integral flowcell, the hockey stick material has shear wave velocity within approximately 10 percent of that of water near room temperature, i.e., roughly 1350 to 1650 m/s, and has a relatively low attenuation coefficient at 500 kHz, less than 3 dB/cm as well as a relatively low density, less than twice that of water, i.e., less than <2 g/cc with the flowcell conduit having a substantially rectilinear or square cross section such that the corners tend to block acoustic cross talk between transducers on adjacent and on diametrically opposed sides of the conduit. The low density and low shear wave sound velocity in combination with corner-blocking of crosstalk, allow one to carry out high signal to noise ratio ultrasonic flow measurements of air at ordinary temperature and pressure utilizing a relatively large refracted angle in the air within the conduit. For example, the refracted angle $\theta_3$ is set so sin $\theta_3$ exceeds 0.2, i.e., exceeds the ratio of sound speed in air to that in water, or, roughly, $\theta_3$ is greater than 10°. A phenolic plastic, such as is employed in the manufacture of brake linings, has been found to be a suitable material and performs well for this purpose.

FIG. 2C illustrates a method of obtaining a fast response with the transducer structure of FIGS. 2A–2B, for measurement of $t_U$, $t_D$ and $\Delta t$, and using, for a transmitter example, a four-cycle tone burst @f=500-kHz at a 100-Hz pulse repetition frequency (prf). The oscilloscope is preferably a two-channel oscilloscope as illustrated with delayed time base triggered by the transmit pulse, with the received signals fed through preamplifiers, which may be tuned preamplifiers.

Figure 2D:
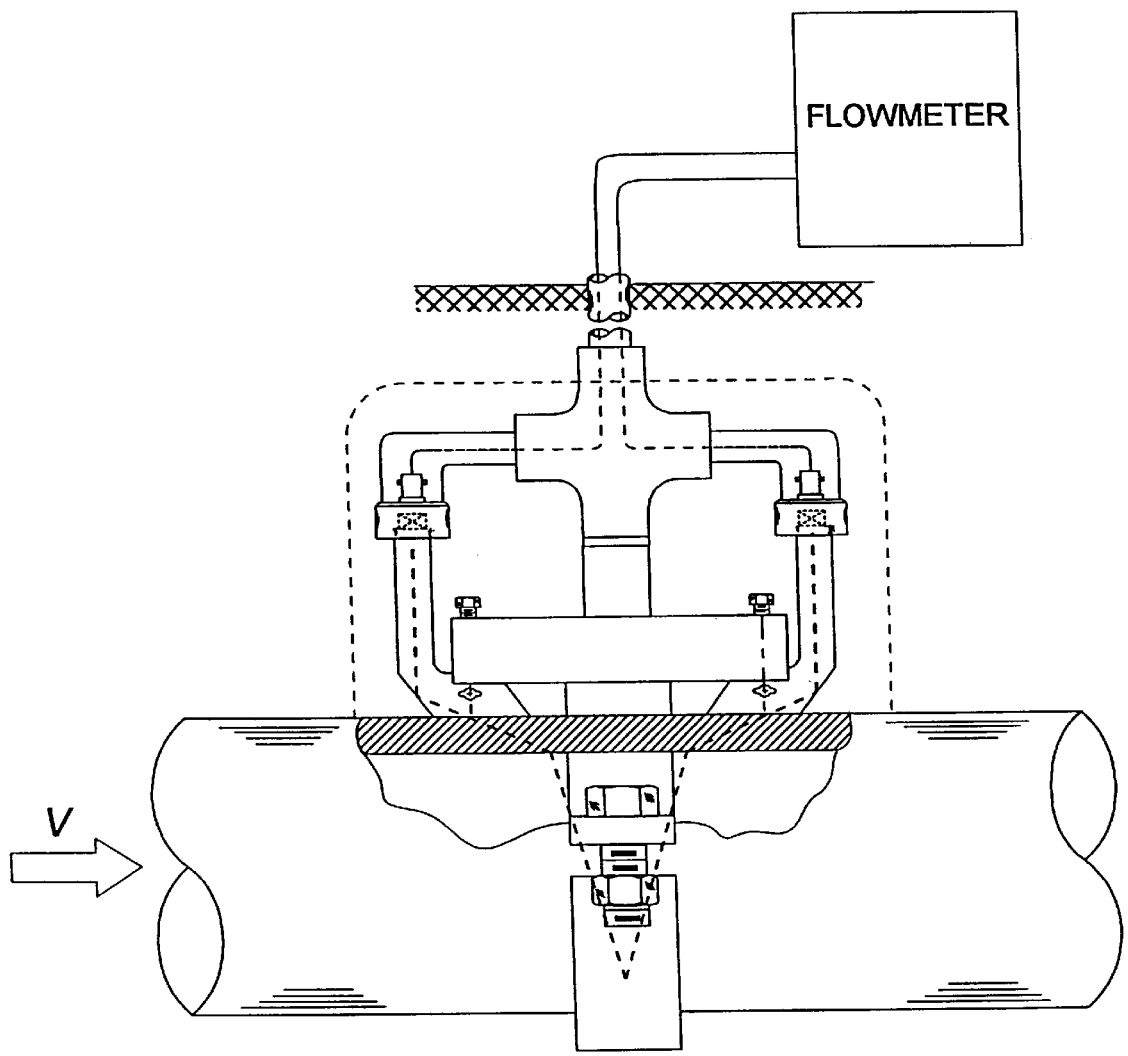

FIG. 2D shows another useful embodiment wherein the waveguides form a permanent construction for measuring flow in a buried conduit. A pair of axially-spaced waveguides are clamped to interrogate paths in a non-vertical plane to avoid reflection from the generally wet or dirty bottom surface. The clamp may be a unit such as shown in U.S. Pat. No. 4,286,470.

Figure 2E:
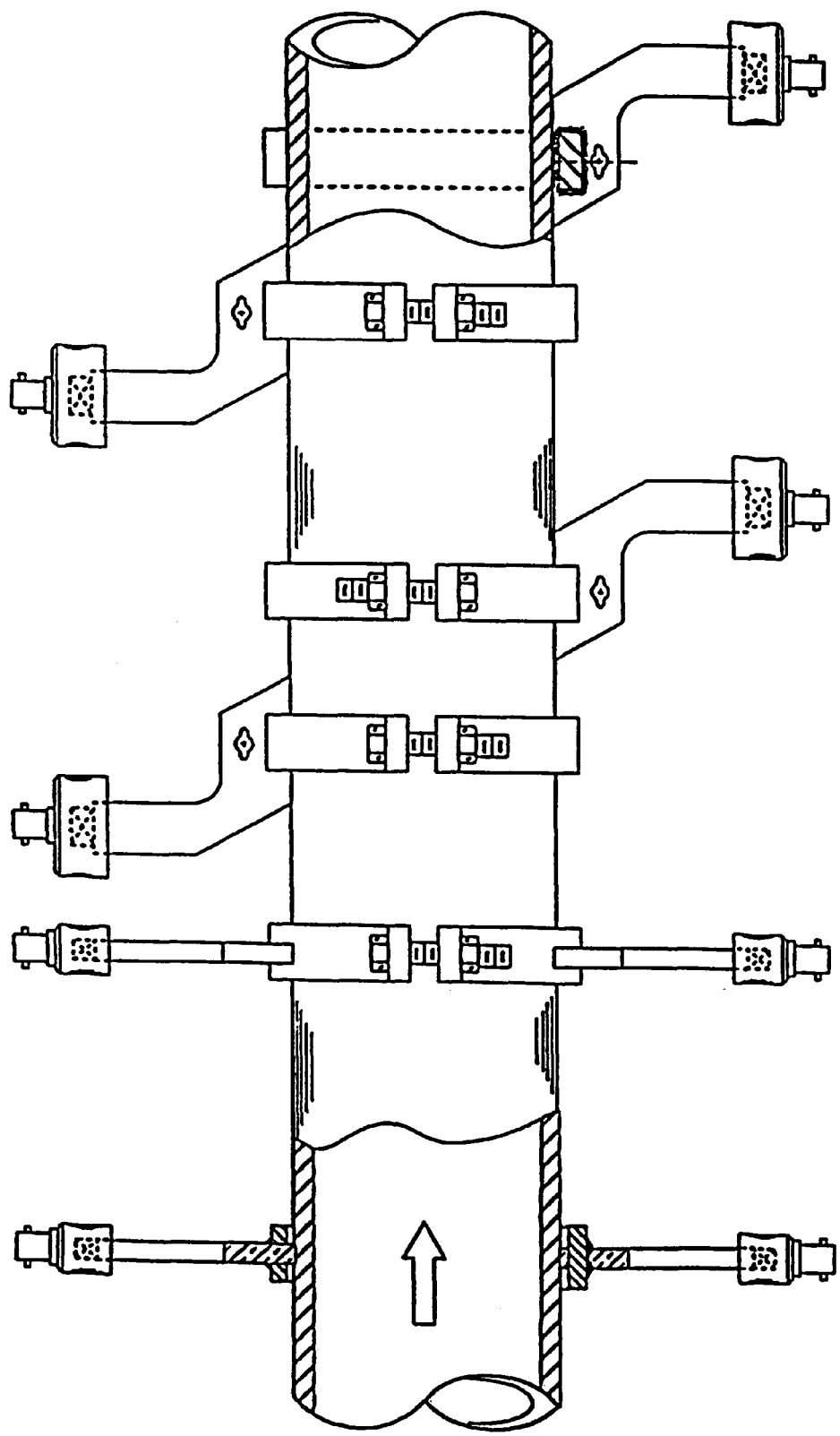

FIG. 2E shows waveguides temporarily coupled to a pipe in planes parallel or perpendicular to the pipe axis by pipe riser clamps in an economical embodiment appropriate for ordinary clamp-on applications. In the unit at the upper left, the waveguide passes through a slot in the clamp and is welded thereto. In the lower left, the waveguide is welded on the outside surface of the clamp, and a rectangular weld build-up on the inner surface provides a continuation of the metal path between the transducer and the pipe. In other arrangements, such as the right hand pair, the clamp passes through and is welded to a slot or cut-out in the body of the waveguide. In each use case the clamp and waveguide are assembled by butt-welding, or by through-welding in a slot, so as to provide the path equivalent of an uninterrupted waveguide.

Figure 2F:
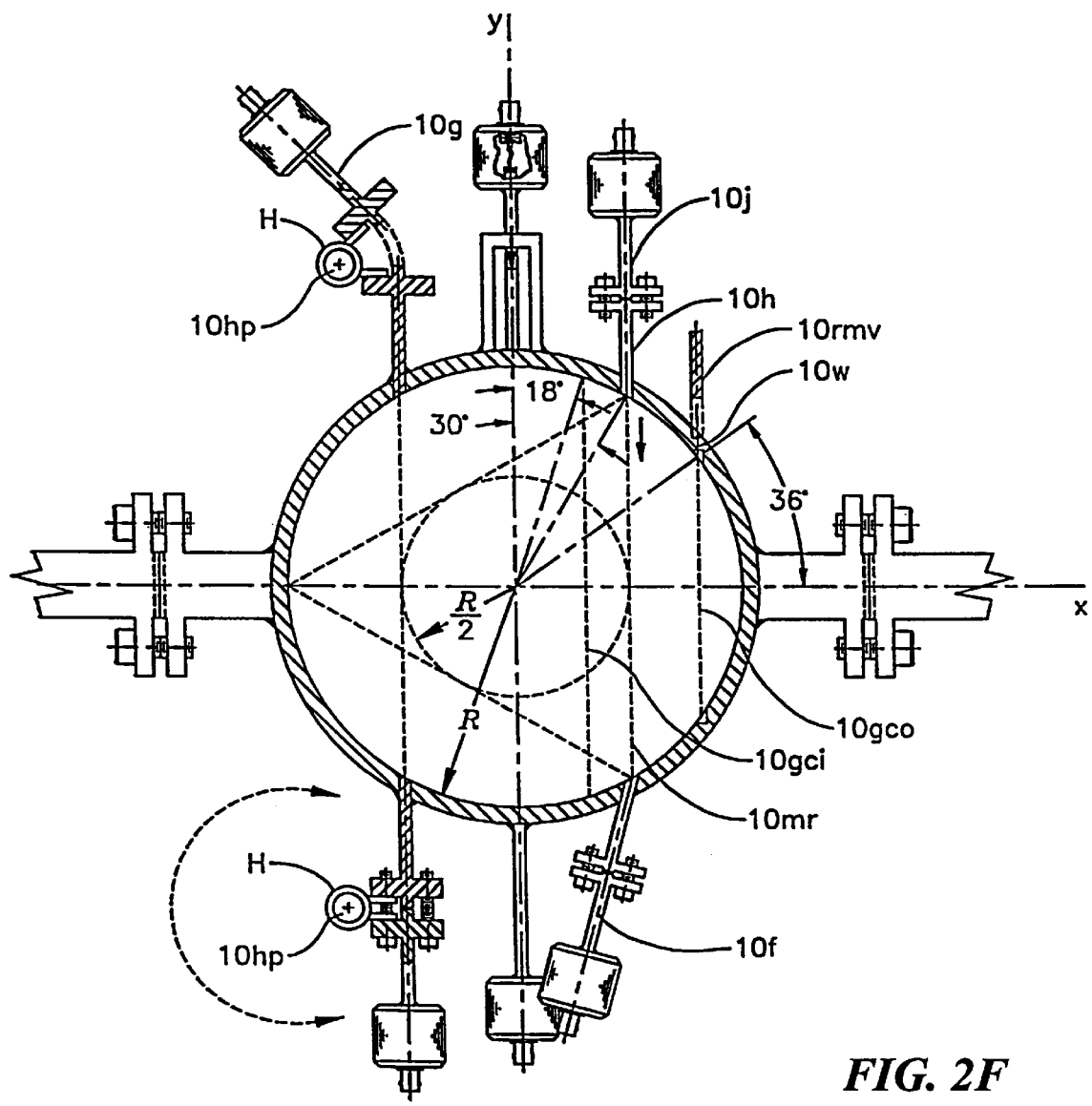

FIG. 2F shows several hybrid constructions adapting waveguides of the invention in a system to provide one or more of: (a) removability; (b) explosion proof design for low sound speed pipes, achieved by utilizing a composite waveguide in which the wedge or foot portion, and part of the extension, are of low sound speed. This yields a large refracted angle in plastic pipe. The piezo end of the buffer extension portion is of relatively high sound speed typical of metals and this metal is threaded, capped, sealed and otherwise assembled to make an explosion proof assembly. The use of low sound speed material in the foot provides refraction angles in the contained fluid beyond limits imposed by the pipe material's sound speed relative to that in the fluid. As shown, the constructions allow tilted and curved mounting geometries which may be advantageous for the spatial layout of and access to system components. FIG. 2F also shows a removable waveguide 10 rmv which is secured by a clamp (not shown) in a slot milled into the pipe surface so that it is aimed precisely along a vertical (as shown) plane. A corresponding countermilled flat is formed on the pipe interior surface, leaving a window 10w of uniform thickness in the conduit wall as the floor of the receiving slot. This assures that the signal is launched along a precise direction into the fluid, and also maintains a pressure boundary which allows removal and replacement of the waveguide in the field.

FIG. 3 is a perspective view showing the eight slots on the front side, and the four slots for accommodating reflectors on the back side of a specially slotted section of pipe designed for use as a Gauss-Chebyshev multipath flowcell in which off-diameter chordal measurements are made in well-defined symmetrically-located inboard and outboard planes. Eight waveguides of the type shown in FIG. 1 are to be welded in a minimally-intrusive manner into the illustrated narrow oblong slots that are all located on one side of the spoolpiece and which, for convenience, is referred to as the "front" side. Four reflectors are to be welded in a minimally intrusive manner into slots on the back side, and three additional waveguides of the invention can be clamped so as to measure flow in a diametral plane midway between the inboard and outboard planes, using one or two traverses. The spoolpiece is of a size that provides opportunities to mount additional sensors to independently measure swirl, circulation, sound speed or crossflow. This creates an integral spoolpiece configured for sensing both axial and secondary flow components. This construction advantageously places the passive reflectors in one location, which may, for example, be inaccessible once the spoolpiece is installed in a plant. The corner view FIG. 3A of the spoolpiece of FIG. 3, more clearly shows the uppermost one of the four reflectors R in the wall opposite the transducers. Internally-milled reflecting flats can also be milled from the inner wall in the planes of the transducers, and also between these planes to facilitate out-of-plane measurements. Returning our attention to the front side, the invention also contemplates forming internally-milled transmitting flats with blind flat-bottom externally-milled slots to provide pressure-bounding windows several mm thick (not shown). There windows locate the transducers, which may be removably clamped or epoxied thereto.

FIG. 3B shows a partly sectioned side view of a GC spoolpiece showing several clamped-on transducers at the top and bottom. Yokes Y are shown explicitly, near the top centerline and at the bottom. The clamped-on waveguides may then be calibrated using GC multipath waveguides as the reference, at high temperature and/or disturbed flow conditions.

In situations where the fluid does not require a heavy conduit, the enhanced directional beam-forming structure of the present waveguide may be used with simple sheet structures to provide highly accurate measurements.

Figure 3C:
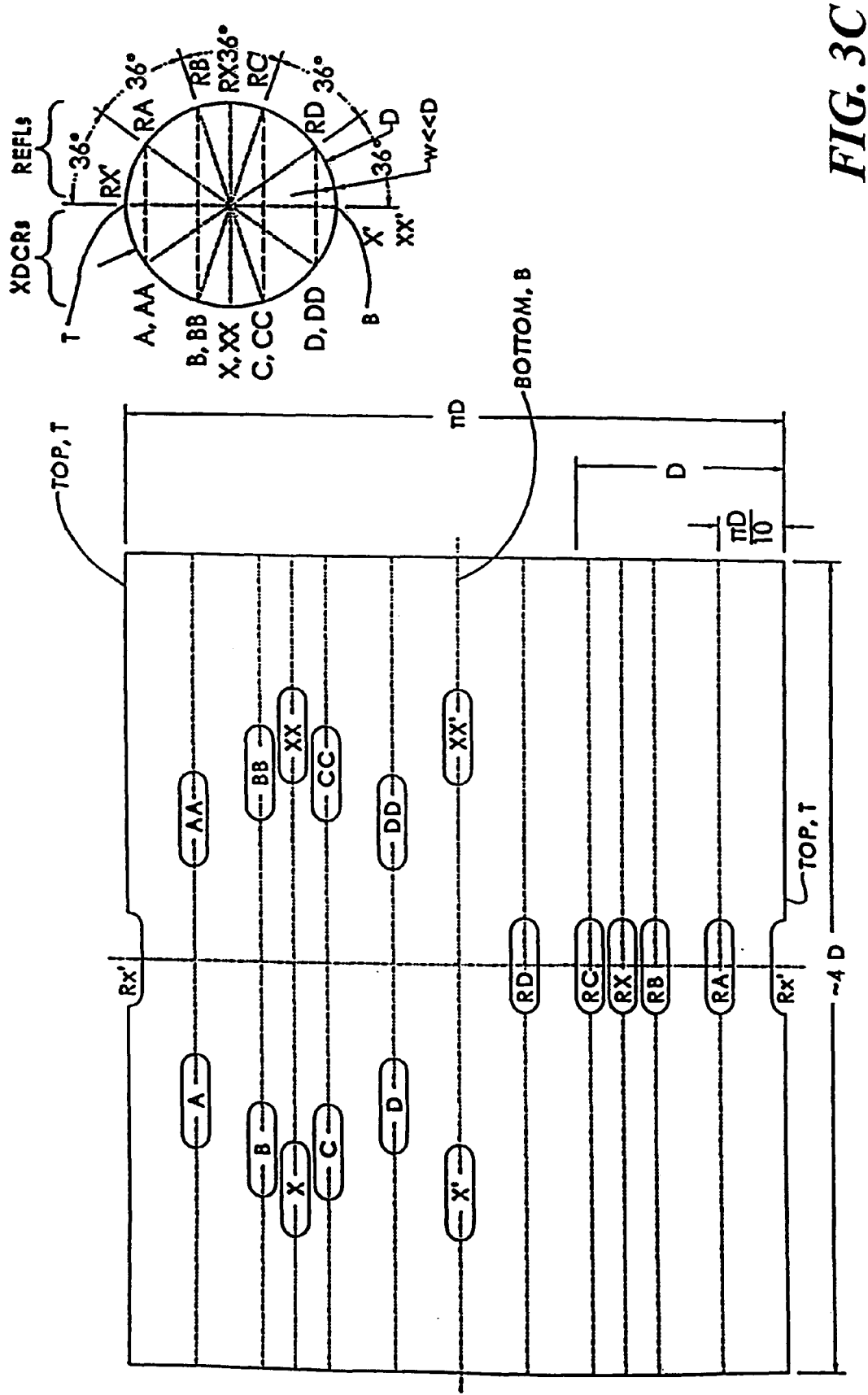
FIG. 3C shows a system in which a sheet stamping is rolled or formed into a cylinder with features aligned to form a GC and diameter path spoolpiece made out of a low-cost sheet metal.

FIG. 3C shows the layout for one such GC and diameter path spoolpiece made out of a low-cost sheet metal stamping. Slots are shown for transducers at locations A, AA, B, BB, . . . X, XX, X', XX'. Reflector slots are shown at positions RA, RB, etc. When formed into a right circular cylinder, the slots accommodate sheet metal or other transducers and reflectors, to provide GC and diameter paths similar to those shown in the spoolpiece embodiment of FIG. 3A. The top seam joins edges T, T of the stamping with centerline slots X, X' thus positioned along a line at the bottom. All transducers are positioned on one side (left) of the conduit, with all reflectors on the other side (as viewed from the end, along the conduit axis).

Figure 4:
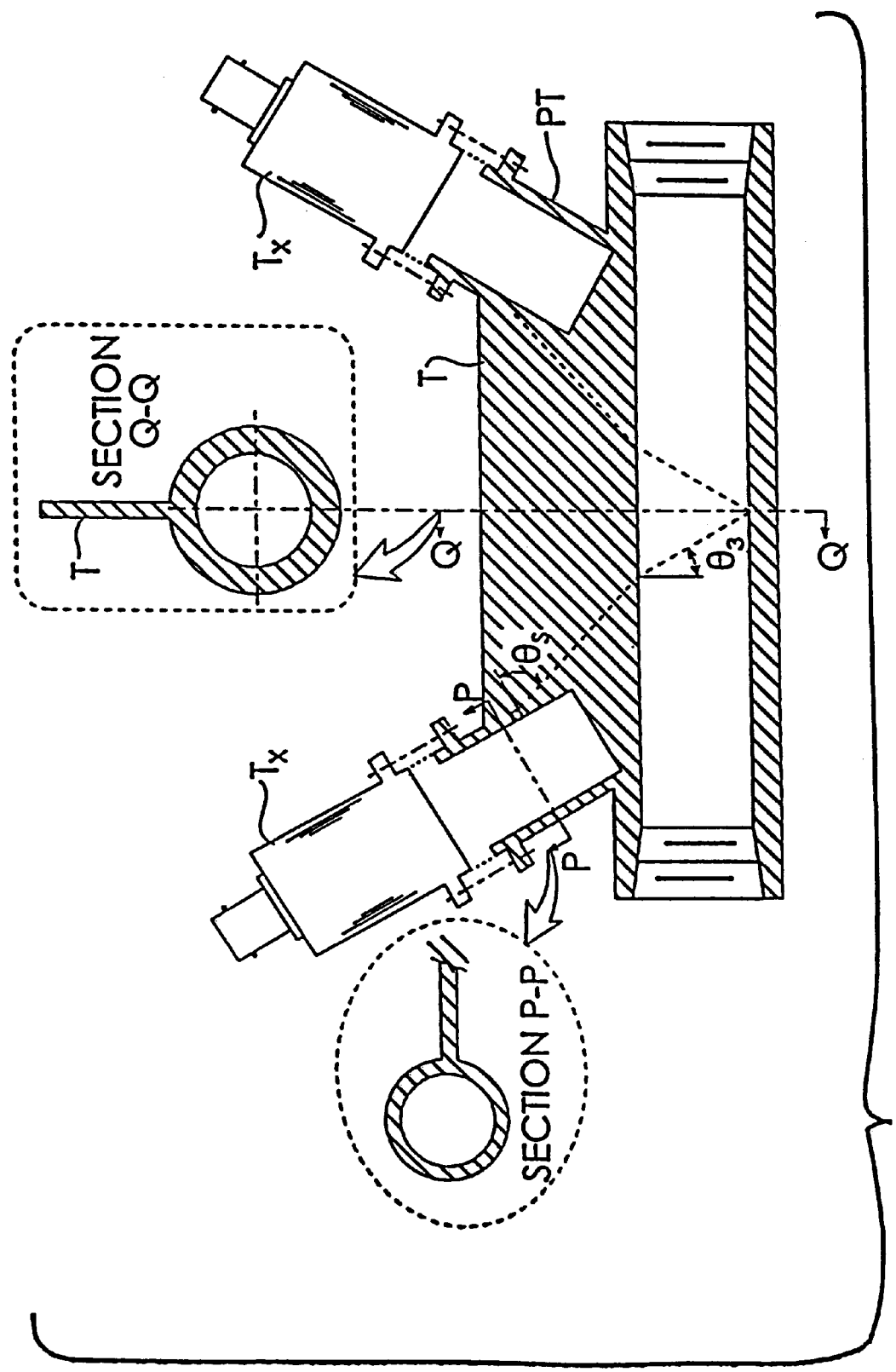
FIG. 4 is a monolithic embodiment having a plastic tube conveying symmetrical waves, a thin section conveying mode-converted shear waves, and permanent or removable transducers, flange-mounted for illustrative purposes of removability.

FIG. 4 shows another monolithic embodiment comprised of a plastic tube PT conveying symmetrical waves, a thin section T conveying mode-converted shear waves, and permanent or removable transducers Tx, flange-mounted for illustrative purposes of removability. FIG. 4B is another monolithic version, made of SS. It is geometrically similar to the plastic version, but due to a smaller Poisson's ratio for SS, the cylindrical portion is tilted back more, to achieve a similar angle of incidence near 60 degrees. The sine of the refracted angle equals 0.707 times the square root of [Poisson's ratio plus one].

Figure 4A:
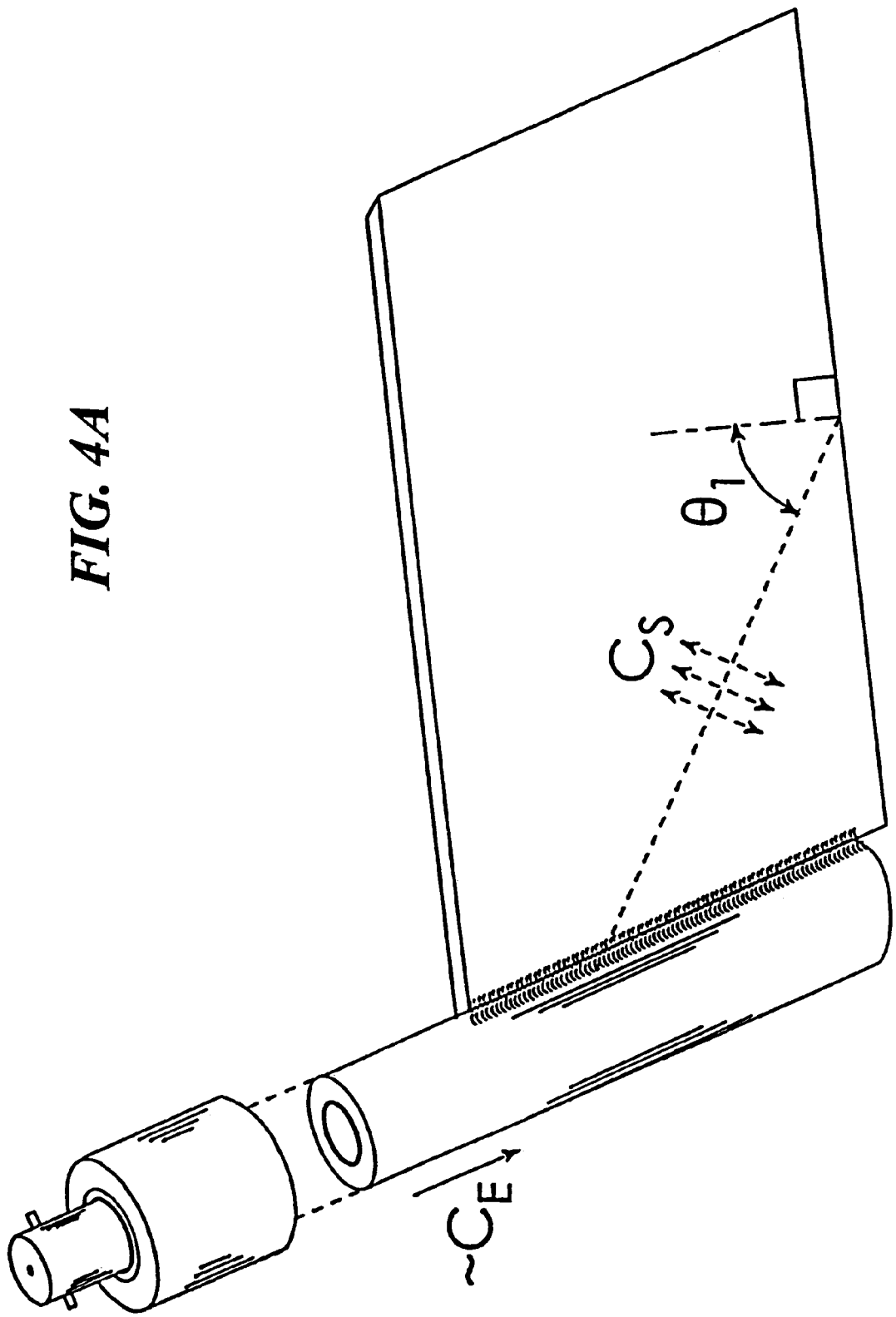
FIG. 4A shows a mode-converting embodiment which is part tubular and part sheet, the tubular part comprising the major part of the extension portion of the assembly, said tubular part being of thin wall and therefore capable of conveying with virtually no dispersion, compressional waves in a quasi-extensional or quasi-$S_O$ symmetrical plate wave lowest-order mode, where these waves are launched from an easily-coupled, easily removable longitudinal wave transducer, and where these waves leak off into the sheet as shear waves, vertically polarized, at an angle of incidence similar to that of the waveguide of FIG. 1.
Figure 4B:
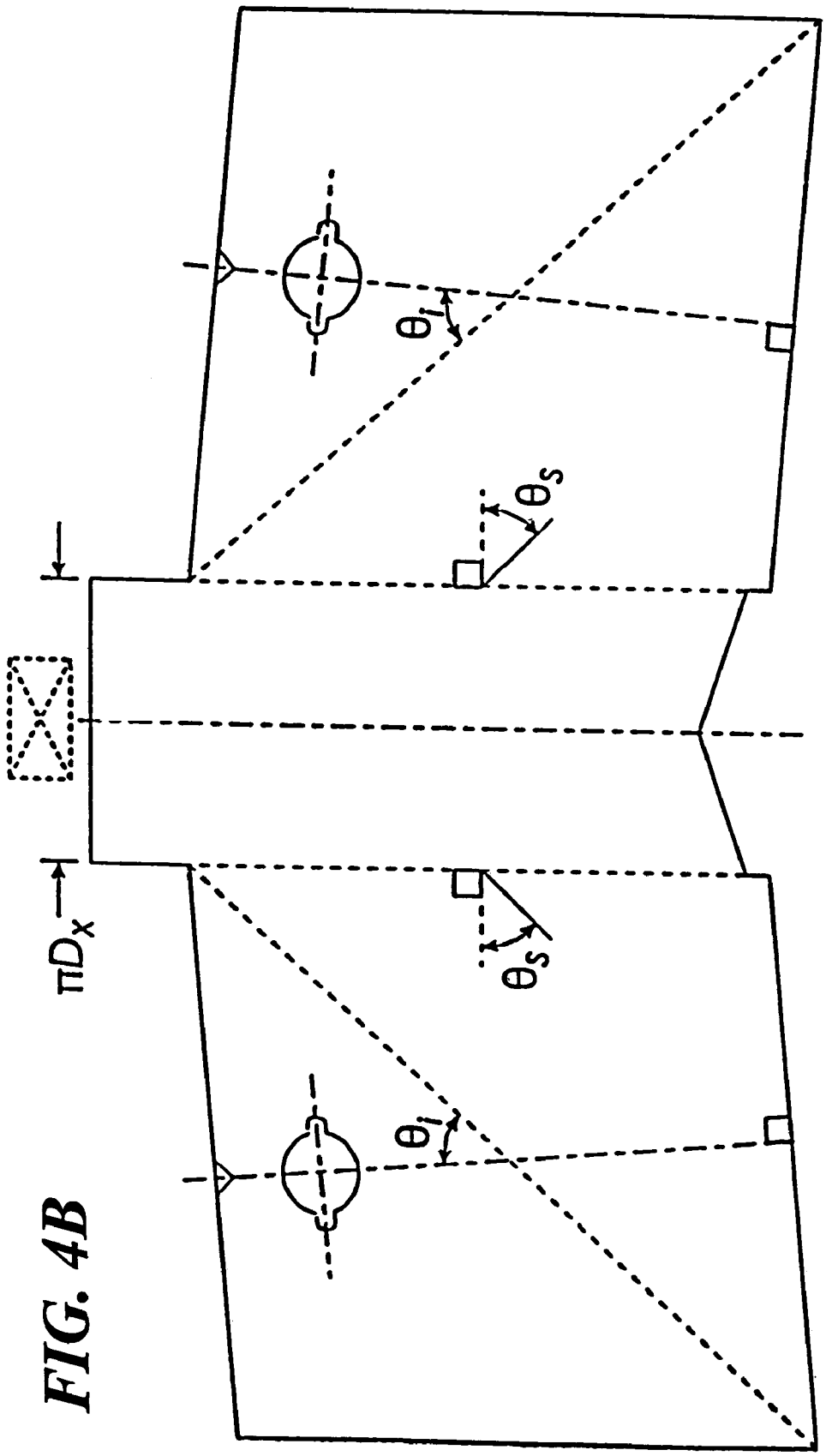
FIG. 4B is another monolithic embodiment, which is geometrically similar to the plastic embodiment of FIG. 4, but is made of stainless steel and due to a smaller Poisson's ratio for SS, the cylindrical portion is tilted back more, to achieve a similar angle of incidence (near 60°)
Figure 4C:
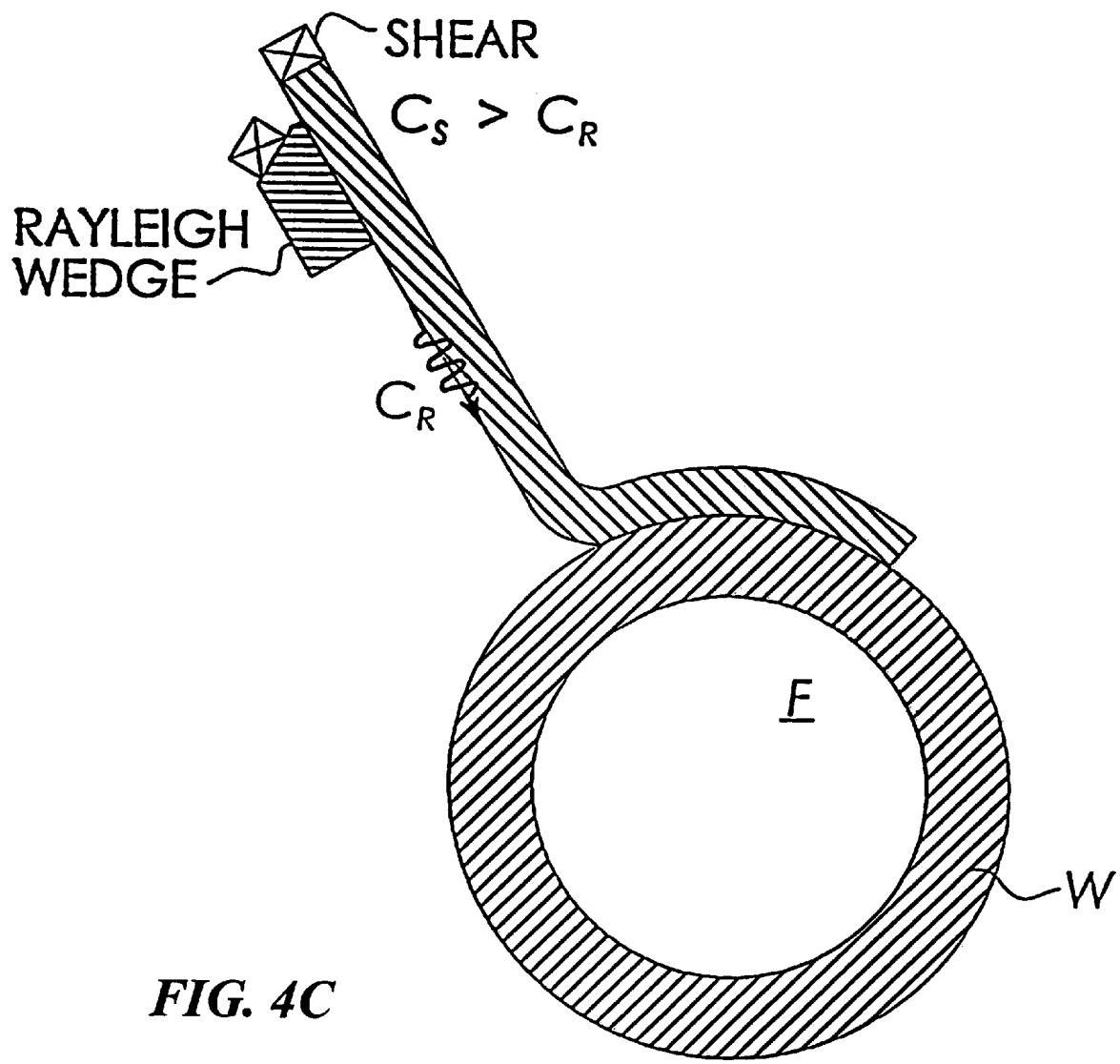
FIG. 4C is another mode-converting structure which, when partly wrapped around the pipe, is particularly well-suited to launching horizontally-polarized shear waves around a section of pipe of the same material or same sound speed as the foot portion, and in addition, in different pipes, to launching vertically-polarized shear waves from a surface-coupled transducer of Rayleigh waves that can be coupled to pipes of lower sound speed than the waveguide, e.g., to brass pipe from SS waveguide.
Figure 4D:
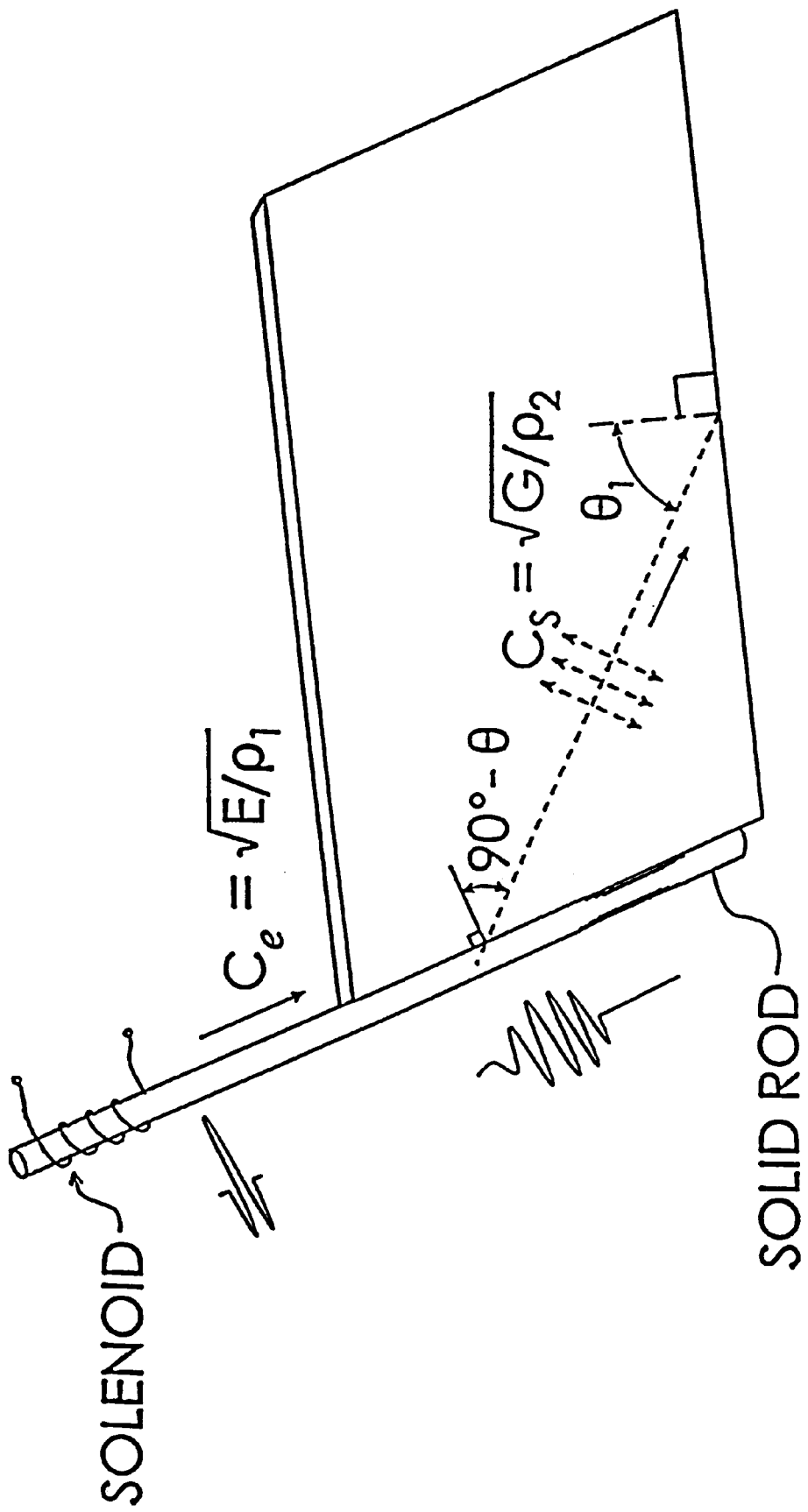
FIG. 4D is another mode-converting waveguide having a rod buffer.

FIG. 4A shows another mode-converting structure which is part tubular and part sheet, the tubular part comprising the major part of the extension portion of the assembly. This tubular part is of thin wall and therefore capable of conveying with virtually no dispersion, compressional waves in a quasi-extensional or quasi-$S_0$ symmetrical plate wave lowest-order mode. These waves may be launched from an easily-coupled, easily removable longitudinal wave transducer. These waves leak off into the sheet as shear waves, horizontally polarized with respect to the sheet's major faces, yet vertically polarized with respect to the pipe to which it will be coupled, leaking occurring at an angle of incidence similar to that obtained in the waveguide of FIG. 1. In a related embodiment, the tube may be replaced by a thin solid rod, which may additionally be magnetostrictive to allow direct activation as shown in FIG. 4D.

In FIG. 4D the solid rod adjacent the blade is a source of ultrasonic energy. When the rod diameter is somewhat larger than the "thin rod" condition of about a tenth the wavelength of a compressional wave therein, an initially broadband pulse will disperse (smear) with the lower frequencies traveling faster than higher frequencies. This behavior is described by the Pochhammer and Chree thin-rod equations and is analogous to that of symmetric plate waves of zero order, analyzed by Lamb, and accordingly part of the group of plate waves called Lamb waves. This consideration leads us to two modes of operation for the device of FIG. 4D. First, when operated in or near the long wavelength limit, the solid rod provides a broadband pulse to the blade. But second, when operated in a dispersive or marginally dispersive manner (as explained in applicant's U.S. Pat. No. 5,159,838) a pulse, which may be relatively broadband when launched at the solenoid, gradually smears, so that its lower frequency components reach the blade first, followed by higher frequency components. This is symbolically indicated by the waveforms drawn alongside the rod in FIG. 4A. Furthermore, because the lower frequency travels faster, the refracted angle of its leaky wave in the blade will be less than the refracted angle for the higher frequencies. Applicant uses this dispersion to create a spreading wave in the blade, much as occurs with the curved reflector shown in FIG. 1D. Applicant has found that if a transducer like Tx of FIG. 4 produces a 500-kHz broadband pulse at one end of the rod, and if the rod is made of titanium with a diameter of 3 mm, in a length of about 125 mm (5") the pulse will smear into a burst whose first cycle will be about twice as long as the fifth cycle. The rod thus operates as a "mechanical" (nonelectronic) chirp generator, that can launch a chirped pulse into the blade. Similar results are to be expected for rods of other materials having a phase velocity for compressional waves similar to that of titanium, such as SS, nickel or remendur, the latter two materials further being magnetostrictive.

These effects can also be produced when the compressional waveguide is a tube, as shown in FIG. 4A. For achieving the different propagation characteristics of waves in a tube embodiment, the wall thickness compared to wavelength plays a role similar to that of rod diameter compared to wavelength described in connnection with FIG. 4D.

FIG. 4B illustrates a monolithic assembly made from one piece of sheet metal, e.g., SS316, approximately 1 to 2 mm thick. The central "fuselage" is curved into a cylindrical shell that guides quasi-extensional (~$S_0$) waves. The "wings" on each side function as the wedge plus a short extension in this embodiment. The invention also contemplates another mode-converting structure which is partly wrapped around the pipe, and is particularly well-suited to launching horizontally-polarized shear waves around a section of pipe of the same material or same sound speed as the foot portion. In addition, in different pipes, it is able to launch vertically-polarized shear waves if the waveguide additionally conveys Rayleigh waves that can be coupled to pipes of lower sound speed than the waveguide, as occurs, for example with a SS waveguide and a brass pipe. Such an embodiment is shown in FIG. 4C. The Rayleigh wedge (FIG. 4C) launches a wave propagating at velocity $C_R$ which is coupled into the wall W and launched in the fluid F.

Figure 5:
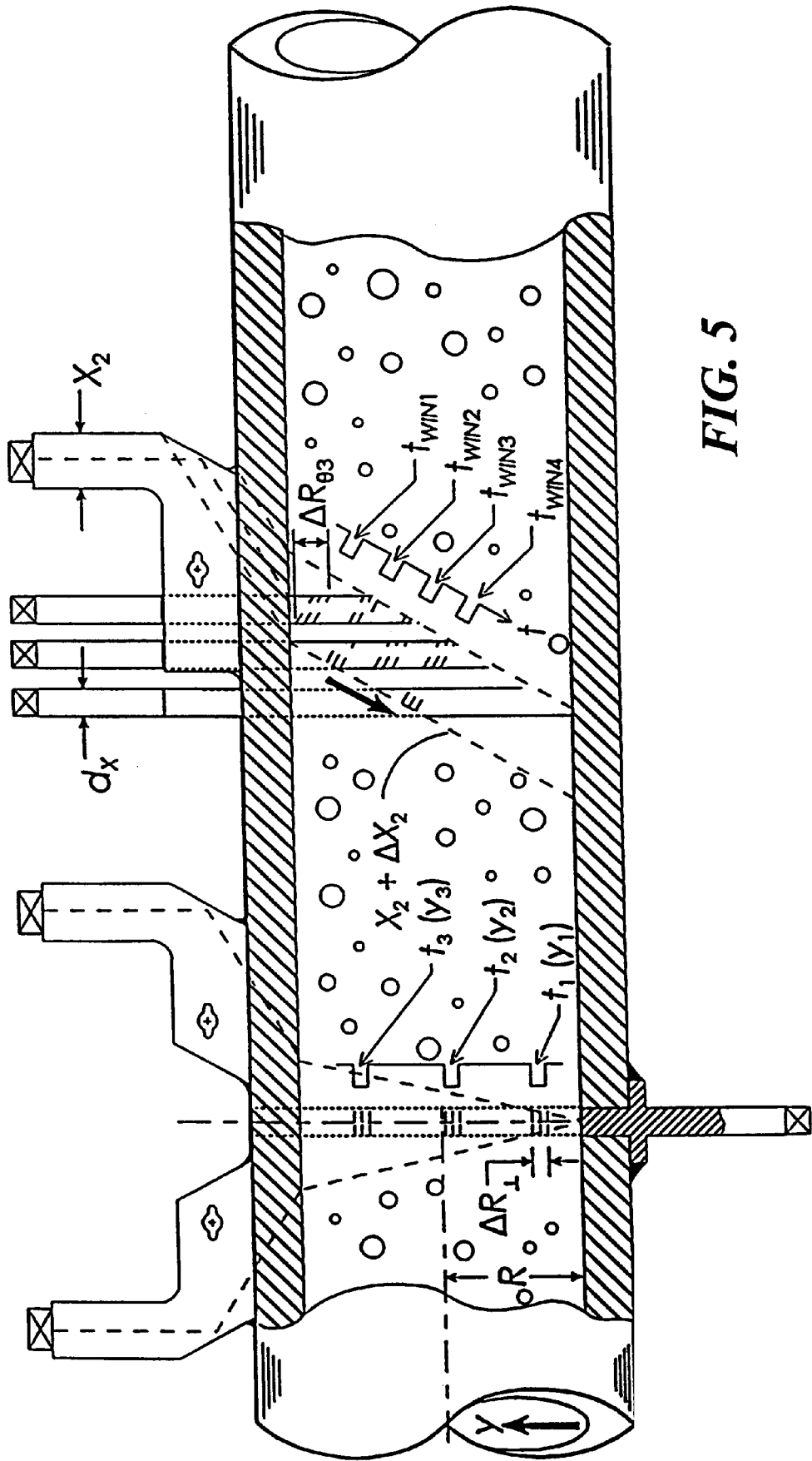
FIG. 5 shows a buffer waveguide embodiment configured to introduce two different modes into a pipe, shear waves at oblique incidence and longitudinal waves at normal incidence.

FIG. 5 shows another system utilizing hockey stick waveguides of the invention to interrogate the fluid in a particularly effective protocol. This protocol introduces two different modes into the pipe, shear waves at oblique incidence and longitudinal waves at normal incidence, generated independently and waveguided external to the pipe independently over most or all of their paths, to measure at the intersection of their paths in the fluid, the flow of a medium containing scatterers in a first mode of application. The common volume of intersection may be further restricted by range gating. In a second mode of application, flow is determined by a three-step process where in step 1, flow is estimated to be $V_{DIAM}$ by conventional tilted diameter contrapropagation using a pair of oblique shear wave transducers of the type shown in FIG. 1; then in step 2, the measurement is refined by estimating the meter factor K by sampling the jitter associated with the unsteady component of flow, v', in a series of range gated windows located at normalized distances y/R in from the wall and each confined to an annulus of radial extent ΔR short compared to the pipe radius R; step 2 includes estimating the Reynolds number Re based on a power law fit to the v' samples, assuming in a first approximation that the v' profile matches the shape of the actual axial velocity profile V(y/R); computing K=1/[1.119−0.011log Re], and in step 3 the more accurate value for flow velocity is computed as $KV_{DIAM}$. Determination of the radial jitter allows one to refine the profile of the steady component of axial flow across the pipe diameter. Another refinement of the meter factor K is achieved using the waveguides of the present invention by developing a measure of conduit surface roughness from the spectrum or amplitude of the zig-zag vertically polarized shear wave that is internally reflected and travels through or around the conduit wall between the waveguide mounting positions. The equation of Pai, which appears for example in *Ultrasonic Measurements for Process Control* of L. Lynnworth (Academic Press 1989) p.250, provides a relation of conduit surface roughness $\epsilon g$ to average flow profile. According to this aspect of the present invention, a system exploits this relationship and develops an estimate of roughness by analyzing one or more of the following: attenuation in the wall or fluid, the steady component of scatter at y/R=0 and/or y/R=2R. Analyzing the roughness/reflectivity relationship at the pipe/liquid interface(s) generally requires that one consider the frequency- and angular-dependence of scatter. For a given geometry and media, however, the apparent rate of energy decay, or ringdown characteristic in the wall, the fluid, or both may yield $\epsilon g$ to an accuracy which is sufficient to calculate K to within one percent. The short circuit "noise" associated with the early arrival of vertically polarized zig-zag shear, as utilized in the earlier U.S. Pat. No. 4,320,659 to analyze fluid impedance and liquid presence or level, may be analyzed according to this aspect of the invention to detect excess attenuation of a spectral component indicative of the surface roughness. This measurement can be refined by first measuring the zig-zag transmission characteristics when the conduit is empty. The zig-zag signals also contain spectral information that indicates the pipe schedule or wall thickness.

Depending on the widths of the intersecting beams (which depend on the compressional mode transducer diameter $d_x$ and the shear waveguide extension width w, and the refracted angle $\theta_3$ in the fluid), for a given window width (e.g., one microsecond) the radial extent of the window is typically two to four times longer for the two-beam intersection (see $\Delta R_{\theta 3}$) than for a single beam normal to the pipe (see $\Delta R_\perp$). Therefore, the normal beam in principle can yield two to four times better spatial resolution of the flow profile, per microsecond of range gate width. This is especially important near the wall, where the profile is maximally curved and where more fluid is represented per microsecond than deeper into the flowing cross-section, away from the wall. At normal incidence, however, the validity or accuracy depends not only on the backscattered intensity from turbulence or other sources of scatter in the fluid, but also on how well the radial unsteady flow component of turbulence can be related to the time-averaged axial component of flow velocity at that y/R.

Thus, the waveguides provide a precise structure for aiming beams, which in conjunction with a programmable intervalometer/flow meter can accurately assemble a set of fluid measurements which fully characterize the flow.

This property of accurately aiming the transmitted beam and range-gating (windowing) and filtering the receiver allows a number of novel configurations adapted to adverse measurement conditions or special measurement situations such as vortex shedding measurements.

Figure 6:
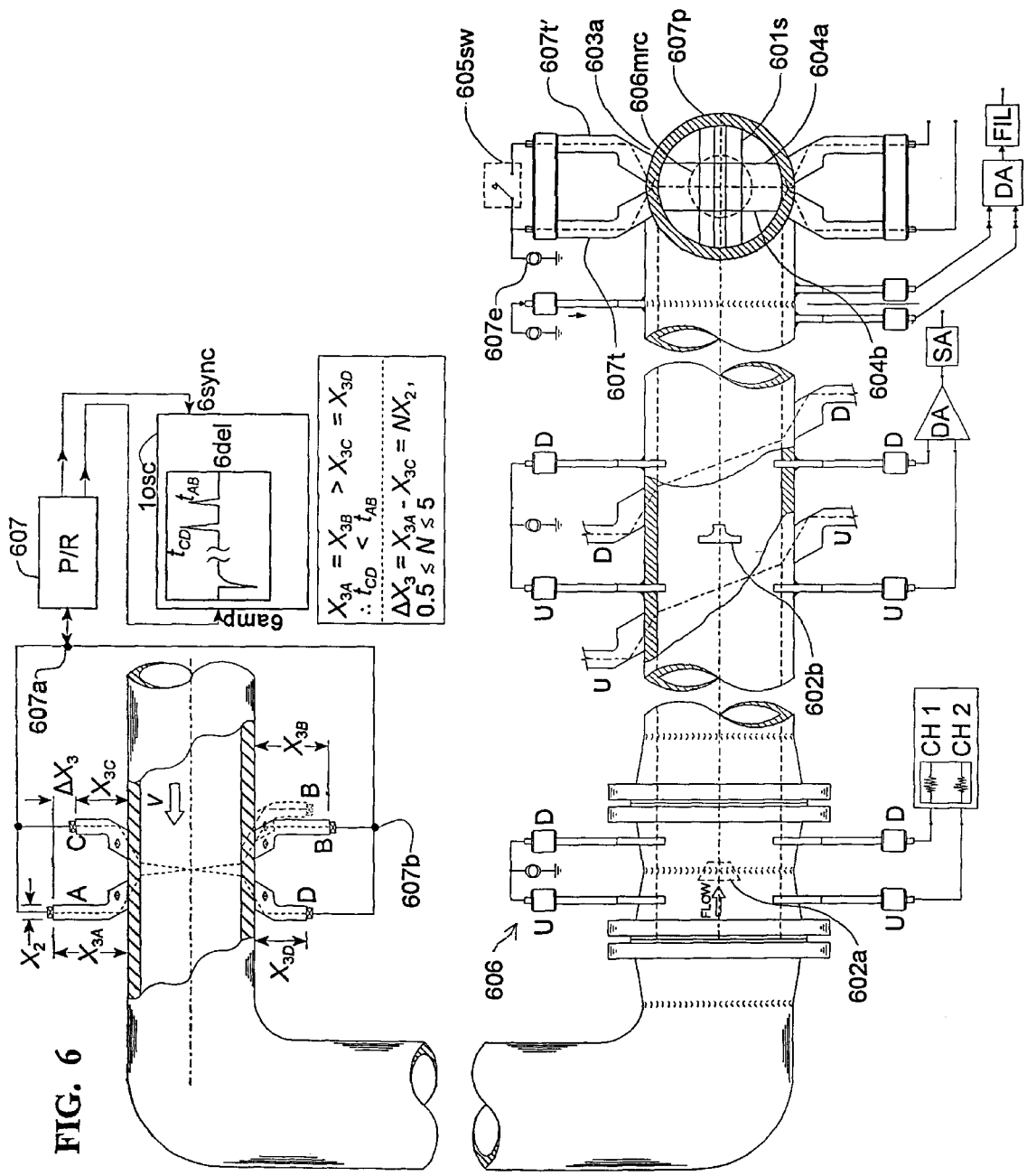
FIG. 6 illustrates differential signal processing adapted to one or more pairs of waveguides.

FIG. 6 illustrates a system employing differential signal processing adapted to one or more pairs of waveguides, of the present invention. These are mounted in a short pipe segment and are symmetrically located to equalize common mode noise (crosstalk) as much as possible. Then, rather simple signal processing is applied either to parallel, oblique or to crossed paths and this suffices for flow measurement or flow switch applications. The difference signal ΔS surviving a subtraction and filtering process is substantially responsive to one or more of: beam drift, turbulence induced attenuation ($\alpha_U-\alpha_D$), vortex shedding. In the vortex shedding case, one set of preferred paths in the fluid are perpendicular to the plane passing through the bluff body and the pipe axis, as indicated in the view looking into the pipe after it has turned through 90°. A fast response measurement system is illustrated in the upper portion of FIG. 6 employing pulse-echo interrogation of electrically paralleled transducer assemblies A, B, C and D which have intentionally dissimilar stand-off lengths allowing signal reception in a single-channel instrument during quiet times between buffer reverberations. Standoffs A and B are made longer than the pair C and D to assure timeseparation of simultaneously-launched signals that cross in the fluid. For SS316 standoffs a 1.25-inch differential in total length separates the received signals shown on the oscilloscope delayed time base at time $t_{AB}$ and $t_{CD}$ by about 10 microseconds plus or minus the effect of flow. The phantom location at the axially displaced transducer B', displaced up to about half the axial length of the exit face, shows another way to time-separate using standoffs of equal lengths. Each received signal (at $t_{CD}$ and at $t_{AB}$) widens in proportion to the flow velocity, the leading edge arriving earlier, the trailing edge arriving later. The pulser/receiver (P/R) electronics assembly 607 may be the Panametrics Model 5055PR or similar commercially available equipment, operable via its front-panel toggle switch or knob in pulse-echo or through-transmission mode.

In through-transmission mode as described above for FIG. 2C, the transmitting junction point 607a (FIG. 6) is disconnected from receiving junction point 607b. Receiving junction 607b is then connected instead to the input jack of the P/R 607, so that the changes in time-separated signals at times $t_{CD}$ and $t_{AB}$ are observable on the oscilloscope. The electronic excitation source 607e drives one or two transducers 607t, 607t' according to whether switch 605 sw is open or closed, respectively. The acoustic central rays, drawn as centerlines through each transducer and continuing through the wall 607p of the pipe propagate as refracted rays 604a, 604b, preferably parallel. Note that they pass inside the midradius circle 606mrc. The bluff body or strut 601s may be similar to struts 602a or 602b. Alternatively it may be of a shape which is symmetrical about a plane transverse to the pipe whose wall is denoted 607p, or is otherwise shaped so that it sheds whether the flow direction is into the transverse plane, or out of the plane. By placing acoustic sensors fore and aft of such a bidirectional shedder, a bidirectional vortex shedding flowmeter is obtained. The present invention also contemplates a strut that contains two different cross-sections. The first cross-section is bluff with respect to flow from a first direction, while the second cross-section is bluff with respect to flow from a second direction. These cross sections may be positioned in alternation at intervals of 0.2–0.5 D along the diameter dimension of the strut. For a measurement system, the ultrasonic beams are directed to interact unambiguously with wakes from one or the other of these cross-sections. The invention also contemplates a strut which sheds at a first well-defined edge for flow from a first direction, and sheds from a second well-defined edge for flow from a second direction. These edges may be the top and bottom edges of the strut, which in this case may have a uniform cross-section along the entire diametral dimension of the strut. The two flow directions are typically forward and reverse flow directions.

Figure 7:
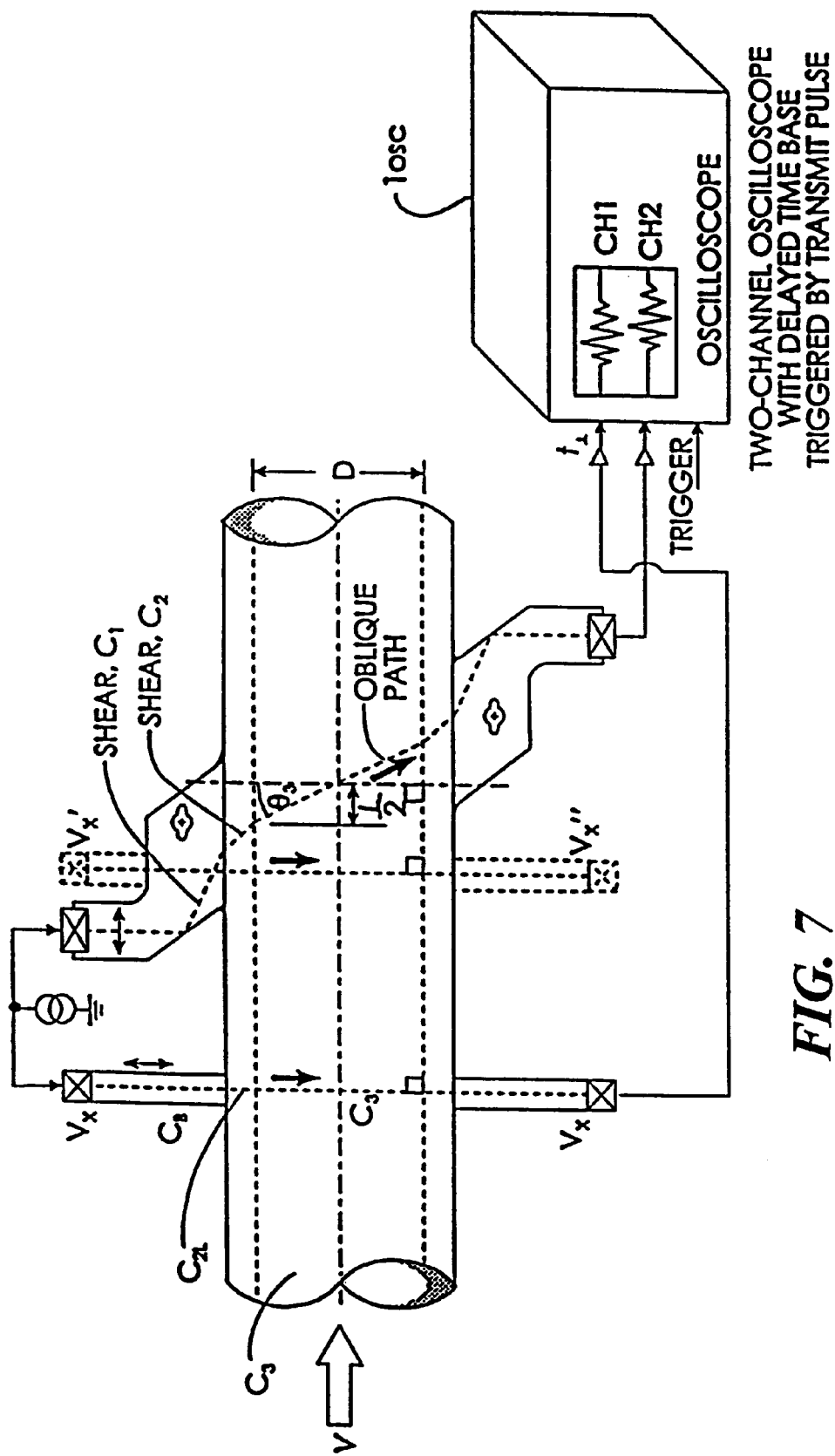
FIG. 7 shows noninvasive, externally mounted embodiments configured to measure transit time with the wind and across the wind but not against the wind, as a means of measuring flow by a transit time method when conditions do not allow for strong enough signal propagation against the direction of flow.

FIG. 7 illustrates a system using a perpendicular (crossflow $V_x$) path to measure transit time t and fluid sound speed $c_3$, and using an oblique path, inclined at $\theta_3$ in the direction of ftow to measure the incremental contribution to sound speed ($V \sin \theta_3$) caused by the flow velocity V. Heavy arrows indicate the direction of interrogation perpendicular to or oblique to flow. If flow direction reverses, the direction of interrogation along the oblique path would be reversed. This two-path or differential path method avoids the need to transmit against the direction of flow, and thereby avoids the higher attenuation $\alpha_U$ associated with that direction as V approaches or exceeds Mach 0.1. Dashed locations $V_x'$ and $V_x''$ represent alternative positions for crossflow transducers, that put the crossflow path closer to the oblique (hypotenuse) path. Alongside or within a waveguide, lines with arrows at both ends indicate longitudinal (compressional) or shear (transverse) particle motions in buffers. In these buffers, the sound speed near the pipe is $c_B$ and $c_2$, respectively. Open arrow labeled V symbolizes flow in the axial direction, left to right.

The inclined path length in the fluid $P=D/\cos \theta_3$. Here the refracted angle, $\theta_3$, is calculable from Snell's Law and knowledge of the geometry and $c_2$, the shear-wave velocity in the wedge portion adjacent the pipe. The transit time in the fluid is $t_f = P/(c_3 - V\sin \theta_3) = (D/\cos \theta_3)/(c_3 - V \sin \theta_3)$. From this, $V=(c_3/\sin \theta_3) - D/t_f \sin \theta_3 \cos \theta_3$. If $c_3$ is known to sufficient accuracy based on fluid composition, temperature and pressure, the perpendicular path measurement of $c_3$ can be deleted, or looked upon as a general self-test of the system. As a numerical example, if $c_3$=1500 m/s, D=100 mm and $\theta_3$=30°, then V=(3000 m/s)–1/4.33 $t_f$, with the units of $t_f$ being seconds.

The absolute accuracy of V determined in this manner depends on the relatively small difference between two large numbers. E.g., if the second term is 2998 m/s, V=3000–2998=2 m/s. This result is very sensitive to $c_3$. But if $c_3$=constant, and especially as V approaches $0.1c_3$ or $0.2c_3$, relative measurements of V can be reasonably accurate even if $c_3$ is not known precisely. Generally speaking, one should try to interrogate bidirectionally, in the usual contrapropagation manner, to minimize errors in V due to uncertainty in $c_3$. However, tag cross-correlation measurements along two oblique paths spaced one-half to several diameters apart may advantageously utilize monodirectional interrogation, avoiding transmission against the flow of the steam or other highly turbulent gas or fluid.

Figure 7A:
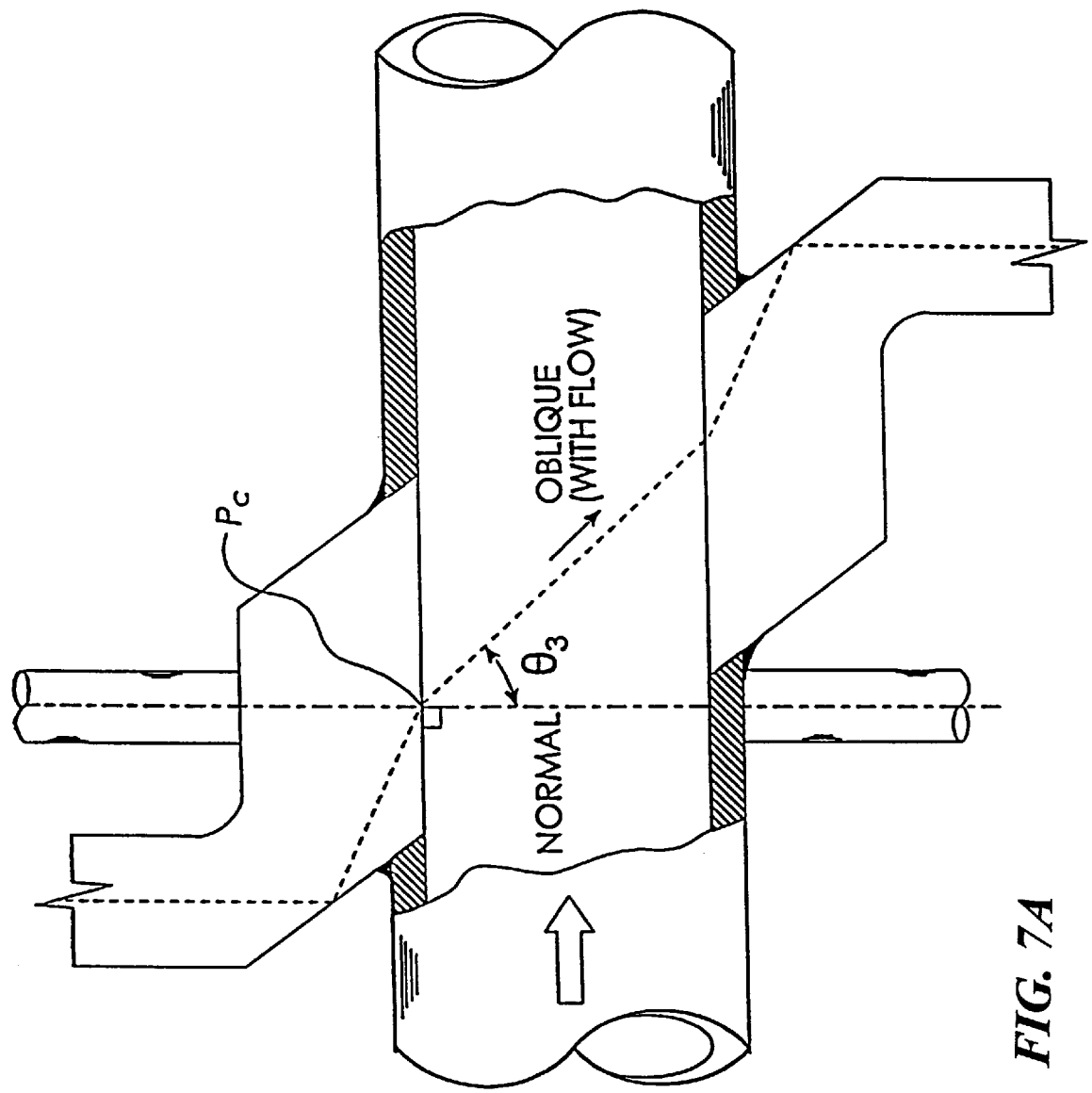
FIG. 7A is a wetted-transducer version of FIG. 7.

A wetted version of the nondispersive directive shear-wave buffer can be combined with a compressional wave transducer to measure transit times along two different paths, neither of which is directed against the flow, as shown in FIG. 7A. In this illustration, the launch point $P_c$ is the same for perpendicular and oblique rays. The triple midradius path in a plane perpendicular to the axis could also be used to measure $c_3$ perpendicular to the axis, and similarly be combined with a one-way with-the-wind oblique measurement to determine flow velocity V.

Figure 8:
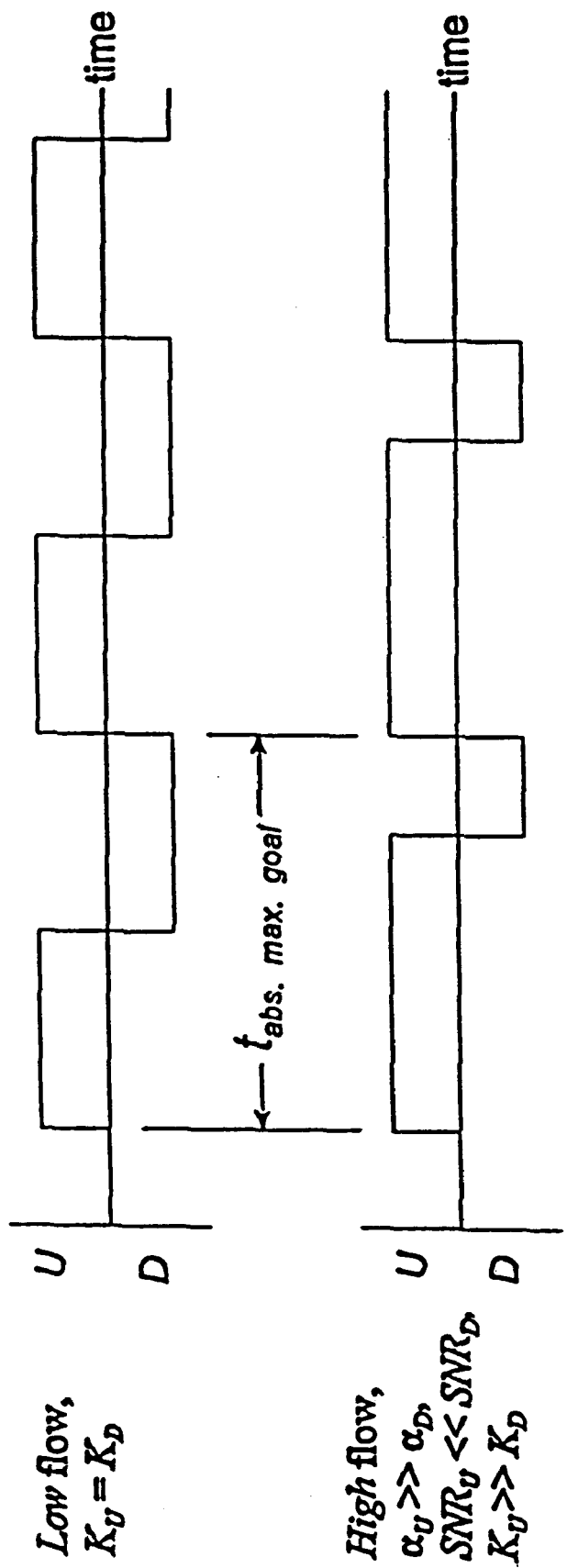
FIG. 8 shows an asymmetric duty cycle where interrogation time spent against the wind is greater than with the wind responsive to the signal to noise ratio.

In addition to systems configured to avoid upstream interrogation paths, the invention also contemplates systems wherein the received signals are enhanced by changing the upstream and downstream interrogation duty cycles to compensate for decreased upstream signal reception under high flow conditions. FIG. 8 shows a time diagram for a duty cycle where interrogation time spent against the wind is greater than with the wind, and where that duty cycle is therefore asymmetrical and responsive to the SNR (signal to noise ratio) to enhance the measured signal. Weighting can be responsive to signal amplitude, or be set to yield approximately equal numbers of successful transmissions in each direction per unit time.

Figure 8A:
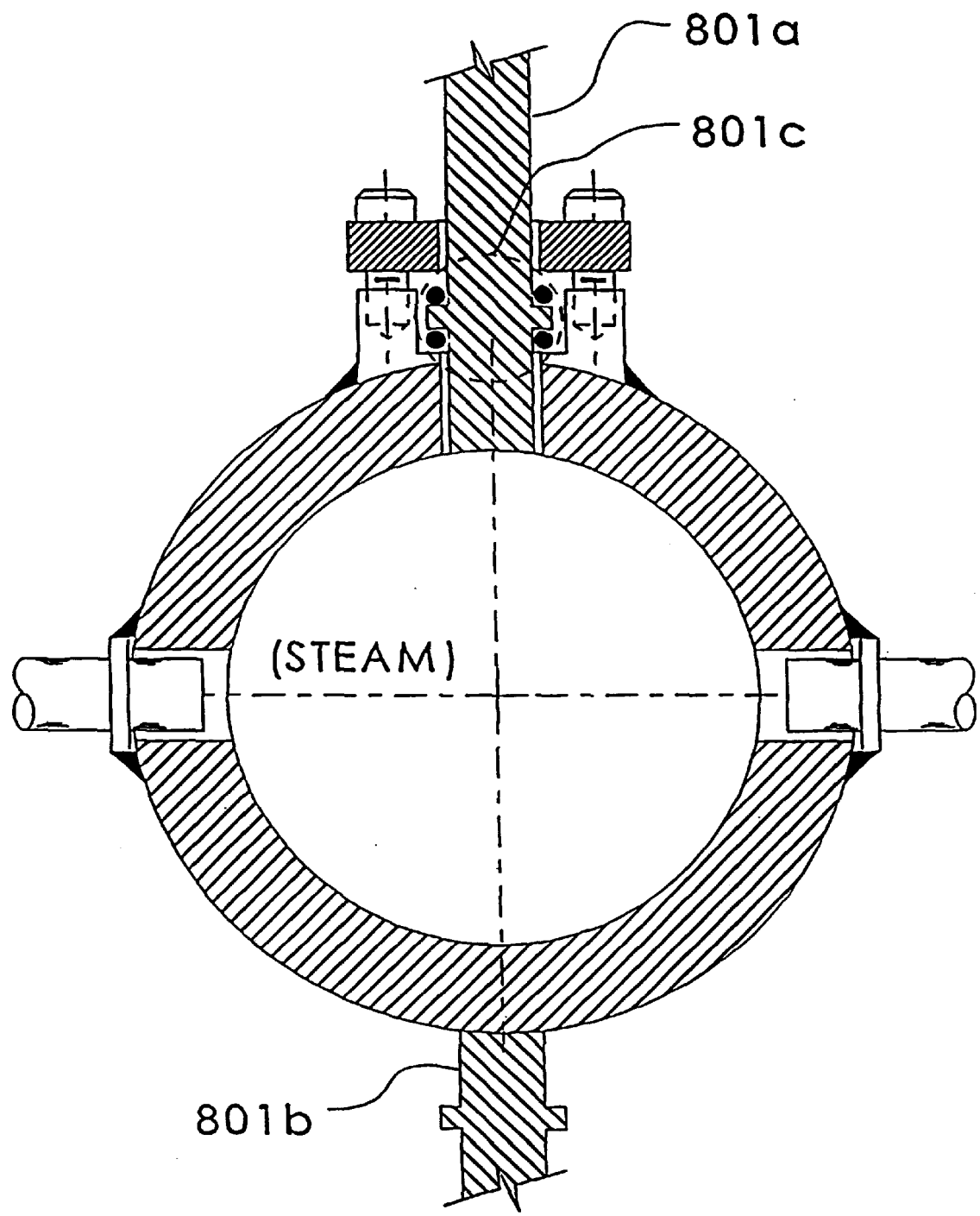
FIG. 8A illustrates a system with two identical buffer waveguides of the invention, one clamped to the outside of the pipe at the six o'clock position, while it is "wetted" mate, at twelve o'clock, passes through an oblong hole.

FIG. 8A illustrates another novel construction wherein two identical HS buffers 801*a*, 801*b* differ in that one is clamped to the outside of the pipe at the six o'clock position, while the other is "wetted" at twelve o'clock and passes through an oblong hole to radiate directly into steam at the ID. The wetted guide is acoustically isolated by an attenuative seal. At high steam pressures, two clamp-on waveguides each identical to guide 801*b* result in an effective clamp-on steam flowmeter. In the figure at the three, nine and twelve o'clock positions, annular gaps and recesses from the ID are drawn exaggerated for clarity. These may contain a sleeved bundle, indicated at nine o'clock, of the type described in U.S. patent application Ser. No. 08/477, 761 filed Jun. 7, 1995 by Applicant and Yi Liu, and entitled Ultrasonic Path Bundle and Systems.

The bundle construction described therein can be modified to operate marginally dispersively or slightly dispersively as described in connection with FIGS. 4A and 4D, namely, such that a chirp pulse is produced having a change in period (or frequency) of a factor of two in a few cycles, e.g., five cycles. This is done by forming the bundle out of relatively large-diameter rods. A bundle of some 30 rods each of diameter 3 mm can be fitted within a tube of 25.4 mm (1") OD, depending on the ID of the tube.

This dispersive chirping bundle has an interesting application in measuring the sound speed and/or flow velocity of steam or other gas which at times flows rapidly but at other times flows very slowly. At the high flow condition, which is generally highly turbulent, and having a Mach number on the order of 0.1 or larger in some cases, the leading cycles are of low frequency and hence are likely to be preserved despite beam drift and despite scattering by turbulence, even if the higher frequency cycles do not survive. The time resolution afforded by the low frequency cycles is adequate when flow is high. At low flow that low frequency time resolution may be inadequate, but the later cycles which are of high frequency content readily survive the journey across the less-turbulent, lower-flow-velocity lower-Mach-number gas (or fluid) stream and afford the necessary higher resolution of transit time. These benefits are obtained even in a pulse as short as five or ten cycles. Later cycles, if present, may be disregarded in many, perhaps most, instances. With respect to the hockey stick, the core width X2, having a numerical value typically around 25 or 30 mm, readily accommodates the chirp without introducing interference problems in that early part of the pulse used for timing.

Still another feature of this propagation-produced chirp is that each of the leading cycles is progressively narrower in time, according to the dispersive character of the chirp-producing portion of the waveguide buffer. This provides a relatively easy way to avoid the classic problem of cycle skipping, when trying to correlate upstream and downstream transmissions, each of which may suffer different attenuations and waveform distortions. Thus we have an anti-skip feature. With the chirp, one can be quite confident that a particular cycle is indeed the third cycle, for example, and not the second or fourth cycle, by virtue of its period. By adjusting the rod length and rod diameter to wavelength ratio, one can predetermine just how much dispersion will be obtained, i.e., how much the cycle-to-cycle variation will be. For reliable unambiguous identification of a cycle, the period of each cycle of interest preferably differs from its neighbors by five or ten percent. The difference is controllable by the method shown in U.S. Pat. No. 5,139,838, by selecting the operating point along the curve of FIG. 1 of that '838 patent. In contrast to the usual objective of creating a pulse having a very sharp leading edge (rapid buildup), the crystal is mounted or energized to produce a pulse having a low-frequency leading edge and contains distinguishing characteristics that are preserved as they are needed. Note that the change in period occurs in a monotonically-decreasing manner, as a consequence of the dispersion relation depicted in FIG. 1 of the '838 patent, starting at the leftmost or thin rod portion of the function graphed therein. In addition, the low frequency leading portion provides a coarse measure of transit time, refinable by using the subsequent higher-frequency components for higher resolution of transit time. In any given situation, the propagation characteristics of the fluid, and the electronics utilized, will determine how much of the chirped pulse is usable. The greater the portion of the spectrum that survives, the better is the resolution.

The chirp features described here have been demonstrated using a commercially available 500-kHz broadband NDT contact transducer and titanium rods, confirming that implementation is practical using devices and materials manufacturable to commercial tolerances.

The foregoing description illustrates the basic construction and a number of novel implementations of a buffer/waveguide and systems employing such a waveguide in accordance with the present invention. These have utility not just for hot systems, but for a great variety of measurement systems where precise path definition is important. In various situations, it may also be desirable to further refine or tailor the waveguide, and a general discussion of several features and their acoustic properties will be useful for that purpose.

Returning now to the aspect ratio, discussed above, applicant observes that if the shear wave crystal or piezoelement is not perfectly aligned with particle motion parallel to the major surfaces of the buffer, there will be some spurious unwanted generation of Lamb waves. To disperse these waves, one can specify that the frequency-thickness product be such that the $A_0$ wave is dispersive, or that multimodes are present such as $A_1$, $A_2$, $A_3$ etc. However a limitation to this approach is that one does not want the thickness to be so thick that multipaths become a nuisance as they were in prior art devices. Graphs of the phase velocity of Lamb waves vs the frequency-thickness product for steel, for example, reveal that the $A_0$ mode is strongly dispersive below about 1 MHz-mm, while the next asymmetric plate mode, $A_1$, is strongly dispersive between about 1.5 and 2.5 MHz-mm. While there appear to be small regions of frequency-thickness products (e.g. 1 to 1.5 MHz-mm) having little dispersion for the $A_0$ mode, in fact it would be rather difficult to operate with broadband pulses in such regions and not excite symmetrical modes (e.g. the $S_0$ mode) which are dispersive in those same regions. At practical ultrasonic test frequencies for liquids, say 0.5 to 5 MHz, a steel thickness from ~1 to ~6 mm satisfies the foregoing dispersion/multimode objective. Despite being only a few mm thick, it was found that hockey stick shaped waveguides couple adequate signal to the pipe or fluid, that for many situations does not suffer excessively from beam spread laterally in the fluid. Thus, the narrow aperture suffices. Applicant also found that thin sheet metal waveguides are readily curved or bent and still convey with high efficiency, i.e., little or no additional dispersion, the MHz shear waves having their particle motion parallel to the major faces. This result allows long extensions of the wedge region to be curved or bent so as to not protrude excessively, in the radial direction, for those situations where space may be limited, or where radially outward protrusions pose a hazard to passersby. By curving or bending the extension, a low profile is achieved, while retaining the sought broadband transmission characteristic.

For the basic planar geometry (no curves, no bends) illustrated in FIG. 1, the minimum thickness for clamp-on is limited in a practical sense by factors such as buckling under pressure coupling; mismatch between a very thin blade and a thick-walled pipe; or beam spread in a thick-walled pipe which would occur from a line source. Buckling is prevented by limiting the pressure available for coupling, and/or by stiffening, for example, by making the extension or wedge in the form of an I-beam. A very thin blade extracts only a part of the energy available from a piezoelement whose width may typically be on the order of at least 1 mm up to perhaps 10 mm. Most of the experiments reported here were made using crystal widths and buffer widths which were both ¼-inch, or 6.4 mm. However, even with a 25.4-mm diameter shear wave crystal, good echoes were obtained for test sheets under 1 mm thick. A practical guideline may be taken as 0.5-mm minimum thickness, approximately, for buffer lengths on the order of 150 mm, and using SS as the buffer material. If an I-beam or other stiffer shape fits the application, or if overall length is less than 150 mm, thinner minimal cross-sections may function effectively, e.g., 0.25 mm.

Radial Protrusion Relative to Flange Annular Dimension

Although the invention is well adapted to clamp-on constructions, there are numerous applications for the wetted version, e.g. as part of a GC (Gauss-Chebyshev) spoolpiece. Spoolpieces are typically constructed by welding standard flanges to both ends of a section of pipe. For example the GC spoolpiece of FIG. 3B shows 10-inch 150# weld neck flanges butt welded to the ends of a 16-inch long section of so-called 10-inch schedule 40 pipe. The OD of that flange is 16 inches, compared to the 10.75-inch OD for the pipe. The annular difference in this example is 2.63 inches. If one systematically lists the annular differences as a function of nominal pipe size and nominal pressure rating (e.g. 150, 300, . . . , 2500 psi patterns) one finds the difference increases as nominal diameter and pressure increase. For 10-inch 2500# it is 7.88 inches, while for 24-inch 150# it is 4.00 inches (101.6 mm). Where the thermal situation, perhaps aided by fins or cool air flow, allows overall transducer length $X_{OL}$ (wedge region +extension +cap) to be less than the FPAD (flange-pipe annular difference), that will be identified as a preferred dimensional constraint. This constraint has a consequence that when the spoolpiece is rolled along the floor, the transducers do not touch the floor; that is, the flanges radially protect the transducer/waveguide assemblies. One can refer to assemblies satisfying this constraint, to be "low profile" relative to the spoolpiece flange.

As is evident from FIGS. 3A and 3B, it is not always possible to satisfy the constraint $X_{OL}$<FPAD, for a one-piece solid extension. One remedy is to hinge the extension as indicated by the hinges H in FIG. 2F and arrange for a shear wave coupling to be introduced at the butted joint, e.g., pressure coupling. An alternate remedy is to make the extension in two sections, one short enough to satisfy the just-mentioned inequality where the short extension is interpreted as $X_{OL}$. The means the transducer is removable, with part of the extension being removable at the same time. To line up and assist in coupling the shear waves polarized as indicated elsewhere in this specification, the joint may be vee or saw-toothed when viewed from a major face. Vee grooves at 45 deg and having a pitch on the order of one mm are appropriate. One large vee also suffices. Coupling can utilize known liquid couplants (according to Arenberg, 1948, pp. 20 and 22 or other known references cited in Applicant's 1989 book, *Ultrasonic Measurements for Process Control*, Academic Press, section 3.3).

Turning now to one initial motivation for the buffer, namely, the attainment of a clamp-on accurate measurement of the flow for applications such as superheated water in the range 230 to 300 deg C., it is known that the sound speed decreases in this range (McDade et al., *J Acoust. Soc. Am.* 31 (10) 1380–1383, October 1959), as does the density. A plot showing how both decrease as temperature increases appears in applicant's book, *Ultrasonic Measurements for Process Control*, Academic Press, 1989, page 424. At 250 deg C. the density of water is already reduced to some 80% of its ordinary value, dropping below 75% by 288 deg C. At that temperature the sound speed is reduced below 1000 m/s compared to its ordinary value near 1500 m/s, a drop of over 33%. (The McDade et al. data appear in this book too, on p.230.) The embodiments of waveguides appearing in FIGS. 1–1E provide a number of methods for dealing with such large changes in c and still being able to receive signals, or accurately aim the signals to a receiving transducer.

When operating in this range, the characteristic acoustic impedance Z of water is accordingly reduced at 288 deg C. from its ordinary value by the factor $(3/4)(2/3)=1/2$, i.e., reduced 50%. There is some compensating reduction in the sound speed and density of typical buffer/wedge/pipe materials, but one can estimate for 288 deg C., about a 50% (6 dB) reduction in signal due to increased mismatch, compared to room temperature. Detailed calculations lead to graphs such as those in Lynnworth and Chen, pp. 575–578, in the *IEEE Proc. Ultrasonics Symposium*, 1975.

Depending on the fluid pressure, the superheated water might turn to steam at 288 deg C. We can investigate, in what ways might the buffers be configured, to operate as effectively as possible with fluids at reduced density, i.e., density far below one gram/cubic cm, with an objective of one milligram/cubic cm=1 kg/m$^3$, which is roughly the density of ordinary air. This is a density reduction of about three orders of magnitude compared to ordinary water. If one is mainly interested in flow measurement, one should also ask, in what ways the signals differ, after propagating in a compressible low-density fluid that is highly turbulent, compared to an incompressible fluid at comparable Reynolds number, Mach number and flow velocity. These considerations led applicant to recognize that the buffer should preferably not only survive exposure to hot fluids, but also be compatible with several special and sometimes novel signal processing means that may be necessary to extract the sought flow information.

One spoolpiece that utilizes the transducers of this invention, and specifically designed for measuring steam flow, is shown in FIG. 8A. The special mounting gasket shown within the dashed circle 801c in that Figure allows pipe penetration to directly launch and receive signals in the steam, but provides a secure seal and a high degree of acoustic isolation against pipe-borne short circuit noise and ringing. The short circuit is prevented by acoustic isolation between the transducers, or the transducer and pipe, for example by installing soft attenuating gasket material or O-rings under flanged sections, as described in applicant's U.S. Pat. No. 5,515,733, issued May 14, 1996.

In regard to special or novel signal processing as suggested above for highly turbulent fluids, especially compressible fluids, applicant and some of his colleagues recently observed that, besides the well-known nonreciprocity between upstream and downstream propagation, the probability of receiving a strong signal at an arbitrary moment of interrogation, is greater when propagating with the flow, compared to against the flow. In particular, it was observed that at certain fixed pulse repetition frequencies ("prfs"), only occasionally was a clear signal detected. Taking "snapshots" at arbitrary moments usually failed to capture a pulse having high SNR. But when one was captured, it yielded a good measure of transit time, from which flow could be determined. These observations were made on air at ordinary laboratory conditions, flowing in a 12-inch pipe section, having a restriction to generate turbulent flow at up to about Mach 0.1, or 34.3 m/s, approximately.

These observations on the shakiness of the signals, and the inability of relatively conventional averaging protocols to measure the flow velocity with acceptable accuracy, led applicant to several approaches to improve the accuracy and speed of response. These include: i) varying the prf; ii) relate main bang firing to pressure sensed near the region of flow measurement; iii) do not arbitrarily fire an equal number of pulses in each direction; rather, fire only enough in each direction to obtain a probably valid reading having an acceptable standard deviation, where the probably valid reading is not necessarily the arithmetic mean of many pulses of varying signal to noise ratio (SNR), but rather a weighted average, with weight assigned according, for example, to the signal strength S or the SNR of each individual pulse. As a simple and first numerical example, the weight of each pulse utilized can be its SNR. A more discriminatory weighting formula is to assign weights according to a power of the SNR, say the SNR squared. This means a very strong, high SNR pulse strongly influences the average and for that reason, if strong enough, immediately can be taken as the probably valid reading. In that case the processor can immediately produce a final reading, i.e. not take further interrogations in that direction or attempt to develop a measurement within the standard deviation requirement. The disregard for a large number of interrogations based on their poor "quality" (low SNR) is part of this SNR- discriminating method. We shall refer to this weighting method as Darwinian SNR weighting, in the sense that only the strongest signal survives to influence the subsequent calculation of flow. One can say it is a matter of luck, that a particular pulse is launched at a fortuitous time, such that it encounters a minimally-attenuating set of eddies or other sources of scattering, ray bending or other attenuation processes in the fluid. An analogy from optics might be, when driving in a fog, the driver sets and corrects his/her course based on visual clues picked up during moments of relative transparency.

If there are a number of reasonably-strong, moderate- to high-SNR received signals, none of which are so low as to justify discarding them, their transit times can be rms SNR power-weighted as follows:

$$t_{rms} = \sqrt{[t_1(SNR)_1^n]^2 + [t_2(SNR)_2^n]^2 + [t_i(SNR)_i^n]^2}$$

where n=1, 2, $\pi$ or other number, and the t's are transit times. This shall be referred to as rms SNR weighting.

In order to not have to measure against the flow, the contrapropagation method can be modified to measure along a diameter path perpendicular to the axis, a first transit time, from which the sound speed c is determined. Then, along the usual inclined or tilted diameter path, but only in the direction of flow, the velocity of which is V, a second transit time is measured which is a measure of the fluid path P divided by c+V cos θ where θ is the angle of the path relative to the axis. The V is then calculated by an equation of the form $V=Kc^2\Delta t/L$ where L=axial projection of P in the flowing fluid, and K is a meter factor that is intended to take flow profile into account. K is not a constant, in general, and depends on the pipe roughness, Reynolds number Re and whether the flow is steady or unsteady. Uncertainties in K in fact are probably the major motivating factor behind the use of multipath flowcells using midradius chords or the GC chords having axial components.

Compared to liquids, gases under turbulent flowing conditions cause substantially larger modulations of ultrasonic signals, due largely to their greater compressibility. The substantially greater jitter which occurs, especially if frequency is high and propagation is against the direction of flow, may be exploited by applying tag cross correlation methods of flow measurement, and this measurement can be executed over diameter or tilted diameter paths. Applicant applies this realization to a novel measurement system adapted to the particular case of a compressible gas, such as steam at or above one bar, which may flow at velocities of 10–100 m/s in industrial plants, with much jitter and beam drift at the maximum flows encountered. As noted above, a reflection measurement may be used to detect droplets in steam. One system of the present invention further enhances flow detection by adding tag cross correlation, and by detecting and analyzing noise due to the chaotic turbulent medium, and/or noise due to particles such as loose scale carried down the pipe. The general implementation of a four-mode flowmeter with these four modes is disclosed in the commonly-owned U.S. Pat. No. 4,787,252 (1988) of Jacobson et al. The waveguides of the present invention offer particularly advantageous transducer mountings for implementing such a system, and, as applied to fluids such as steam, certain advantages are achieved as follows.

Steam at low flow may be best measured accurately using transit time. As quality degrades (e.g. droplets form), reflection methods supply useful information. Further, as flow approaches and exceeds Mach 0.1 when velocity exceeds some 40 to 50 m/s, the drifted beam can be picked up by axially-displaced transducers, which advantageously may be buffered by the two methods mentioned above, namely, the hockey stick waveguides for oblique incidence and detection, and bundled assemblies of U.S. Ser. No. 477,761 for signal paths at normal incidence. The detected signals are analyzed by the tag cross correlation method, and under these conditions, the high velocity of steam carries the eddies or other characteristic signature of the random medium several diameters downstream before the signature decorrelates and becomes illegible. Jitter may be intentionally increased by using high frequencies and/or by allowing the beam to traverse the steam two or more times before being received. Also, various acoustic short circuit or crosstalk noise contributions may be reduced by any of several techniques, the selection of a technique depending on the measurement mode. Thus, a differential mode technique may be used to cancel stationary noise; averaging may be used to reduce random noise; and quadrature may be employed to reduce crosstalk in the tag cross correlation measurement according to a method of Jacobson et al. published in *Ultrasonics* (May, 1985) pp. 128–132. In one proposed crosstalk-reduction method, crosstalk pickups straddling the receiving transducer are averaged, weighted and phase shifted to yield a signal very similar to the crosstalk between them and which appears intertwined or combined with the signal at the middle receiving transducer. A correlation subtraction scheme due to Yi Liu and the applicant, and described in their above-referenced co-pending patent application, may also be utilized. Another useful technique is to enhance measurements by chaos analysis according to the method of Wayne Hill of the Foster-Miller company, described in U.S. Pat. No. 5,600,073. In each case, the use of the waveguides described above enables well defined signals to be launched and reliably received in the steam conduit.

Turning now to the matter of clamp-on flow measurement in air or other gases conveyed in plastic pipe, we note that first, the particularly low c in most gases poses special problems, and that second, the shear wave velocity in some plastics is within a factor of 2 to 4 of c in the gas. As some numerical examples: taking c in air to be 343 m/s (@ 20 deg C.), the shear wave velocity in some common plastics, according to AIP handbook tabulations, is: acrylic, 1100 m/s; nylon 6—6, 1070 m/s; (low-density) polyethylene, 540 m/s; teflon, 501 m/s. According to Snell's Law of refraction, as the shear sound speed in the plastic approaches c in the gas, the refracted angle approaches the angle of incidence, typically 60 deg for most of our examples herein. For a sound speed ratio of 2 to 1, the refracted angle would be ~23 deg, if the incident angle were 60 deg. This yields ray paths resembling those for clamp-on with steel and water.

In general it should be recognized that the attenuation coefficient α is relatively high for shear in plastics, as well as for longitudinal mode in gases. (Numerical example: in ordinary dry air, at 500 kHz, α=10 dB/ft or ~30 dB/m). Both problems could be mitigated by using frequencies below 500 kHz and perhaps as low as 50 kHz. But using such low frequencies introduces a new problem of a finding suitable generating means for shear waves at this frequency. Applicant solves this problem as illustrated in FIG. 4 by combining a removable source of low-frequency compressional waves, easily grease-coupled or permanent-epoxy-bond coupled to a tube of thin wall in which a symmetrical ($S_0$) wave propagates at a speed close to the extensional velocity, but faster than the shear velocity in that same material. The ratio of the speeds of these two modes, extensional to shear, is $\sqrt{E/G}$ where E and G are the Young's and shear moduli, respectively. That ratio depends on Poisson's ratio $\sigma=E/2G-1$. The refracted mode converted shear in the wedge portion of the assembly of FIG. 4 propagates along an angle calculable in terms of σ. The relationships between Poisson's ratio σ and the refracted angle $\theta_S$ for the shear waves with respect to the normal at the tube/sheet interface, are $$\sigma = \frac{1}{2\sin^2\theta_s} - 1 \text{ and } \theta_s = \sin^{-1}\sqrt{\frac{1}{2(\sigma+1)}}$$

In plastics a typical value for σ is 0.4. The corresponding $\theta_S$ is ~36 deg. By tilting the tubular portion back about 6 deg, a shear wave angle of incidence of 60 deg is achievable, at the pipe or fluid interface.

The assembly can be bonded or molded to a short section of plastic pipe, or implemented in a molded monolithic version.

Further illustrations of methods of achieving removability appear in FIG. 4D. There the tube is replaced by a thin solid rod, which may be magnetostrictive. In that case, the actuating solenoid for the magnetostrictive rod is preferably removable.

Returning now to the more general problem of measuring gas flows, situations occur in which it may be required to cover a very wide range of Reynolds numbers. For example, the conventional contrapropagation method appears best for low flow velocities, with which one associates fairly reciprocal propagation in both directions. Not much noise or beam drift is present. As velocity increases, it may take two, three or four times as many interrogations against the flow, compared to interrogations with the flow, to achieve comparable standard deviations or some other measure of confidence in each direction. This is discused further below, in the section captioned "Further Discussion". Recognizing the greater difficulty in trying to propagate against the flow, consider measuring sound speed c across the duct, perpendicular to the axis of flow, and measuring in addition, only with the flow. This yields flow velocity V approximately as $V=Kc^2 \Delta t/L$ where L=axial distance over which $\Delta t$ is measured, and K is the meter factor, described previously. One way to maintain comparable properties in propagating upstream vs downstream, is to adjust wavelengths to be nearly equal in each direction. If a means is available to select frequency and angle of incidence so as to maintain as nearly constant as possible the product fM sin $\theta_3$ where M=Mach Number, the wavelengths will tend to be matched approximately, and so too the scattering associated with these wavelengths by turbulence of macroscale L', provided the scatter looks the same in each direction. However, bidirectional symmetry is probably an exception, not the rule.

At still higher flow velocities it may not be practical to measure transit times, due to very high levels of turbulence. Here the tag cross correlation method may be used, using crossbow paths or inclined paths one-half to two diameters apart according to known guidelines on spacing for tag cross correlation. Lastly, noise may be listened to, over a spectral band. These last two methods are generally described in Jacobson et al., 1988, U.S. Pat. No. 4,787,252. As mentioned elsewhere above, at high velocities the beam drift method, as developed by Petermann and other investigators from ca. 1960, can now be advantageously applied with the present invention. The hockey stick buffer extends such early concepts to new uses in high temperature fluid measurement systems.

The invention also contemplates improvements in the aforesaid tag cross correlation method. Let us define or characterize a jitter signal as the difference between two successive readings over a given path, in the same direction. The path may be inclined and the direction of interrogation may be inclined in the direction of flow. By taking the difference between two successive readings, the stationary coherent noise due to leakage around the pipe (shown in a phasor diagram in the aforesaid Jacobson et al. 1995 article) ends to be cancelled, and the jitter then represents the nonstationary effects of turbulence and scatterers. The tag cross correlation method can then be executed using jitter observed at the two axially-displaced locations, such as hockey stick locations denoted UU and DD in FIG. 6, but without requiring a physical bluff body, or any body, between them. The axial displacement, or axial distance, may be on the order of the pipe diameter, e.g., ½ to 2 pipe diameters. This tag method with suppression of stationary noise may be particularly well suited to measuring steam flow by clamp-on assemblies (FIG. 8A), where flow velocities of a compressible fluid often exceed Mach 0.1, and make it very difficult to transmit reliably against the direction of flow. This method is advantageous because it uses interrogation paths having no component against the direction of flow. The drift due to the high Mach number is common to both paths and so drift does not degrade the cross-correlation. At very low flow velocities the very same inclined paths can be bidirectionally interrogated to yield the flow velocity with a contrapropagation geometry.

The thin radiator constituting the exit face of the waveguide also offers new opportunities to delineate measurements essentially in narrow planes of measurement, and this in turn provides a way to explore improving the accuracy of the beam drift amplitude-based flow measuring method, which has now been practically abandoned because of its general inaccuracy compared to transit time measurements.

The recognition that it is easier to transmit with the flow than against it, also underlies two other related measurements, namely, (a) the above-mentioned tag cross correlation configuration but with the two paths parallel, inclined to the diameter, and the sensing directions for both paths being in the direction of flow; and (b) determination of the vortex shedding frequency off a strut (bluff body) such as those depicted in Measurement & Control June 1996, pages 228–231, and in Lew, U.S. Pat. No. 5,121,658 issued Jun. 16, 1992, and elsewhere in the prior art. In performing determination (b) we also restrict ourselves to an interrogation geometry as described for (a) but with the signal processing being very simple. In one of the simplest cases one can use a differential amplifier and a bandpass filter to extract the shedding frequency from the two receiving transducers as shown in FIG. 7. When the strut is cast, welded or otherwise formed as an integral part of the meter body, and also including the transducer wedge and extension assemblies, we have another version of a monolithic flowmeter flowcell.

One application of the above described measurements is to provide a flow meter having a neural network method programmed to quickly detect the signal quality in each of a number of modes, and select the best use of the available multi-interrogation modes based, for example, on SNR and/or standard deviation (statistical) criteria, so that the most likely correct answer is provided by the flowmeter.

Returning to a discussion of problems which may be encountered in measuring hot steam, we note (as is well known) that as fluid density reduces, the acoustic short circuit increases somewhat, the fluid-borne signal reduces roughly in proportion to density, and the signal to noise ratio (SNR) reduces similarly, roughly in proportion to density. Unless short circuit can be canceled or prevented by acoustic isolation between the transducers, e.g., soft attenuating O-rings under flanged sections, as described in applicant's above-mentioned U.S. Pat. No. 5,515,733, it will be difficult to obtain useful results down to densities comparable to ordinary air density. However, the special case of a fluid at high temperature that can support 0.5, 1 or 2 MHz ultrasonic waves, that normally is conveyed at high pressure, such as steam at 250 deg C. and a pressure of some 30 bar, or ~450 psig may be more amenable to measurement. In such an environment, instead of some three orders of magnitude below water density, the fluid is only 1.5 orders of magnitude down on the density scale. The speed of sound in hot steam, @250 deg C., is some 50% faster than in ordinary air. Thus, refracted angles, while still small, will be ~50% greater than in air, for the same incident conditions.

In order for a clamp-on transducer system to work in pressurized steam, it will be desirable to have at our disposal, a means for canceling a large percentage of acoustic short circuit noise, or crosstalk. The two-path (X-configuration) of FIG. 2C (or that of FIG. 6 but with the four clamp-on U and D oblique transducers repositioned into the x-configuration) is thus appropriate, operated in a differential mode. The two pipe-borne metal paths (which shall be denoted AB and CD) are nearly identical, and to the extent that they are identical, subtracting the signals at the two receiving transducers tends to cancel crosstalk. The residual signal is the difference between upstream and downstream propagations in the steam. The amplitude of that difference signal is related to the steam flow velocity. If the steam-borne signals are sinusoidal, the phase difference increases with flow velocity and the difference signal will likewise increase with flow, not quite linearly, but in a predictable manner approximately according to the trigonometric identity:

$$\sin \alpha - \sin \beta = 2 \cos(\tfrac{1}{2})(\alpha+\beta)\sin(\tfrac{1}{2})(\alpha-\beta).$$

One can treat $\beta$ here as the phase shift due to flow, in each direction of interrogation. The other angle, $\alpha$, depends on the transit time across the steam path that would occur if flow were zero. One can think of $\alpha$ and $\beta$ as analogous to sound speed and flow velocity, c and V, in transit time flowmeters. If flow velocity is small enough, this method applies, but it would fail for large flows or changing sound speed c.

A better differential path method that still relies on amplitude measurement and still cancels common mode crosstalk, and common mode flow noise, appears in FIG. 6. This configuration responds to flow as sensed in planes symmetrically displaced very slightly about a plane perpendicular to the axis, and utilizes the physically-narrow yet directive aperture of each buffer so that a small drift produces a relatively large change in the differential signal amplitude. The paths are not across the diameter [and thereby differ from Petermann, U.S. Pat. No. 2,874,568 (1959)] but actually across chords, typically many chords that all generate about the same transit time. A sector of the flow is thus compared at each receiving transducer, and the difference provides a measure of the flow velocity. This method is perhaps most suitable for low-cost flow switches and is not based on noise nor on transit time differences of a few nanoseconds or a few microseconds. For ease of explanation the DA (differential amplifier) is indicated as connected to two piezoelements of like polarity. It will be understood that if one of the piezoelements were physically flipped over or rotated 180 deg so as to reverse its polarity relative to the other, the DA can be replaced by a summing device, in the simplest case consisting of a joint between the wires coming off the piezoelements, one flipped 180 deg relative to the other.

A steam flowmeter embodiment as shown in FIG. 8A is constructed with a flange larger than the slot in the pipe or in its retaining member. In this configuration, acoustic isolation is achieved as in applicant's U.S. Pat. No. 5,515,733 (May 14, 1996), and transit time is measured alternately upstream and downstream. Sound speed c may be measured separately across a diameter path using a bundle buffer similarly isolated, said bundle buffer being constructed, for example, according to the construction shown in co-pending U.S. patent application Ser. No. 08/477,761 filed Jun. 7, 1995. Alternatively, the diameter path buffer may be a marginally dispersive waveguide of the type shown in applicant's U.S. Pat. No. 5,159,838 issued Nov. 3, 1992. The larger flange prevents expulsion of the buffer. If adequate isolation is achieved on one transducer of a pair, the other may be welded into the spoolpiece. For fast response, high repetition frequencies are required. This implies damping of the buffer. This can be most easily done near the cooler end, under or within the cap that encloses the piezoelement, usually at a temperature under 100 deg C. As the Reynolds number Re depends on gas density, and the turbulent-flow meter factor K for a tilted diameter path varies 1% per order of magnitude change in Re, it often suffices, with respect to estimating K, to determine the density only approximately. For this purpose the strength of the received signal can be taken as a measure of gas density. This may occasionally require some calibration (to account for transducer aging, for example) and perhaps compensation for sound speed in the gas. Differential path attenuation measurements may add some accuracy improvement to this rough determination of gas density. The path differences between inboard and outboard GC paths may be utilized in this regard, or first and triple transits, if echoes are detectable for one or multiple diameter traverses.

Vortex Shedder Differential Path

As discussed earlier, the buffer as described in connection with FIG. 2E is useful with respect to measuring secondary flow components such as swirl and circulation in a plane perpendicular to the conduit axis. We have also seen, in FIG. 1J, that transmission of ultrasound in a plane perpendicular to the axis can be interpreted in terms of liquid present or absent (i.e., liquid level at a discrete point), and viscosity (based on attenuation of the liquid-borne signal).

If the fluid medium (liquid, high-pressure gas, two-phase medium) conveys ultrasound with adequate transmission level relative to the generally interfering signal conveyed by the conduit, there are several other measurements that become practical. For example, if the medium is a gas, then the gas signal strength compared to the conduit noise level can yield information on gas pressure. Another application is measuring the frequency of vortices shed by a bluff body or other shedder in the stream. In the past, this has been done using one or a pair of transducers just downstream of the shedder, as exemplified by Joy and Colton, U.S. Pat. No. 3,680,375 (1972). However, the transducers apparently had to be wetted, especially if the fluid is a gas such as ordinary air, or else the receiver would be overwhelmed by crosstalk.

FIG. 6 shows several forms of differential measurement where the conduit noise is largely canceled. The small difference between the upstream and downstream (relative to the bluff body) signals is now due to circulation and shedding from the bluff body 602a (a bluff trapezoid) or 602b (a bluff tee) or 601s (a strut, shown in end view). While these differential configurations may not often be accurate enough to measure flow by the contrapropagation transit time method, in the present instance one is only concerned with determining the frequency at which vortices are shed, or the frequency associated with a reversal of circulation direction, cw–ccw. The short circuit signal around the pipe does not contain this frequency information. The frequency of the noise remains fixed. Hence, the combination of differential path (upstream and downstream) followed by frequency analysis yields the vortex shedding frequency f which in turn is related, through the Strouhal number S, to the flow velocity: f=SV/d where d=diameter of the bluff body. In a preferred embodiment the strut would be welded into the pipe, either at the factory or in the field via a hot tap procedure. The transducers would preferably be totally outside the conduit pressure boundary, i.e., clamped on. This avoids the usual electrical feedthroughs from pressure or temperature sensors that are ordinarily used to sense $f$. Again, both inclined paths are interrogated in the direction of flow, rather than against the flow. Depending in part on crosstalk arrival time relative to fluidborne arrival times, the two inclined paths may be interrogated simultaneously (the preferred way, if practical) or else interrogated one at a time in fairly close succession, ~1 to 10 ms apart.

The prior vortex shedder ultrasonic flowmeter art includes plastic bodies containing a cast-in bluff body and external diametrically opposed ultrasonic transducers, both of which are downstream of the shedder. (Example: Tokico Ltd of Kawasaki City, Japan, Model GS-F3030E ultrasonic vortex flowmeter, PEEK series, made of poly ether ether ketone resin.) This apparently operates much like Joy and Colton's basic vortex shedding ultrasonic flowmeter, U.S. Pat. No. 3,860,375 (1972). Additional prior art includes H. S. Lew's U.S. Pat. No. 5,121,658, issued Jun. 16, 1992, and a recent summary article on vortex shedding flowmeters in general that appeared in the magazine m&c (Measurement and Control) June 1996, page 228–231. The present configuration may use conventional or unconventional shedders, preferably with a strut diameter $d_{strut}$ less than 25% of the pipe diameter. It is reported in the literature that noise is one of the principal limiting factors in vortex shedding flowmeters. The differential method of measurement embodied in FIG. 6 tends to cancel noise and respond only to a preselected band of frequencies associated with the calculable vortex shedding frequency, for a given $d_{strut}$ and a known range of flow velocities $V_1$ to $V_2$.

A more symmetrical and therefore better way to compare upstream vs downstream circulation about the strut 601s, is depicted in the bottom right-most portion of FIG. 6. Here upstream and downstream measurements are each executed in planes perpendicular to the axis. The exit faces 603a,b are contoured to match the pipe curvature. The cw and ccw interrogations (604a&b, respectively) at upstream (~U) and downstream (~D) locations tend to cancel any swirl effects. The switch 605sw, when closed, causes the cw and ccw interrogations to be launched simultaneously. The differential mode then more completely removes common mode noise and yields a difference signal indicative of the vortex shedding frequency. This yields, perhaps for the first time, a totally external way to sense the vortex shedding frequency in a thick-walled steel pipe, and in a manner extendable to high temperature or to cryogenic temperature, all with one device having no electrical penetration of the pressure boundary. Note that by measuring circulation fore and aft, so to speak, or at least the difference in circulation Γ fore and aft, one can measure flow even before actual shedding occurs. As long as there is lift, there will be some Γ. This method will be referred to for brevity herein as the differential vortex method, or DVM. In the end view the fore and aft pictures of the transducers are superimposed and may be thought of as similar to the U and D interrogations at transducers 606 and 607.

An interesting detail in the preferred refracted angle exists for the DVM, compared to contrapropagation axial flow measurements. For the DVM we want to measure along a diameter or near-diameter path perpendicular to the vortex street or vortex sheet. In the illustrated geometry, this means a small angle of incidence is preferred. But how small? According to Arenberg (1948), incident shear is not mode converted for materials having a Poisson's ratio greater than ~0.2 if the angle of incidence exceeds ~35 deg. Knowing there will be some beam spread about a nominal central angle of incidence, suppose we take 45 deg as a central angle of incidence, and plot the beam pattern for two cases: steel/water, and steel/air. From such a plot applicant found that the refracted rays are closer to the diameter for air than for water. In that sense the DVM appears more appropriate for gases than for liquids. When setting up, the contoured clamp-on transducers can be rotated circumferentially with respect to the strut (bluff tee) to determine the best angle of interaction with the shed vortices, from 0 to 90 degrees.

As the object is to filter out the vortex shedding frequency, when vortices are shed, and to sense lift, at low flow velocities prior to onset of shedding, sensing along a path exactly perpendicular to the sheets is not an absolute requirement. This means signal strength and SNR are probably more important, in general, than creating a refracted angle very close to zero (diameter path). Liquids are easier to measure because of the relative ease of achieving high SNR by operating up in the MHz range. For gases, frequencies of approximately 0.5 MHz are typically required. But as measurements in gases are not required against the direction of flow, one may go to higher than usual interrogation frequencies, e.g. 1 MHz at least for small pipes and perhaps as large as 300 mm diameter for high gas pressures, and thereby obtain high SNR in a gas clamp-on system configuration. As applicant has already confirmed effective measurement of the flow of water at 500 kHz, 1 and 2 MHz in ten-inch SS pipe with the hockey stick transducer, this means that one solution, with the operating frequency as high as 500 kHz or perhaps 1 MHz, is feasible for two problems, DVM for liquids and for gases.

Chirp and GC Multipaths

Referring again to FIG. 3A showing wetted GC transducers, note that, in a typical arrangement, the inboard paths are of identical length and the outboard paths are identical but of shorter length. Suppose all four upstream transducers are connected electrically in parallel, and likewise for the four downstream transducers, with the further stipulation, that each path has transducers at least one octave different from any other path. One solution is the four frequency set 0.5, 1, 2 and 4 MHz. Suppose now that the system is interrogated by a chirp, sweeping from 0.5 to 4 MHz in sawtooth or stepped fashion. Passing through the resonant neighborhood of each pair in succession, measurements predominantly from one path, and only that path, would be made in successive intervals. If the chirp were re-chirped once per second, each path would be interrogated once per second. The receive window can be preset to toggle between the two expected ranges of inboard and outboard transit times as each anticipated resonance is utilized. Or the window can be wide, covering all paths, and the frequency selection (resonance) of each pair of transducers can be relied upon to separate information for each path in succession. Thus we have a frequency domain variant of the system described in Applicant's May 14, 1996 patent (which launched N signals simultaneously for reception at different times), now with frequency discrimination instead of or in addition to temporal separation. The approximately 6-mm width of the hockey stick transducers (all of identical shape, except for slightly dissimilar wedge thinning to regulate the depth of insertion into the oblong GC slots) satisfies the broadband propagation requirements for 0.5 to 4 MHz. This system may also be implemented by using a set of lamp-on transducer assemblies which are identical in all respects except for the frequencies of their piezo crystals.

Temperature Gradients Along the Path in the Wedge and Extension

The weighted average temperature can be determined by measuring local temperature T at the several tabs TC1, TC2, . . . illustrated in FIG. 1 and 1A. If the gradient is not too severe one can simply take the linearly weighted average $$T_{avg} = \frac{x_1 T_1 + x_2 T_2 + \ldots + x_i T_i}{\sum x}$$

For steel, in which sound speed does not change too much with temperature, changing only about 5% up to 300 deg C., experience will dictate which tab yields a T pretty close to the true average T, for particular circumstances. For a linear gradient the midpoint would yield that average T. If the change in c is estimated as 5%, a small error in average temperature might translate to a $t_w$ error of 1%. This is one microsecond if the real buffer delay, denoted $t_w$, equals 100 μs.

A reference reflector such as the slot from Q1 to Q3, parallel to the incoming shear wave-front, yields an echo whose round trip time equals the buffer delay. Small hole Q4 indicates the transit time and hence the average temperature in the extender portion above the wedge.

Plastics will have a greater fractional coefficient of sound speed with temperature, (1/c)dc/dT. Ceramics and refractory alloys will have a lesser (1/c)dc/dT, near zero in some cases, e.g., fused quartz Graphite also has a near-zero (1/c)dc/dT Removability Versions for a Hybrid Construction Referring now to FIG. 2F, let us consider the concept of a hybrid assembly consisting of a removable transducer, and a plug permanently fixed to a pipe and thereby forming part of the permanent pressure boundary. The hybrid actually serves two purposes in the set of illustrations comprising FIG. 2F. First, removability is achieved. Second, preferred refracted angles (30 deg) are achieved, that would otherwise not be possible for the pipe and liquid presumed in the following example (steel, water).

Let us first consider as the objective, interrogation along a spiraling triple midradius path. Transducer sites are generally in the axially displaced positions marked $z_1$ and $Z_2$. Because of limitations on refraction imposed by Snell's Law, that path is unreachable by clamp-on if the pipe is thick and of substantially greater sound speed than the liquid. For example, the shear wave velocity in steel is more than twice the longitudinal wave speed in water, and refracted waves at 30 deg are not practical.

The hybrid solution to this problem is depicted in FIG. 2F, with introduction of a plug having a shear wave sound speed $c_2$ nearly equal or identical to $c_3$, the sound speed in the liquid. Some forms of graphite, phenolic and tin, have shear wave velocities near 1500 m/s. Silver and platinum are two others, but too expensive for most applications. If the shear wave velocity in the plug exceeds the longitudinal velocity in the liquid by 10%, the angle of incidence must be compensated accordingly, according to Snell's Law. This means angles of incidence may have to increase from 30 deg (for matched velocities) to about 33 deg. Sometimes beam spread suffices to make this compensation, which means the axis of the plug can be close to but need not be exactly according to the value calculated by Snell's Law.

In FIG. 2F the plug 10h and removable member 10j have corresponding flanges with aligned centerlines representing locations of bolt clearance holes and tapped holes for connecting these elements together. The longitudinal wave radiating into the liquid is indicated by the arrow to be along the y-axis, pointing downward, in this end view. After three midradius helical traverses the ray would approach the pipe wall at 30 deg to the x-axis. A plug and removable member again solve the refraction problem, but they are installed rotated 60 deg clockwise relative to the first orientation. The two transducers on the left side are mounted by hinge asssemblies H to oriented buffer/waveguides on the spoolpiece. Each hinge H includes a removable hinge pin 10hp so that the transducer/hinge plate outer member can be completely separated and removed. Optionally, sealing gaskets may be provided to seal around the mating surfaces to preserve their cleanliness. Screws hold the parts together and provide coupling pressure for effective transmission of shear waves.

Even if the two parts are of different sound speeds, or even if there is a strong temperature gradient in this region, the ray proceeds without refraction (without bending), straight across the interface, which is normal to the gradient. If the two parts are of equal speeds, the interface may be sawtoothed.

Obtaining the midradius chords in water by clamp-on, without recourse to an insert plug, is also possible in a steel pipe if the wall is very thin, or in a plastic pipe. The narrow wedge of the present invention would then be oriented on the periphery of such conduits.

By bringing the Gauss-Chebyshev method to a plastic pipe, and perhaps with reinforcing to maintain the pipe geometry constant by adding ribs or an extra encircling flange, a substantial reduction in cost of a high-accuracy spoolpiece is achievable. For air-conditioning ducts and other low-pressure air applications, a cast plastic spoolpiece with thin transducers and thin reflectors minimally penetrating the pressure boundary offers an improved way to measure flow accurately yet inexpensively. In such applications, if crosstalk is a problem, the crosstalk isolation method using silicone O-rings may be advantageously adapted to the rectangular cross-section of the present thin waveguides, installed through flanged nozzles. The sheet metal GC spoolpiece made from the stamping shown in FIG. 3C is another way to achieve accuracy at minimal cost.

Applicant expects that as data are gathered and analyzed, along with advances in CFD (computational fluid dynamics), it may become practical to use just tilted diameter paths and compute or look up the meter factor K as a function of nonideal inlet conditions. This would allow further cost reduction, as off-diameter paths for profile compensation would become unnecessary and secondary flow components would not need to be measured directly. One way to acquire such data would be to use spoolpieces similar to those illustrated, wherein tilted diameter and other paths are included. Again referring to the sheet metal stamping of FIG. 3C, diameter paths are to be obtained by installing transducers (hockey sticks) through ports X, XX, X', XX', and off-diameter paths are to be obtained using the other oblong ports A, AA, . . . D, DD. Reflectors installed within slots R subscripted according to the transducer ports A . . . XX' are also to be used in conjunction with their respective transducer pairs. For the GC arrangement in a circular spoolpiece, the construction lines defining the oblong slot centerlines are parallel and spaced equidistantly at intervals of πD/10 corresponding to 360 deg/10=36 deg intervals between GC paths as seen in the end view.

Monolithic Sheet Metal Extensional Tube to Shear Wedge

A particularly low-cost method of making one monolithic version of this invention is shown in FIG. 4A and 4B. A sheet metal preform, of uniform or stepped thickness, typically 1-mm max thickness and resembling a squared-off fuselage and wing section of a plane, can be formed as indicated in that figure, to act as a monolithic tube and wedge assembly. This assembly is based on Applicant's experiments. These experiments showed that 0.5 or 1 MHz compressional pulses, propagating in a 2- to 3-inch length of ½-inch diameter ×0.035 inch wall thickness SS tube in a mode resembling extensional waves or the $S_0$ mode efficiently leaked off as fairly-broadband shear waves into an adjacent soldered wedge section of the same or similar thickness. The shear angle is calculated as was done for plastic above, but Poisson's ratio for SS is about 0.3, compared to about 0.4 for plastics, so the exact angles differ somewhat. For SS the angle is larger, nearly 39 deg. In these tests it was found that the source of waves, a commercial NDT broadband longitudinal contact transducer, could readily be coupled by a gel to the tube end. Thus the extensional portion provides for easy removability of the actual electroacoustic transducer. If the SS tube is replaced by a magnetostrictive tube or solid rod as FIGS. 4A or 4D, the excitation coil may be a removably mounted coil.

One other interesting combination of two modes will be mentioned here. It is the combination of Rayleigh and shear. An example is shown in FIG. 4C. Rayleigh waves propagate nondispersively in thick plates. Hence a Rayleigh buffer may be envisioned as an extended source of waves at the Rayleigh velocity $C_R$. The Rayleigh buffer does not yet appear to be as generally useful for industrial systems and process measurements as the shear buffer waveguide described herein, but there are occasional situations where it may be advantageously combined with the shear buffer. The Rayleigh buffer wraps more easily around the circumference of a pipe, than does the shear buffer. It can also be used an extended source in the axial direction, making line or arc contact. As an extended source or extended receiver, it might replace several separate hockey sticks for applications where the exact arrival point is unpredictable. Unlike the hockey stick, however, the Rayleigh buffer must generally be made of a material different from that of the adjacent pipe, so that its velocity would exceed that of shear waves in the pipe wall by some 5 to 15%, to couple efficiently to shear waves at useful refracted angles. SS Rayleigh buffers could work with brass pipe; fused silica buffers could work with SS pipe. By "could work" is meant, the necessary velocity ratios are achievable with such materials combinations. Applicant has made preliminary tests with these particular combinations at frequencies around 1 MHz.

By way of further discussion, the following are useful analogies to explain why SNR-weighted propagation measurements and SNR-weighted duty cycles ought to yield more reliable information in less time than previous methods.

It is intuitively obvious that it is more difficult to try to run into a sandstorm, against the wind, than to run with the wind. For a sound wave that is of a wavelength that can be strongly scattered by a particular scale or intensity of turbulence, or for a sound wave having wavefronts that can be rotated by eddies or velocity gradients, it seems reasonable to expect such effects to be more pronounced when the wave heads into the wind, rather than heads in the same general direction as the wind. At high Mach numbers the relative velocity with the wind vs against the wind, shows a significant direction-dependence. Hence the scale of turbulence relative to the wavelength would have a significant direction-dependence. While a rigorous explanation of attenuation by turbulence, as a function of wave direction relative to flow direction (wind direction) is probably not available now, it may suffice that numerous investigators have reported their observation, on the greater difficulty in obtaining good signals against the wind, compared to with the wind. These observations occurred in CEM applications [continuous emissions monitoring, summarized in J. Matson and R. Davis, Ultrasonic Flowmeters Offer Reliable Solution to Stack Monitoring, I&CS, 67 (2), pp. 67–69 (February 1994)] and in earlier studies. An illustrative schematic example appears in the Applicant's book, page 150, for the case of Mach zero and Mach one. In trying to apply the present invention to steam or other gases at high flow, similar turbulence-induced nonreciprocity may be expected. Related discussion appears in the cited book, pp. 145–150.

In a fluid-conveying pipeline, the fluid traffic, or fluid flow rate, is perhaps uniform on a long-time-averaged basis (seconds) but nonuniform on a short time scale (milliseconds). This is known from earlier studies of tag cross-correlation. Ultrasonic waves transmitted at axially displaced positions about ½ to 2 diameters apart encounter modulating effects due to turbulence, that can be cross-correlated. [(Non-ultrasonic measurements also exhibit correlatable jitter; a suitable text on this more general aspect may be Beck and Plaiskowski, *Cross Correlation Flowmeters—Their Design and Application*, Hilger, Techno House UK (1987).] These modulations eventually become dispersed. That is why one typically looks at two locations not more than about 2 diameters apart. The modulations imposed on ultrasonic pulses occur in time (or phase) and amplitude. A corollary, apparently not recognized nor used previously, is that if the signals transmitted across turbulent flow vary from instant to instant, there must be certain times at which the signals propagate with less modulation, i.e., less attenuation caused by turbulence, than at other times. A special case, is when the turbulent eddies of interest are specifically those created intentionally by a bluff body, and where the modulation occurs at a frequency proportional to the flow velocity. This too has a corollary, and again, apparently not recognized nor used previously. Between the vortex sheets there are lulls when the ultrasonic signal can get across the path with little or no rotation, scattering or, in general, with little attenuating modulation effect.

Relation to Accuracy and Response Time and Their Product

Most flowmeter specifications have as a major component, the accuracy. In some cases the time in which the stated accuracy is to be obtained, is also listed. For example: 1% accuracy in a 1-second response time. Obtaining 1% or better accuracy in 10 seconds, may mean the answer came too late to be useful. On the other hand, getting an answer too quickly, say in 0.1 second, may mean the answer is unreliable. In some respects ultrasonic flowmeters have a performance characteristic where if the error magnitude were plotted long they axis, and the square root of time were plotted along the x axis, the performance would be approximated by a hyperbola in the first quadrant, asymptotic to x and y axes. Roughly analogous to the Heisenberg Uncertainty Principle, if we specify time too short, the uncertainty in flow must be large. Conversely, if we require exceedingly small error, a very long time is required to obtain it.

The present concept of varying the measurement or interrogation time spent in each of two different directions with respect to the direction of flow, as a function of the SNR, is an attempt to optimize the joint product of accuracy and response time with respect to user requirements. The signal amplitude S may be taken as the amplitude of the strongest signal within a predetermined time window, provided certain other requirements are met (e.g., frequency, signature). The noise may be taken as the waveform, usually its amplitude N, at a point or region just prior to the onset of the signal. The "onset" of the signal (tonset) in turn may be taken as the point in time at which the signal's envelope, extrapolated backward in time, intersects the time axis. The "envelope" may be piecewise linear, Gaussian or other common shape associated with analog- or digital-filtered signals. The "noise region" just prior to the signal may be taken as an interval containing one to ten or more cycles at the center frequency of the pulse. That interval will preferably be adjusted according to pulse shape and other conditions imposed by the application. It may be advantageous to set that interval equal to the width of the transmitted pulse. Another convenient choice is to set the noise-sensing interval equal to the time it takes for the received pulse to build up to its maximum value.

Determining $t_U$ & $t_D$ by the MRI/S [Maximum Reliable (SNR-Weighted) Information per Second] Method (1) Method defaults to an equal number of interrogations in each direction as transmission characteristics become the same in U & D directions.
(2) Method weighted-averages acceptable $t_U$'s & $t_D$'s in the absolute maximum desired response time $t_{abs.\ max.\ goal}$ and reports σ & SNR information for that interval.
(3) Method weighted-averages in a shorter or longer time $Ut_{abs.\ max.\ goal}$ where $1 \leq U \leq 10$ where U is taken as a measure of the uncertainty in the measurements. U may be calculated as a function of SNR. Examples: (a) U=1/SNR. (b) U=σ/SNR. (c) U=constant * ln $(1/SNR)^n$.
(4) Weighting is a function of SNR.
(5) As $(SNR)_D$ is usually $\geq (SNR)_U$, the fraction of time spent in upstream attempts is usually $\geq$ the fraction of time spent in downstream attempts.
(6) Method may control or adjust transmitted power, frequency, spectrum, coding or modulation method, and receiver processing modes associated with such transmissions, as a function of observed average or peak SNR, signal strength S, ratio of number of acceptable received signals $N_{OK}$ to the number of attempts $N_{TRY}$, that is, $N_{OK}/N_{TRY}$, in upstream (U) and downstream (D) directions.
(7) It will be understood that where our examples use SNR, we could just as well have used S, as a simplification. In some applications, the principal noise N is due to acoustic crosstalk and can be measured during startup or during regularly scheduled maintenance. Then S can be specified as a practical multiple of N, e.g., 5N, 10N, 30N, or 50N, etc.

Key Steps:

1.0 Transmit downstream only until a good reliable result for $t_D$ is obtained, or until the time $K_D t_{abs.\ max.\ goal}$ is used up. $K_D$ may equal 0.5 initially but be adjusted as a function of $S_D$, $S_D/S_U$, $α_D/α_U$, or as a function of $SNR_D/SNR_U$. For example, $K_D$ can be set to the value $SNR_U/SNR_D$. Report $t_D$, $σ_D$, $<SNR_D>$, PSD (power spectral density) information, and/or other significant statistical information.

2.0 Transmit upstream until a good reliable result for $t_D$ is obtained, or until $K_D{}^t{}_{abs.\ max.\ goal}$ is used up. $K_D$ may equal 0.5 initially but be adjusted as a function of $α_D/α_U$, or as a function of $SNR_D/SNR_U$. For example, $K_U$ can be set to $K_U=1-K_D=1-(SNR_U/SNR_D)^n$ where n=1, 2, π or some other number. Report $t_U$, $&_U$, $<SNR_U>$, PSD (power spectral density) information, and/or other significant statistical information.

3.0 In cases where it is exceedingly difficult to measure time (or amplitude) against the flow, measure in two different directions neither of which has components against the flow. For example, measure perpendicular to the flow and with the flow. Or measure at 15 degrees and 30 degrees to the normal, inclined differentially in the direction of flow.

4.0 There can be multiple and potentially very fast routes to the final answer for $t_U$ or $t_D$, depending on SNR's. One possibility for a single-shot decision is provided, for example, by setting $SNR_{single-shot}$ to a value, say 10. Then, whenever a pulse is detected that has a SNR$\geq$10, its arrival time is immediately taken as the arrival time for that direction, say $t_U$. Then the measurement advances or toggles to the other direction, to obtain $t_D$.

5.0 The value for $SNR_{single-shot}$ may be made responsive to changing propagation conditions by setting It equal to the average of, say, the three highest SNR's in the three most recent measuring intervals.

6.0 In multipath applications, the U-D process may proceed in symmetrical or random fashion until all paths and directions have been interrogated. Then the process repeats.

One last analogy may be useful to explain the use of the new transducers under highly turbulent flow conditions, for example high-velocity gas flow or some liquid flow conditions, especially two-phase or multi-phase flow.

Let us refer briefly to sound propagation in solids, and in particular to a well-known graph showing the frequency-dependence of attenuation in polycrystalline steel subject to various heat treatments, due to Babikov, 1960, cited in Applicant's 1989 book, Ultrsonic Measurements for Process Control, on page 76. That graph shows how sound absorption increases with frequency in a nonlinear manner, and further, how the absorption depends on the microstructure (quenched vs normally annealed vs overheated). Other authors have similarly related attenuation versus frequency to the grain size, texture or microstructure. It is also well-known that crystalline materials are anisotropic. This term is usually applied to the variation in sound speed along different crystal axes. In inhomogeneous materials such as fiber-reinforced composites, it is well-known that attenuation is a function of direction too. So we can take anisotropy to include direction-sensitivity of propagation in general, meaning sound speed and/or attenuation.

It is also well-known that scattering depends in general on the ratio of the scatterer cross-section to the ultrasonic wavelength, and also on the direction of incident and scattered beams. If we represent the size of the scatterer by $σ_x$ and the ultrasonic wavelength by λ, scattering will depend on some power of their ratio $σ_x/λ$.

Now in a turbulent fluid, for example a gas at Mach 0.1, the effective wavelength is shorter into the wind by 10%, and longer with the wind by 10%. The difference is 20%. It seems plausible that scattering into the wind vs with the wind will be different, higher into the wind, because the shorter wavelength is scattered more, just like a 20% higher frequency is scattered more in the polycrystalline solid. (12 MHz vs 10 MHz in Babikov's numerical example for steel, with the absorption being about 1 dB per cm, or 100 dB/m for normally annealed steel, for these two frequencies.) The scatterer size in turbulent fluids is the scale of turbulence. The shape of the scatterer, however, may be more important than the difference in wavelengths in the two directions.

This model predicts less attenuation with the wind, than across it, perpendicular to the axis of flow; and less attenuation perpendicular to flow, than against the flow. We can express this as $α_{upstream\ direction} > α_{perpendicular\ direction} > α_{downstream\ direction}$. This leads to support for the measurement of very turbulent flows using two paths, one perpendicular to the flow and one in the direction of flow. It is convenient to use the perpendicular path to measure sound speed and crossflow anyway, and now we recognize another reason, to extend the range of measurement to higher flow velocities. At relatively low flow velocities, the upstream and downstream attenuation coefficients will not differ too much, and one can use the conventional tilted diameter diagonal path interrogated bidirectionally. As the flow approaches Mach 0.1, depending on the path length and ultrasonic frequency, and turbulence $(σ_x/λ)$ it may become necessary to shift to the perpendicular diameter and downstream directions only, and abandon the upstream direction of interrogation. Although the Δt effect will be only half of the bidirectional Δt, at high Mach numbers, it will be large enough to measure to adequate precision. It will be better to obtain a good reliable measure of transit time, rather than fight the wind and get an uncertain measure of twice as much Δt. By measuring α(f), the frequency-dependence of absorption, one obtains a measure of the scale of turbulence.

Steam flow referred to in connection with FIG. 8A, provides an interesting example of a fluid that presents the flowmeter designer with several technical difficulties simultaneously. These include (1) high temperature, (2) high pressure, (3) high flow velocity, (4) high Mach number $M_F$, and (5) if droplets are present, a second phase that scatters ultrasound differently according to the direction of interrogation. This last complication is recognized to be a consequence of the shorter upstream-directed wavelength $\lambda_U$ compared to the downstream-directed wavelength $\lambda_D$. For $M_F$ on the order of 0.1, it is now recognized that upstream and downstream attenuation coefficients $a_U$ and $\alpha_D$ differ, with a strong possibility for $\alpha_U >> \alpha_D$, when the fluid conditions include discrete scatterers like droplets in steam, air bubbles in water, or non-spherical asymmetric turbulent eddies having a mean scale of turbulence, $\sigma_x$ in a single-phase compressible fluid.

Referring again to Babikov's data graph, we note that not only does the absorption (let us call it $\alpha$) increase with frequency f, it increases faster at higher f. This is seen in the $\alpha$curves being shaped concave up, and with more curvature evident for the "overheated" and presumably larger grain size with respect to wavelength.

The present interpretation leads us to several design guides: (1) If one wants to transmit into the flow (i.e., against the direction of flow) use a shorter L and smaller $\theta_3$, according to f and path length P, for a given $M_F$. (2) Since $\alpha$ depends on $f^n$, $n \geq 1$, the larger the bandwidth of the transmitted signal, the more distortion is to be expected, more so against the flow than with the flow. (3) As turbulence, P and f increase, individually or jointly, consider that $\alpha$ may actually decrease as $\theta_3$ increases because $\lambda$ is effectively "stretched" by increasing $\theta_3$. The object is to minimize in ($\alpha_D P$). (4) There is a tradeoff between time resolution and 1n ($\alpha_D P$). (5) The code may have to be modified to reduce bandwidth, especially if one strives to correlate U and D interrogation signals. This poses a dilemma, because a broadband code containing lots of information is ordinarily the preferred way to distinguish a signal buried in noise. One compromise solution may be to use a narrow band code transmitted twice, at two close but different carrier frequencies to avoid cycle skip ambiguity to which narrow band signals are more susceptible.

Several remedies may also compensate for anisotropic attenuation at high flow. To the extent that $\alpha_U >> \alpha_D$ merely because of wavelength $\lambda_U < \lambda_D$, one remedy is to transmit upstream at a suitably lower frequency. If scattering were directly proportional to the ratio $\sigma_x/\lambda$, the remedy numerically would consist of maintaining the frequencies proportional to $c \pm M_F$, with the lower frequency oriented into the wind, higher frequency with the wind. Several particular solutions emerge. One is to set $f_U/f_D = 1/(1+M_F)$. Another is to set $f_U/f_D = \frac{1}{2}$ or $\frac{1}{3}$. Integer relations may take advantage of piezoelectric transducer resonances, and/or provide opportunities to properly interpret arrival times for under sampled waves. Codes may be adapted easily to U and D directions when these directions have integer f relationships. By this, it is meant that at the higher (for example) doubled frequency, e.g., 2 MHz, the code might be 110000111100 corresponding to, at the base carrier frequency, 100110 at f=1 MHz. In this way the envelopes of the two different coded waves would resemble each other, even though different carrier frequencies were transmitted into the wind (against it), and in the opposite direction. The attenuation would be influenced largely, although not entirely, by the wavelength corresponding to the carrier frequency. The bandwidth also influences the attenuation and pulse distortion, due to the frequency dependence of attenuation by scattering or other attenuative processes.

These last ideas can be summarized by the rule that one should try to maintain as nearly constant as possible, the product fM sin $\theta_3$, where $\theta_3$ is the refracted path angle in the fluid.

If the refracted angle is less than about 10 or 15 degrees, one can replace sin $\theta_3$ with $\theta_3$, leading to the simple rule: try to maintain as nearly constant as possible, the product fM $\theta_3$, so that fM$\theta_3$~const. This equation can be thought of as showing the connection among several versions in the group of figures following FIG. 1, wherein there are shown a multiplicity of piezoelements (f), a multiplicity of angles that may be responsively selected according to M, and a multiplicity of spacings to pick up signals refracted as a result of being launched at different incident angles, in turn due to use of three differently angled chamfers or a curved reflecting "chamfer".

The foregoing description sets forth basic features of the present invention, and elaborates on a number of details adapting the basic construction to both general and highly specialized ultrasonic measurement configurations, in a number of environments which may include high temperature, changing or unpredictable fluids or flow conditions, and other factors. The waveguides of the present invention are well adapted by their signal propagation and coupling properties to both active lauching of ultrasonic signals, and to reception of lauched signals or even passive monitoring of intrinsic noise in a fluid system. In measurement systems according to the invention, an individual waveguide may perform more than one function, and indeed will commonly operate both as a sending and a receiving transducer, and may be paired with one or more other such transducers to within its beamspan. The invention being thus disclosed and described, other modifications and iations will occur to those skilled in the art, and these modifications are considered to be within the scope of theinvention and its equivalents, as defined by the claims appended hereto.

I claim:

1. A waveguide for interposition between an ultrasonic wave source and a fluid-bounding wall to couple ultrasonic energy from the source on one side of the wall into fluid on the other side of the wall to effect a measurement thereof, said waveguide having a guided path centerline with a length dimension along a direction of signal propagation within said waveguide, and having a thickness dimension and a transverse dimension, the length dimension being substantially greater than the thickness dimension, the ratio of the transverse dimension to the thickness dimension defining an aspect ratio, and said waveguide comprising a standoff portion, a middle portion and a seat said standoff portion having a first face oriented for coupling to the source to propagate energy therealong to said middle portion, said middle portion including a bounding edge lying at an angle between 0 and 45 degrees to the direction of propagation for directing energy propagated along said standoff portion toward said seat portion, and said seat portion extending with an exit face to radiate along a path through the fluid energy received from the middle portion, wherein said bounding edge and said exit face lie at an angle with respect to said first face, and wherein said standoff portion, said middle portion and said seat portion each have a cross-section such that ultrasonic energy applied to the standoff portion is directed into the seat portion to propagate non-dispersively as shear wave energy and radiate from the exit face as a narrow beam along a defined path.

2. A waveguide according to claim 1, wherein said standoff portion has a length effective as a thermal standoff to thermally protect a transducer coupled at the first face.

3. A waveguide according to claim 1, wherein said standoff portion couples to plural sources which operate at different frequencies spanning at least two octaves.

4. A waveguide according to claim 1, wherein said cross-section is a substantially rectangular cross-section with an aspect ratio greater than about 4:1.

5. A waveguide according to claim 4, wherein said middle portion and said seat portion lie in a common plane with said standoff portion.

6. A waveguide according to claim 4, wherein said middle portion and said seat portion lie in a common plane and said standoff portion extends out of said plane.

7. A waveguide according to claim 1, wherein at least one of said bounding edge and said exit face is a curved surface.

8. A waveguide according to claim 1, wherein said waveguide is formed of a plate and said standoff portion lies in a plane extending at a dihedral angle to said seat portion.

9. A waveguide according to claim 1, wherein said waveguide is formed of a folded sheet metal stamping.

10. A waveguide according to claim 1, wherein the bounding edge is oriented so that energy redirected to said exit face is coupled from said exit face along a selected path angle into fluid when attached to a conduit.

11. A waveguide according to claim 1, wherein the seat portion includes material selected to couple said energy at a sound speed effective to control refraction angle of the energy radiating from the exit face.

12. A waveguide according to claim 11, wherein said material is different from material of the standoff portion.

13. A waveguide according to claim 1, wherein the bounding edge includes plural reflecting faces arranged at different angles to each other so as to redirect the energy at plural different angles of incidence upon said exit face.

14. A waveguide according to claim 1, which includes a plate, and further comprising at least one topological feature formed in the plate for providing a reference echo as said energy propagates in the plate, said feature being located so as to not disperse energy in the plate traveling to the exit face.

15. A waveguide according to claim 14, wherein the topological feature is selected from among a groove and a hole.

16. A waveguide according to claim 14, wherein said seat is configured to form a second reference echo including energy internally reflected from said exit face whereby amplitude of said second reference echo indicates coupling efficiency of said exit face.

17. A waveguide according to claim 16, further comprising means for processing said first reference echo to determine at least one of a function of signal path length in said waveguide, and coupling efficiency of said exit face.

18. A waveguide according to claim 1, wherein the standoff portion is a cylinder which propagates energy along an axial direction, and said bounding edge is an edge of said cylinder which couples said energy as shear waves into the seat portion.

19. A waveguide according to claim 18, wherein said cylinder is a tube having a wall sufficiently thin to propagate said energy non-dispersively.

20. A waveguide according to claim 18, wherein said cylinder is a magnetostrictive rod configured for generating said energy upon application of a magnetic field thereto.

21. A waveguide according to claim 18, wherein the standoff portion is a thin cylinder which propagates compressional guided wave energy with dispersion along an axial direction of the cylinder such that lower frequencies arrive earlier than higher frequencies at the bounding edge for coupling as shear waves to the seat portion.

22. A waveguide according to claim 1, together with at least one additional waveguide according to claim 1, constituting a first set of at least one waveguide and a second set of at least one waveguide, each of said first and said second sets being configured and oriented about a fluid in a region to guide ultrasound for effecting a fluid measurement, said first set propagating refracted ultrasound in a first set of planes that are parallel to each other, and said second set propagating ultrasound in planes which are neither parallel to each other nor parallel to planes of the first set of planes.

23. The waveguide system as set forth in claim 22, wherein said fluid measurement is a tomographic measurement of at least one of fluid sound speed, flow, temperature and turbulence.

24. A waveguide according to claim 1, and further comprising at least two further waveguides according to claim 1 each waveguide having a transducer for coupling ultrasonic wave energy to its standoff, and all said transducers being electrically connected in parallel in a pulse-echo configuration about a fluid such that signals received from the fluid are delayed in at least one of said waveguides and said two further waveguides to position signal reception in a quiet window between waveguide reverberations.

25. A waveguide according to claim 1, together with a flow cell or conduit having a fluid bounding wall, wherein the wall includes a recess shaped to closely receive said seat portion and couple ultrasonic energy along a fluid path from said exit face.

26. A waveguide according to claim 25, wherein the recess partially penetrates the wall and the exit face contacts a floor of the recess.

27. A waveguide according to claim 26, wherein the wall includes an internal face of the conduit formed parallel to the floor of the recess for directing a refracted signal path into fluid within the conduit.

28. A waveguide according to claim 25, configured to launch or receive a vertically polarized shear wave that zig-zags in the conduit wall, and further comprising means for correlating the wave in the conduit wall with one or more conduit characteristics selected from among pipe schedule, wall thickness and surface roughness to determine an enhanced measurement of pipe area or meter factor.

29. A waveguide according to claim 1, together with a plurality of further waveguides according to claim 1, constituting at least first and second sets of waveguides attached to a conduit and configured and oriented for ultrasonic interrogation of fluid in the conduit in first and second parallel planes, respectively, and further comprising means for measuring energy passing between said first and said second sets of wave guides along a plane which is skew to said parallel planes.

30. A waveguide according to claim 1, wherein said waveguide is integral with a flow cell and the waveguide and flow cell are formed of phenolic plastic.

31. A waveguide according to claim 1, further comprising a flange about the waveguide configured to clamp and seal against a steam conduit while acoustically isolating the waveguide from the conduit wall so that the standoff couples ultrasonic signals directly to steam in the steam conduit.

32. A waveguide according to claim 1, operable as a broad band waveguide and mounted directly in a valve or conduit to sense fluid-generated noise indicative of flow.

33. A waveguide according to claim 1, further comprising a transducer coupled to the standoff for applying ultrasonic energy thereto, and actuation means for actuating the transducer with a drive signal having a substantially constant envelope and complementary components of two frequencies to produce a chirped signal at the exit face with predetermined and monotonically changing intervals between zero crossings.

34. A waveguide comprising a standoff portion connected to a seat portion formed of a plate, wherein the standoff portion has a first end for coupling to a transducer and a second end extending to the seat, and has a length between said first and second ends effective to substantially dissipate high temperature applied at the seat when the seat is coupled to a hot conduit, wherein the seat has a cross section effective to propagate shear wave energy non-dispersively and without mode conversion to an exit face and radiate said energy as a narrow and directional beam into the conduit, and said standoff portion is configured to couple energy which has been applied at said first end to the seat portion as shear wave energy which travels in a defined direction through the seat portion to said exit face thereby controlling an angle of refraction at the exit face.

35. A kit for the field fabrication of a spoolpiece or flow conduit for ultrasonic measurement of fluid flow in a desired plane, such kit consisting of a waveguide having a standoff portion and a seat portion connected to the standoff portion, the seat portion being formed of a plate, wherein the standoff portion has a first end for coupling to a transducer and a second end extending to the seat, and has a length between said first and second ends effective to substantially dissipate high temperature applied at the seat when the seat is attached to a hot conduit, wherein the seat has a cross section effective to propagate shear wave energy non-dispersively and without mode conversion to an exit face and radiate said energy as a narrow and directional beam, and said standoff portion is configured to couple energy which has been applied at said first end to the seat portion as shear wave energy which travels in a defined direction through the seat portion to said exit face thereby controlling an angle of refraction at the exit face, so that field fabrication is achieved simply by securing the exit face to the spoolpiece or conduit in an orientation to position the beam in said plane.

36. A waveguide according to claim 34, wherein the conduit contains steam, and further comprising means for pressure coupling the waveguide to the conduit.

* * * * *